(12) United States Patent
Torrence et al.

(10) Patent No.: US 6,214,805 B1
(45) Date of Patent: Apr. 10, 2001

(54) RNASE L ACTIVATORS AND ANTISENSE OLIGONUCLEOTIDES EFFECTIVE TO TREAT RSV INFECTIONS

(75) Inventors: Paul F. Torrence, Silver Spring, MD (US); Robert Hugh Silverman, Beachwood; Nick Mario Cirino, Cleveland Heights, both of OH (US); Guiying Li, Branford, CT (US); Wei Xiao, North Potomac; Mark R. Player, Gaithersburg, both of MD (US)

(73) Assignees: The United States of America as represented by the Department of Health and Human Services, Washington, DC (US); The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 08/962,690

(22) Filed: Nov. 3, 1997

Related U.S. Application Data

(63) Continuation-in-part of application No. 08/801,898, filed on Feb. 14, 1997, now Pat. No. 5,998,602.
(60) Provisional application No. 60/011,725, filed on Feb. 15, 1996.

(51) Int. Cl.[7] .............................. A61K 31/70; C12N 5/06; C07H 24/00; C07H 24/02
(52) U.S. Cl. ........................ 514/44; 435/375; 536/24.5
(58) Field of Search ........................ 435/6, 375; 514/44; 536/24.3, 24.32, 24.5, 25.2

(56) References Cited

U.S. PATENT DOCUMENTS

| 5,532,130 | 7/1996 | Alul ........................................ 514/44 |
| 5,583,032 | * 12/1996 | Torrence et al. ..................... 435/91.1 |

FOREIGN PATENT DOCUMENTS

| Wo 94/09129 | 4/1994 | (WO) . |
| 95/22553 | * 8/1995 | (WO) . |
| WO 95/22553 | 8/1995 | (WO) . |
| 97/14792 | * 4/1997 | (WO) . |

OTHER PUBLICATIONS

Antisense '97: A roundtable on the state of the industry. Nature Biotechnology 15: 519–524, Jun. 1997.*
Gewirtz et al. Facilitating oligonucleotide delivery: Helping antisense deliver on its promise. Proc. Natl. Acad. Sci. USA 93: 3161–3163, Apr. 1996.*
Gura. Antisense has growing pains. Science 270: 575–577, Oct. 1995.*
Rojanasakul. Antisense oligonucleotide therapeutics: Drug delivery and targeting. Adv. Drug Delivery Rev. 18: 115–131, 1996.*
Stull et al. Antigene, ribozyme and aptamer nucleic acid drugs: Progress and prospects. Pharm. Res. 12: 465–483, Apr. 1995.*
Whitton. Antisense treatment of viral infection. Adv. Virus Res. 44: 267–303, 1994.*
Player et al., 1998, "Methods for the Characterization of Phosphate–Stabilized 2–5A–Antisense Chimeras", Bioconjugate Chem. 9:137–142.
Barnard et al., 1997, "Anti–Respiratory Syncytial Virus (RSV) Activity of 2–5A Antisense Oligonucleotide Chimeras", Antiviral Res. 34:A89.
Cirino et al., 1997, "Targeting RNA Decay with 2',5' Oligoadenylate–Antisense in Respiratory Syncytial Virus–Infected Cells", Proc. Natl. Acad. Sci. USA 94:1937–1942.
Player et al., 1997, "Targeting HIV mRNA for Degradation: 2,5A Antisense Chimeras as Potential Chemotherapeutic Agents for AIDS", Nucleosides & Nucleotides 16:1221–1222.
Torrence et al., 1997, "Recruting the 2–5A System for Antisense Therapeutics", Antisense & Nucl. Acid Drug Dev. 7:203–206.
Xiao et al., 1996, "Synthesis and Characterization of Composite Nucleic Acids Containing 2',5'–Oligoriboadenylate Linked to Antisense DNA", Antisense & Nucl. Acid Drug Dev. 6:247–258.
Beigelman et al., 1995, "Synthesis and Biological Activities of a Phosphorodithioate Analog of 2',5'–Oligoadenylate", Nucl. Acids. Res. 23:3989–3994.
Maitra et al., 1995, "Catalytic Cleavage of an RNA Target by 2–5A–Antisense and 2–5A Dependent RNase", J. Biol.Chem. 270:15071–15075.
Merolla et al., 1995, Respiratory Syncytial Virus Replication in Human Lung Epithelial Cells: Inhibition by Tumor Necrosis Factor–α and Interferon–β, Am. J. Respir. and Crit. Care Med. 152:1358–1366.

(List continued on next page.)

Primary Examiner—Robert A. Schwartzman
Assistant Examiner—Thomas G. Larson
(74) Attorney, Agent, or Firm—Lyon & Lyon LLP; James H. Shalek, Esq.; Kristin H. Neuman, Esq.

(57) ABSTRACT

The present invention relates to methods of inhibiting infection by RNA viruses with complexes of an activator of RNase L and an oligonucleotide that is capable of binding to the genome, antigenome or mRNAs of a negative strand RNA virus to specifically cleave the genomic or antigenomic RNA strand of the virus. In accordance with the present invention, the methods and complexes of the invention may be applied to target any negative strand RNA virus. The invention in one embodiment relates to a covalently linked complex of an oligonucleotide that is capable of binding to the genomic or antigenomic template RNA strand of a negative strand RNA virus and/or binding to an mRNA of a viral protein (an "antisense oligonucleotide") coupled to an activator of RNase L. In a preferred embodiment of the present invention, the oligonucleotide component of the complex is complementary to a region of the viral genomic RNA strand characterized by repeated or consensus sequences.

15 Claims, 30 Drawing Sheets

OTHER PUBLICATIONS

Figure 2A:
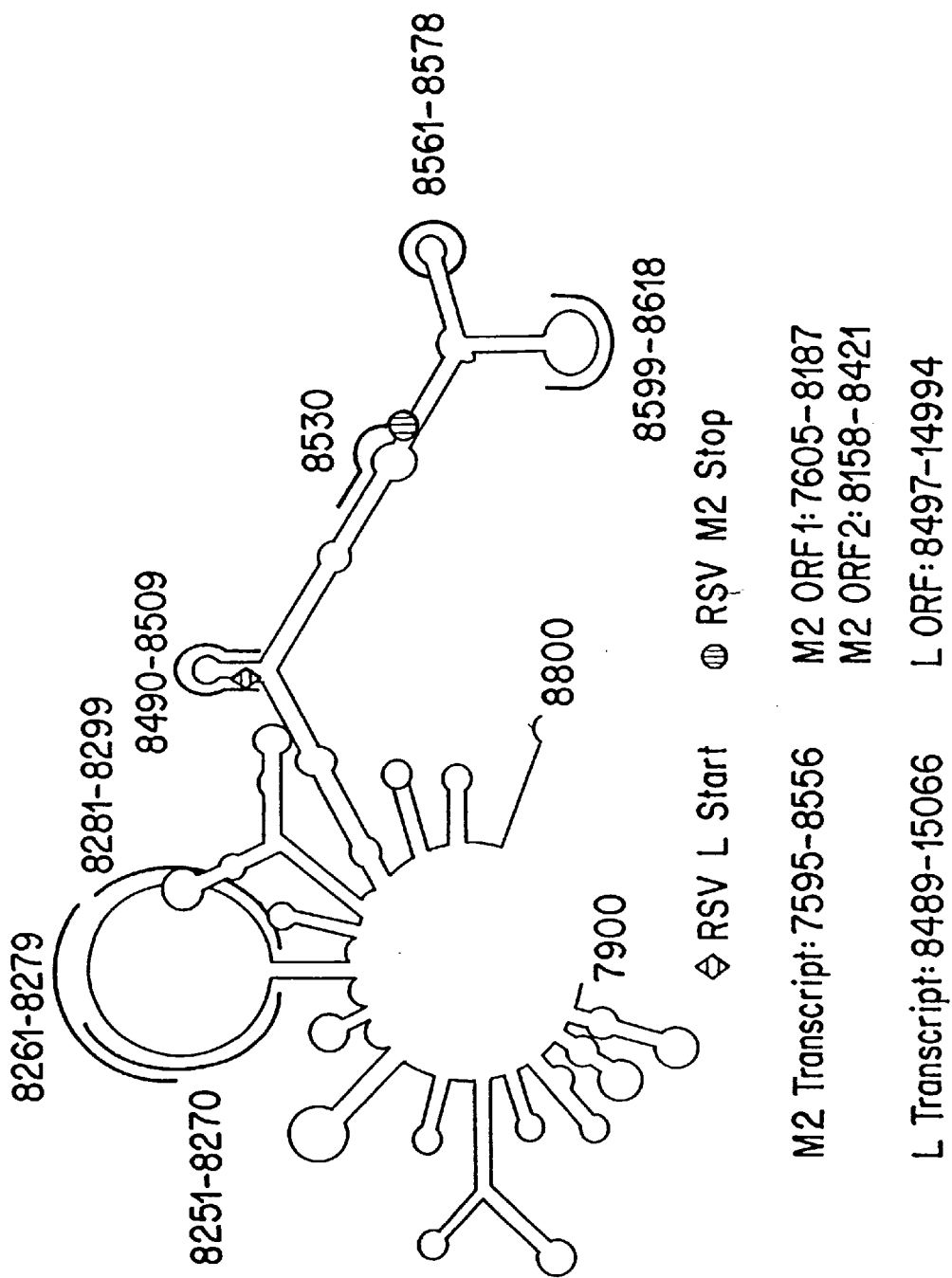

Panuska et al., 1995, "Respiratory Syncytial Virus Induces Interleukin–10 by Human Alveolar Macrophages", J. Clin. Invest. 96:2445–2453.

Englund, 1994, "High–Dose, Short Duration Ribavirin Aerosol Therapy Compared with Standard Therapy in Children with Suspected Respiratory Syncytial Virus Infection", J. Pediatrics 125:635–641.

Maran et al., 1994, "Blockage of NF–κB Signaling by Selective Ablation of an mRNA Target by 2–5A–Antisense Chimeras", Science 265:789–792.

Silverman, 1994, "Fascination with 2–5A–Dependent RNase: A Unique Enzyme that Functions in Interferon Action", J. Interferon Res. 14:101–104.

Swiderski et al., 1994, "Polystyrene Reverse–Phase Ion–Pair Chromatography of Chimeric Ribozymes", Analytical Biochemistry 216:83–88.

Xiao et al., 1994, "Synthesis of a 5'–Thiophosphate Analogue of 2–5A, a Phosphatase Resistant Activator of the 2–5A Dependent Ribonuclease", Bioorganic & Med. Chem. Letts 4:2609–2614.

Balotta et al., 1993, "Antisense Phosphorothioate Oligodeoxynucleotides Targeted to the vpr Gene Inhibit Human Immunodeficiency Virus Type 1 Replication in Primary Human Macrophages", J. Virol. 67:4409–4414.

Cirino et al., 1993, "Restricted Replication of Respiratory Syncytial Virus in Human Alveolar Macrophages", J. Gene. Virol. 74:1527–1537.

Hassel et al., 1993, "A Dominant Negative Mutant of 2–5A–Dependent RNase Suppresses Antiproliferative and Antiviral Effects of Inteferon", EMBO J. 12:3297–3304.

Lesiak et al., 1993, "2',5'–Oligoadenylate–Antisense Chimeras—Synthesis and Properties", Bioconjugate Chem. 4:467–472.

Midulla et al., 1993, "Concise Communication: Respiratory Syncytial Virus Lung Infection in Infants: Immunoregulatory Role of Infected Alveolar Macrophages", J. Inf. Dis. 168:1515–1519.

Torrence et al., 1993, "Targeting RNA for Degradation with a 2',5'–Oligoadenylate–Antisense Chimera", Proc. Natl. Acad. Sci. USA 90:1300–1304.

Agrawl, 1992, "Antisense Oligonucleotides as Antiviral Agents", Trends Biotechnol. 10:152–158.

Panuska et al., 1992, "Respiratory Syncytial Virus Infection of Alveolar Macrophages in Adult Transplant Patients", Am. Rev. Resp. Dis. 145:934–939.

Gribaudo et al., 1991, "Interferon Action: Binding of Viral RNA to the 40–Kilodalton 2',5' Oligoadenylate Synthetase in Interferon–Treated HeLa Cells Infected with Encelphalomyocarditis Virus", J. Virol 65:1748–1757.

McIntosh and Chanock, 1990, "Respiratory Syncytial Virus", In: Virology, 2nd edition. Fields and Knipe, eds., Raven Press, Ltd, New York, pp. 1045–1072.

Letsinger et al., 1989, "Cholesteryl–Conjugated Oligonucleotides: Synthesis, Properties, and Activity as Inhibitors of Replication of Human Immunodeficiency Virus in Cell Culture", Proc. Natl. Acad. Sci. USA 86:6553–6556.

Rysiecki et al., 1989, "Constitutive Expression of a 2',5'–Oligoadenylate Synthetase cDNA Results in Increased Antiviral Activity and Growth Suppression", J. Interferon. Res. 9:649–657.

Zuker, 1989, "Computer Prediction of RNA Structure", Meth. Enzymol. 180:262–288.

Zuker, 1989, "On Finding All Suboptimal Foldings of an RNA Molecule", Science 244:48.

Goodchild, 1988, "Inhibition of Human Immunodeficiency Virus Replication by Antisense Oligodeoxynucleotides", Proc. Natl. Acad. Sci. USA. 85:5507–5511.

Gruenert et al., 1988, "Characterization of Human Tracheal Epithelial Cells Transformed by an Origin Defective Simian Virus 40", Proc. Natl. Sci. Acad. USA. 85:5951–5955.

Chebath et al., 1987, "Constitutive Expression of (2'–5') Oligo A Synthetase Confers Resistance to Picornavirus Infection", Nature 330:587–588.

Freier et al., 1986, "Improved Free–Energy Parameters for Predictions of RNA Duplex Stability", Proc. Natl. Acad. Sci. USA 83:9373–9377.

Zamecnik et al. 1986, "Inhibition of Replication and Expression of Human T–Cell Lymphotropic Virus Type III in Cultured Cells by Exogenous Synthetic Oligonucleotides Complementary to Viral RNA", Proc. Natl. Acad. Sci. USA. 83:4143–4146.

Hall et al., 1983, "Aerosolized Ribavirin Treatment of Infants with Respiratory Syncytial Viral Infection", N. Eng. J. Med. 308:1443–1447.

Taber et al., 1983, "Ribavirin Aerosol Treatment of Bronchiolitis Associated with Respiratory Syncytial Virus Infection in Infants", Pediatrics 72:613–618.

Floyd–Smith et al., 1981, "Interferon Action: RNA Cleavage Pattern of a (2'–5') Oligoadenylate–Dependent Endonuclease", Science 212:1020–1032.

Wreschner et al., 1981, "Ribosomal RNA Cleavage, Nuclease Activation and 2–5A(ppp(A2'p)nA) in Interferon–Treated Cells", Nucl. Acids Res. 9:1571–1581.

Wreschner et al., 1981, "Interferon Action–Sequence Specificity of the ppp(A2'p)nA–Dependent Ribonuclease", Nature 289:414–417.

Salser, 1977, "Globin mRNA Sequences: Analysis of Base Pairing and Evolutionary Implications", Cold Spring Harbor Symposium on Quantitative Biology 42:985–1002.

* cited by examiner

```
   1  acgagaaaaa aagtgtcaaa aactaatatc tcgtaattta gttaatacac
  51  atataaacca attagattag ggtttaaatt tattcctcca agattaaaat
 101  gataacttta ggattagttc actaaaagtt atttaaaaaa ttatatgatt
 151  tttaattttt aataactata attgaataca gtgttagtgt atagctatgg
 201  gaatttttat tataagatcc ttattcatta ttcattatga agttgtata
 251  acagactacc tgtgatttta atcagttttt taagttcatt ggttgtcaag
 301  ctgtttaaca attcacttag gtaaggatat gtagattcta ccatatataa
 351  atggttatag tttagttctg ttgatctgaa atttaaaaca tgattgaacc
 401  attttaagat gttcatatgc ttatgattta aagtttatt gctgaaaact
 451  tcattacgtc cagctataga atatgatagt atatctccac taacaacact
 501  ctttagtttt gacaatgcag tattaattcc ttttttttgtt atagggtaac
 551  aaagaaaggg tatcaaactt ttaatatttg catcaataga ctctttatca
 601  gctttcttag gcatgatgaa attttggtt cttgatagta tcaatttagc
 651  attttgtact acattaaata ctgggaatat attcgcagga cctattgtaa
 701  ggactaagta aacctccgat cccttttaact tactgcctaa gcatacataa
 751  gtttttaata tagttatatt gtctaatttg aaatcaatat catcttgagc
 801  atgatatttt actattaaca tacatttatt aactgaggaa cagtacttgc
 851  actttcttac atgcttgctc cattctatta gttggttgca tctgtagcag
 901  gttacagaca attcggcatc acagacaaaa agactgatag gttcagcaaa
 951  ctttatatgt aaataagacc aatgaatgtt gttggttgca tctgtagcag
1001  gaatggtcaa attttcacca taatcaatgt tgatatgtcc attgtacagc
1051  cttaaaaact caataggtaa actatgatca ttgcaatctt tcagacttct
1101  gtaaatatat cttatgtcag gatgaagttc cactactgta cgcaataata
1151  aattccctgc tccttcacct atgaatgcta tacaattggg atctttaatt
1201  ttaagatctt ttaaaatata ctctatacta attttacaac ctgtagaact
1251  aaatacaaaa ttgaatctat taatatgatg ccaaggaagc atgcagtaaa
1301  gtgatgtgct attgtgcact aaagatattt ggtgggaagt agtagtgtaa
1351  agttggttgg atttggctgt attgcctgaa tgatctataa ttctatcaag
1401  cacaaccata gggaataaat tatacaaatc ttgtttgctg taattggttc
1451  taatcattgc agacgattta ataagcttct tattagataa caatggtaac
1501  attattgagt caacattttt acctatacaa tagtcattca gtgtcttttt
1551  gtcattactt taatcggat tggctagtat attctctagg gtttctggtg
1601  taggatgata taatttgttg taattatttt ctaattcaga attagcaatc
1651  cttatatgtt tagttaatag atgagtatta tctgagaagt tataattaat
1701  gcagaagaga ttagaagtat aaaattcatc attgaatttg tgtttatttt
1751  taatgtgtat tctatctata tttatcaatc ccattctaac aagatctata
1801  taagttaata ttgctttcat atgtgttgga tgataatcta tgttaacaac
1851  ccaagggcaa actgtgaatt ctgctacatt aagacgttta agaaaccata
1901  atttgaagct atgacatcct tttactctat gtaaacttgc atcttggcta
1951  agaatgtatt tgataacttt tgttctaaa aataccttag acatagactt
2001  ccaataacta ctgtctatta attccaatac acatagaaga tctgaagtgt
```

FIG.1A

```
2051  tcatatcaca ctccagcttt gctttgccat aacctttatg aaaacacaag
2101  agataggtct tataagcatt gaagaaaact ttcaaattaa taaacatatg
2151  atcagttata tatccctctc cccaatcttt ttcaaaaata cctttagaat
2201  ctttcataag ttgtataatc agaatccaat gtccagctaa attagtactt
2251  aaaatgtaag tattatgaaa atagtcagat attttatgtg ccaatattaa
2301  attagaatta acatgagatc cagatttgag tgttttatta cttaagaata
2351  attccacata ttgagtcaaa cttattttgt ctggtaaaaa catatgctgt
2401  ttttgtatca cttgttttaa cttgtgaata tcaacatcac ctgtgaatat
2451  gggaggtttc atcaaatgta tctcattaag cttaggtatg agaataattc
2501  tgttaggaca tacattagta aattgttcta ctactgacat taaactaagg
2551  ccaaagctta tacagttttg gaatactatg tcaatatctt catcaccata
2601  cttttctgtt aatatgcgat taatagggct agtgtcaaag tgataatttg
2651  ttgttctata agctggtatt gatgcaggga attcacatgg tctactactg
2701  actgtaaggc gatgcaaata attgacactt aaatattgtg gaaataattt
2751  cttggccttt tcatatgtta acccaagggt tcctatgctg agttcttcca
2801  tgaattcatc cttgttatct atagatgcat acacccaatc caatttgct
2851  aatagatcta tttgatctct ctgttttttg gttaagactt gtctattata
2901  aactaacatt attttttttct cttgtgtaga tgaaccaacc catggtttag
2951  tgggtcctct ctcaccacgt gttaaactgt taacattata tttctctata
3001  attatgccac tagatatagt gcttgtagta tatttgatgt ccattgtata
3051  catgatactg ggtgatgtaa caccaactat attggataaa gaccaagatc
3101  tttccctaac atatttgctt aattcagtaa tacttaggtt ttccatactc
3151  aatatctctc ttttatctct gttacaatcc aatggaagta tccttataag
3201  caaagttatg ttttttcctca tcatctcagt ggctctatca atatctgtta
3251  agtctatggc agaagttttt tccagtatgt tagttataga ttttgtacct
3301  gatataagat ttactatttt ctctgcttta taaaagggta aactttcata
3351  aacaactctt agcccatgag gatatgtagg ttctatattt tgcataatat
3401  catttagatc tatctctgta gtagtataat gttgtgcact tttggagaat
3451  attttgtttg gagctgtact caaaacctct gtaactgcca gtctattgat
3501  ttcgctagta attttagctt gtctctcaga ccctaaagct tgaggatctc
3551  tcatcaatgt tacgaattca gcattagggt ttttgtcaaa cgtgattatg
3601  catgttaaga acttattcaa tctatcatct gacagatctt gaagtttatc
3651  ttttaagtca tggtttgtat aataactaag tatgaacaca gagtgaacta
3701  tagcctctgt gaggaagtca ggagttcttc tatagaaact tcgatataac
3751  aagttgggat caccaccacc aaataacatg ggtaaattca tatacaatgt
3801  taatgctgta tcaatattat caagattaaa aaaggttttt aagtgtttca
3851  gaacctttaa tatgtccaaa tatagtttat tgttacataa tgcatgattt
3901  tttaattgta gagcaatctg attatataac catacatttc taaatattaa
3951  actgcataat agactttcac ctctatattc taattcttgt gtcaaactac
4001  ctatagattc tagactcact ttgaaatcat caagtatagt gtttatccac
4051  ggtcccactc ttaggacttt ctttatacta gctgggtaat ataccgtt
4101  atgttgaatt gttttactca taaattgcat atctcgtgat atataagtct
```

FIG.1B

```
4151  cagttccttt taatttgtgg cctatgcctg catactcttt atacagtaat
4201  ttaaggctat ttaatgctag caaataatct gcttgagcat gagtttgacc
4251  ttccatgagt ctgattggtt tgcttatatc tattgattga ttgtcaccat
4301  taattaaagc agtaattgag aatttccctt tgagagatat tagatccaat
4351  agtgatatag cttctatggt ccacagtttt tgacaccacc cttcgatgcc
4401  acccatgtga tatctatata atccactttg ttcatctaca ttgttaagat
4451  ctacaatatg atctcctata tagggggtg catgcctata tgtgcatatt
4501  attgtgacat gaggaatagt taaatgtaac caggaaaata gagattgtac
4551  accatgcagt tcatccagca catcactaca aatacatgac gtttcatatc
4601  gaaatgcttg attgaatttg ctgagatctg tgatgataga gcacttacta
4651  atgtaattgt tgtaattatc attgtagcga tttgatttgt tacttattcc
4701  tgctttcaat tctaatattt tttgtagttc tagatcacca tatcttgtaa
4751  gactttcagg aaagaattgt aaaatgtttt cagctatcat tttctctgcc
4801  aatatttgaa cctgtctgaa cattcccggt tgcattgcaa acattctacc
4851  tacactgagt tctctttctt tgcctgtcaa tgataccaca tgattagggt
4901  tgttgagata acttcgatta actacacagt tgtataaatc acattcattg
4951  aatttgttat ctcttaaata atactctaat actcttcttg atttatcact
5001  ctcggaaaat tttaattttt catgttctat atagtttgt atgtgtgatg
5051  gcatgtaatt tctagggaaa ctagtccata tcaaattttt aggaggtgat
5101  atagctttat catttataat catttcaaga tccactttt taggcaaccg
5151  aaactcacga tagaaacgta gtcctgataa cacaatcaaa tctctttctg
5201  taagttccaa caaagaagga taagtgttta gtttatagta agttaaccat
5251  cttaagggta aaacaatagc atttcttaaa gtaggccatc tgttgtaatt
5301  atttacaaac ccttttataa ttctatatat aaaggcacct cttaacatac
5351  tcagactgct taacaagtaa aatttggtct cattgcaatt aatttttaaca
5401  gcatccatgg cttgtctttc atctaccatt gggtgtccaa atattctgaa
5451  caaaaatat agttcactca gattgttaag gttattgtca cctgcaagct
5501  taattaattt aaggaactta cttaatagaa ttatccatct gccatttatt
5551  atattatcgg acactgtctt atctaataat gtatgacata ctcttgatag
5601  cagattttc tgagctttat tagcagcatc tgtgatgttg ttgagcatac
5651  tattataaaa tcgttttctg aattgatctt cttctgttat atttaaaatt
5701  agagacataa taaatccctc tacctctttt attatgtaga accctcatt
5751  gtgaaatagc tttagtatac aatctccata aaggaatagt tgtgtcaaga
5801  taacattatt gaatccgcat cttaagccta agcttttatt taatgtgttc
5851  aagcagttac taatccatgt aattaaacaa acatttaatc tactaaggct
5901  aatatcttc catgtcaaga attgattata ggttgtcaca gtaattcttt
5951  tgagttcctt atgataaact atacaaccat attggttcaa aataaattga
6001  aatccactaa gagtttgatt atctatcaat gtaaacccat ggttttttac
6051  ctcatttgat cgatactgtg ttaatatgtt gtttaatttt tgtgtataagt
6101  taaaccaatg tattaaccat gatggaggat gttgcattga acacatcaat
6151  ttcttcaaga gtgttgtttt gattgtgtct ttttgttttg tagagtgatt
6201  tttgtctgct ttaagatgag attgattatc tttaacagct gaaagtatat
```

FIG. 1C

| | | | | | |
|---|---|---|---|---|---|
| 6251 | tttgtctgct | tatggtcgta | ataactgagt | tgtcttcatc | ttgtccattg |
| 6301 | ttggatttaa | tcttgtcctt | ttctttaagt | tgtcttcatc | ttgtccattg |
| 6351 | atagactttg | acatcactta | tttctatagc | tcttcttatt | atctttttaa |
| 6401 | gtaaattagt | ggtagcaatc | tgttctgacg | aggtcatact | cttgtatgtc |
| 6451 | ataagtaatg | actgaaaata | agtaggttct | tctaatttta | tttcaccttt |
| 6501 | atgatactta | gatattaagg | actgtgttat | atttagtttc | tttagattca |
| 6551 | tgtgttctat | taatggattt | tgtctactaa | ttaagttggt | ataatcattt |
| 6601 | ttgagataag | gaccattgaa | tatgtaactt | cctaaagcat | tacactctga |
| 6651 | gaaagagata | acacctttta | aataactatc | ggttagataa | acattagcag |
| 6701 | aatttccatt | aataatggga | tccatttgt | cccacaactt | gaattgtttg |
| 6751 | aattaataat | gtaacgatgt | ggtgagtgtt | agaattgagt | gttatgacac |
| 6801 | taatatatat | attgtatata | tatcctcaat | aatacctaga | tgttgtagaa |
| 6851 | aaatttgaat | tgtgtcaatc | aattcttgag | aggtccaatg | gatttcattg |
| 6901 | aatgtttgat | tcggtgagta | catatggtta | tttgggttgt | tttgattgaa |
| 6951 | atatagtgtg | ttcttttgat | tatacatagt | aactctacat | ctacttgtta |
| 7001 | ttagtatgga | agttatacta | caaggatatt | tgtcaggtag | tatcattat |
| 7051 | tttggcatgg | tcatttgtat | cactaacagt | tgattctttt | gggttgttga |
| 7101 | tggttatgct | cttatggata | tccaatgtgt | ttttgatggt | tttcttcaat |
| 7151 | acgtctgctg | gcaatctttt | taacagatgg | atagtttgtt | tattgttttt |
| 7201 | cctgttgctt | tcaatatatg | atatgacagt | attgtacact | cttatcttgg |
| 7251 | gtgaatttag | ctcttcattg | tccctcagct | ttttgatatc | atcactattg |
| 7301 | agttcagtga | ggagtttgct | catggcaaca | catgctgatt | gtttagttat |
| 7351 | attgtttatt | gatcctatat | aactctctag | cactccaact | acaccaagag |
| 7401 | catactcttc | tgttctgtcc | aactctgcag | ctccacttat | ttctgataag |
| 7451 | gtatctatac | ttttatccat | agacttaagt | attctgttta | acataaagtt |
| 7501 | ttgtcttaca | agcagtgcat | ggggtggcca | ttcaaaataa | ttatgactaa |
| 7551 | aatgacacct | cttaccattt | aagcaatgac | ctcgaatttc | aaatttgcaa |
| 7601 | ggattccttc | gtgacatatt | tgccccagtt | ttcatttta | cagatggtaa |
| 7651 | gttaatctgg | cattcaattg | tgttttatat | aactataaac | taggaatcta |
| 7701 | cttaaatagt | gtaagtgaga | tggtttatag | atgagagttt | cgatgaagtt |
| 7751 | cagatttaa | gaaaatccaa | tgacagatgg | gttgtctatg | agcagatagt |
| 7801 | aaaccattgt | aagaacatga | ttaggtgcta | ttttatttta | gttactaaat |
| 7851 | gcaatattat | ttataccact | cagttgatct | ttgcttagtg | tgactggtgt |
| 7901 | gcttctggcc | ttacagtata | agagcagtcc | aacagcaatt | aatgataaca |
| 7951 | atattactat | aatcactata | attatagtag | ttatcatgat | atttgtggtg |
| 8001 | gatttaccag | catttacatt | atgtaataat | tcatcggatt | tacgaataaa |
| 8051 | tgctaggctc | tggttaatct | tctcgttgac | ttgagatatt | gatgcatcaa |
| 8101 | attcatcaga | ggggaatact | aatgggtcat | agaaatttat | tattggttca |
| 8151 | cctttacat | agagactttt | accttcttgc | ttatttacat | aatataatgt |
| 8201 | gttacctaca | gacacagtgt | ccatcccttt | atttgataca | taatcgcacc |
| 8251 | cgttagaaaa | tgtctttatg | attccacgat | ttttattgga | tgctgtacat |
| 8301 | ttagttttgc | catagcatga | cacaatggct | cctagagatg | tgataacgga |

FIG.1D

```
 8351  gctgcttaca tctgtttttg aagtcataat tttacaatca tatttggggt
 8401  tgaatatgtc aacattgcag agatttattt cacttggtaa tgttaaactg
 8451  ttcattgtgt cacaaaatac tcgatttgat tgaactttac atgtttcagc
 8501  ttgtgggaag aaagatactg atcctgcatt gtcacagtac catcctctgt
 8551  cagttcttgt taaacagatg ttggaccctt cttttgtgtt ggttgtacat
 8601  agaggggatg tgtgtagttt ccaacagggt gtatctataa caccatatag
 8651  tggtaattgt actacatatg ctaagacttc ctcttttatt atggacatga
 8701  tagagtaact ttgctgtcta actatttgaa cattgttgga cattaacttt
 8751  ttctgatcat ttgttatagg catatcattg attaatgaca ataattcact
 8801  attagttaac atgtaagtgc ttacaggtgt agttacacct gcattaacac
 8851  taaattccct ggtaatctct agtagtctgt tgttcttttg ttggaactct
 8901  atcacagttt ctatatttga tatgctgcag ctttgcttgt tcacaatagg
 8951  taacaattgt ttatctatat agttttgag gtctaacact ttgctggtta
 9001  agacactaac tccatttgat aagctgacta gagccttgtt tgtggatagt
 9051  agagcacttt tgatcttgtt cacttcccct tctaggtgca ggaccttaga
 9101  tacagcaacg ccactggcga ttgcagatcc aacacctaac aaaaaaacaa
 9151  gaaatcttct tttcctttc ttgcttaatg ttacattggt tttttggca
 9201  ttgttgagtg tataattcat aaaccttggt agttctcttc tggctcgatt
 9251  gtttgttggt ggtgtgcttt gcatgagcaa ctgcaattct gttacagcat
 9301  ttttatattt atctaattct tgttttatca atttaccttt agcatctgtt
 9351  ccattacact tattttcctt gatattactt aattctatag ttataacact
 9401  ggtataccaa ccagttctca gagcactaag atagcctttg ctaactgcac
 9451  tgcatgttga ttgataaaat tcttcagtga tgttttgacc agaagcaaaa
 9501  caaaatgtga ctgcagtgag gattgtggta attgcatttg ctttgaggat
 9551  tagcaactcc attgttattt gccccagagt ttattttgat tctgtttaag
10001  tggtggtggg tatgctgcag ggtacaaagt tggcgttgtt aaagtgaaaa
10051  tcattattgg gtttgcttgg tggtttgttt ggcgttgtt ttgtggtggg
10101  cttgctgggt tgtgtttgag ttgttgttgt gttttggtc ttgactgttg
10151  tggattgcag ggttgacttg actcctggtg ttgttgaagc tagtatggtg
10201  gtgatttgtg atgtaatttc agacggatta gagggactga ttccaagctg
10251  aggattctgg gtgaggtatg ttggggttgt gttcttgatc tggcttgttg
10301  catcttgtat gattgcagtt gttggtgtga ctttgtggtt tgccgaggct
10351  atgaatatga tggctgcaat tataagtgaa gttgagatta tcattgccag
10401  aatggataat gtgatttgtg ctacagattt aagatttaac ttatataagc
10451  acgatgatat gaataataaa tgattgagag tgtcccaggt cctttctaat
10501  gtcttagcgg tgcgttggtc cttgtttttg gacatgtttg catttgcccc
10551  aatgttattg ttagtcttga tatcctagtt cattgttatg actatttta
10601  attaactact ttatagtatg gatagtggtt tgcatggtgg gatgttaatg
10651  aggtgttgta aagaggtagg ggttgttcat ttttaaatgc aaggttactg
10701  ttttgggctg ttggattgat gaatgctatg tgttgactcg agctcttggt
10751  aactcaaagg ttttgttatg gaatacgtta tattcacaaa gtttgtttag
10801  tattgcaatc atgatggaga ttatgattag caaagagatt attgttgtga
```

FIG.1E

```
10851  tcatgtgtat tagtgtaaag taaggccaga atttgcttga gaattctatt
10901  gttatggatg tattttccat tggttgattc tgtatggtgt gtggacttgt
10951  ctatgttaac agatattgtg attagttgga tttcctccaa tgattatttg
11001  gaaccacaga atattttta ttaacttatt tgagtactag atctgataaa
11051  caatgacttg ggatgatctg ggacttcaga taagttttgt ttgattggtt
11101  gaaccacaga gtgtttgtga ttgtgatggt gaagtgaaga atgtaggtag
11151  aaagtttgta tgaattaaca cagtgatgta gaggaaaaag gttaatcttc
11201  catgggtttg attgcaaatc gtgtagctgt gtgcttccaa tttgtggtaa
11251  cataatatat actttctttt tctaggtaag ctccaagatc tactatgaat
11301  tgactttgtg gctttatgta tttgaatgct cctttgttgt cagtcactgt
11351  gatgactaat agtaatcctg agtaagggat gattttttgca tttgtgatag
11401  cattttgaa ttcagtggtt gttatatttt caagtgtgtt cagatcttta
11451  tttctgacac tgatggatct taggtatgtt ggtattatga ctttttttga
11501  tgttactatg ttttcaaatt cacataaagc aataatatca tgtgtagggt
11551  tgagtgtctt catagtgaga tctttaactg tagtcaacat atttttttgat
11601  tttaggcatg ttagactaca tgccttgatt tcacagggtg tggttacatc
11651  atatgctagt ttgcttcttt catccaagga cacattagcg catatggtaa
11701  atttgctggg catttgtgct agcactgcac ttcttgagtt tatcatgact
11751  cttagtgaag gtcccttggg tgtggatatt tgtttcacta gtatgttgac
11801  attagctagt tcttttataa gtaaatctgc tggcatagat gattggaaca
11851  tgggcaccca tattgtaagt gatgcagggt catcgtcttt ttctaagaca
11901  ttgtattgaa cagcagctgt gtatgtggag ccttcgtgaa gcttgttcac
11951  gtatgtttcc atatttgccc cacccttttcc ttttttttgta actatattat
12001  agattttttc cgggtggtta gtttggatt ggctggttgt tttgttggct
12051  gtttggctga ttggcggatg gatgtttggt tggatgattg ggttggttag
12101  tttgttggtc ttctgttggt attgtgtgtt gatgtgaaga gtggtaacta
12151  atcagaaatc ttcaagtgat agatcattgt cactatcatt cccttccaat
12201  aggttgttca atttctctga tgttggattg agagacactt catctgatgt
12251  gtcttttgcc atcttttcac tttcctcatt cctgagtctt gccatagctt
12301  ctaatctgtc attggtcatt aatgcttcag ttctgatttt ttctatcatt
12351  tcttctctta aaccaatcat ggcatctctt ataccatccc gagcagatgt
12401  aggtcctgca cttgccacta ctaatgtgtg aagcattcct agtatttcac
12451  ttaattttc atcaatccta tctaatcttg ctgttatatt atcgtttgtc
12501  tgatcattta tttcttcgta tgaatagctg gattcttctt cattgttatc
12551  aaatgtttct atggtttctt tgtatagttt agaaaaggga ttatcacttg
12601  gtgtagggtc ttctttgaaa cttactagag gttttctttg ataattgggc
12651  ttgttccctg cagtatcatc tgtctcattt gttgggttga taatagttga
12701  atttgatgtt atagggcttt ctttggttac ttctatatct attgagttga
12801  ccctttattg attctaggaa tttagtagcc ctgttgtttg catcttctcc
12851  atggaattca ggagcaaact tttccatgat gatttatttg ccccattttt
12901  tattaactca aagctctaca tcattatctt ttggattaag ctgatgtttg
12951  atagcctcta gttcttctgc tgtcaagtct agtacactgt agttaatcac
```

FIG.1F

```
13001  accatttttct ttgagttgtt cagcatatgc ctttgctgca tcatatagat
13051  cttgattcct cggtgtacct ctgtactctc ccattatgcc taggccagca
13101  gcattgccta atactacact ggagaagtga ggaaattgag tcaaagataa
13151  taatgatgct tttgggttgt tcaatatatg gtagaatcct gcttcaccac
13201  ccaattttg  ggcatattca taaacctcaa caacttgttc catttctgct
13251  tgcacactag catgtcctaa cataatattt ttaactgatt tgctaagac
13301  tccccaccgt aacatcactt gccctgcacc ataggcattc ataaacaatc
13351  ctgcaaaaat cccttcaact ctactgccac ctctggtaga agattgtgct
13401  ataccaaaat gaacaaaaac atctataaag tggggatgtt tttcaaacac
13451  ttcatagaag ctgttggcta tgtccttggg tagtaagcct ttgtaacgtt
13501  tcatttcatt ttttaggaca ttattagctc tcctaatcac ggctgtaaga
13551  ccagatctgt cccctgctgc taatttagtt attactaatg ctgctataca
13601  taatattatc atcccacaat caggagagtc atgcctgtat tctggagcta
13651  cctctcccat ttcttttagc atttttttgt aggattttct agattctatc
13701  tcaatgttga tttgaatttc agttgttaag cttgccaatg ttaacacttc
13751  aaatttcatt tcttttccat taatgtcttg acgatgtgtt gttacatcta
13801  ctccatttgc ttttacatga tatcccgcat ctctgagtat ttttatggtg
13851  tcttctcttc ctaacctaga catcgcatat aacatcacta ttaacccagt
13901  gaatttatga ttagcatctt ctgtgattaa taacatgcca cataacttat
13951  tgatgtgttt ctgcacatca taattaggag tatcaatact atctcctgtg
14001  ctccgttgga tggtgtattt gctggatgac agaagttgat ctttgttgag
14051  tgtatcattc aacttgactt tgctaagagc catctttgta tttgccccat
14101  cttctatctt atatctctcc ttaattttaa attactataa ttttcaggct
14151  ccatctggac tatggagtat agttatgcat agagttgttg ttttagattg
14201  tgtgaatatt gtgttgaaat ttatggattg agatcatact tgtatattat
14251  gggagtatgc tttgtaggct taatgccaat gcattctaag aacccatcat
14301  gattgatgaa tattggcata gggaaagtgc catatttgt gttgtattca
14351  gtatattttt tatatttagt gcttcctact ttgtgtaata gtttcatttc
14401  atagttgacc aggaatgtaa atgtggcctg tttttcatca agttttctca
14451  ctatgcattc atgatttatc aagtatataa atttgtgtgt tatgatgtct
14501  ctggttagtg atgttattat ggtctcaagt gacaacggtc tcatgtctgt
14551  gatcatcagt ctttgtggtg tattatcatt gtgggttgtg tccatggttg
14601  ggttggctga attgatttat ttgccccatt tttgtcttct gttaagtttt
14651  atattaacta atggtgttag tgacattgat ttgctagttg atattaatta
14701  taatttatgg attaagatca aatccaagta attcagataa ttgattcata
14751  taattggtca ttgttgaatc acttagttttt ttggagaatt taatttcaca
14801  attgtcatct agtagaccat taggttgaga gcaatgtgtt aattccatca
14851  tttcccatat ataacctcca ttttgtagta ctggcattgt tgtgaaattg
14901  gattttacta caatattatt attagggcaa atatcactac ttgtaataac
```

FIG. 1G

```
14951  atgcacaaac acaatgccat tcaatttgat tgtatgtatc actgccttag
15001  ccaaagcgtt agttaaatgt attaatttat cagtatagca tgttattttt
15051  aacaatgcta cttcatcatt gtcaaacaaa ttttgtaatc taacttttat
15101  catactcaat gaattgctgc ccatctctaa ccaagggagt taaatttaag
15151  tggtacttat caaattctta tttgccccat tttttggtt tatgcaagtt
15201  tgttgtacgc attttttcgc gt
```

FIG.1H

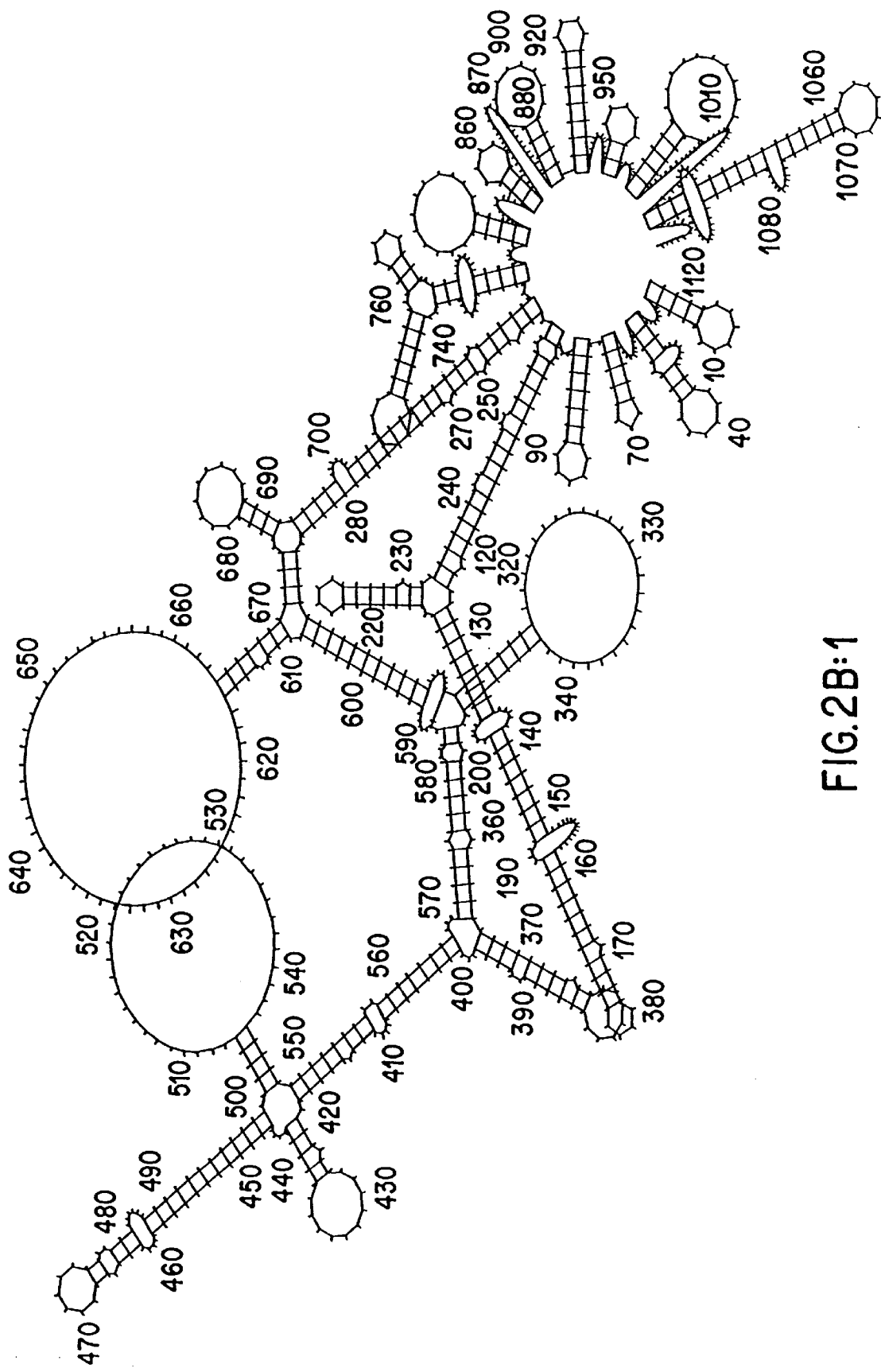
FIG.2B:1

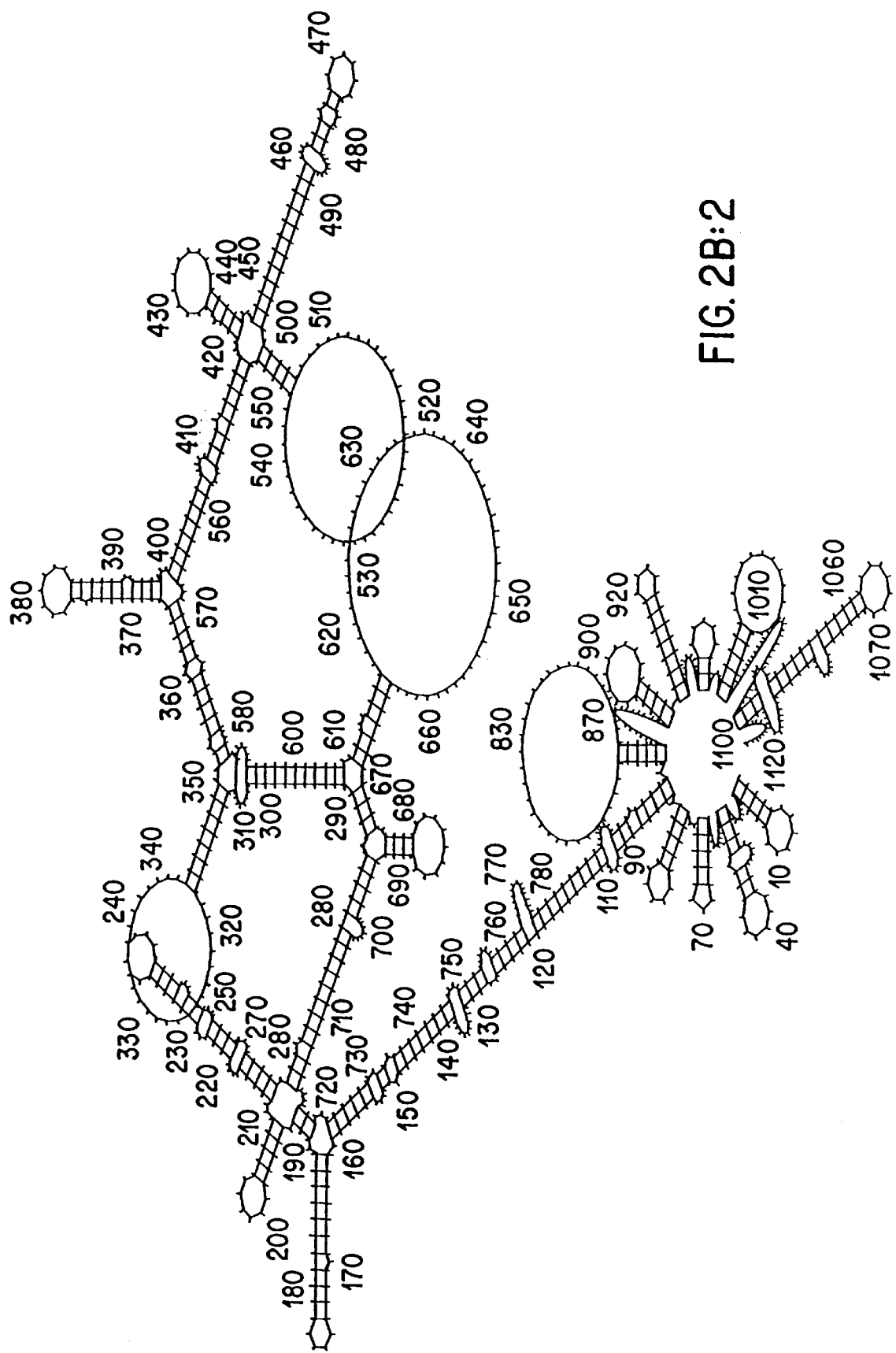
FIG. 2B:2

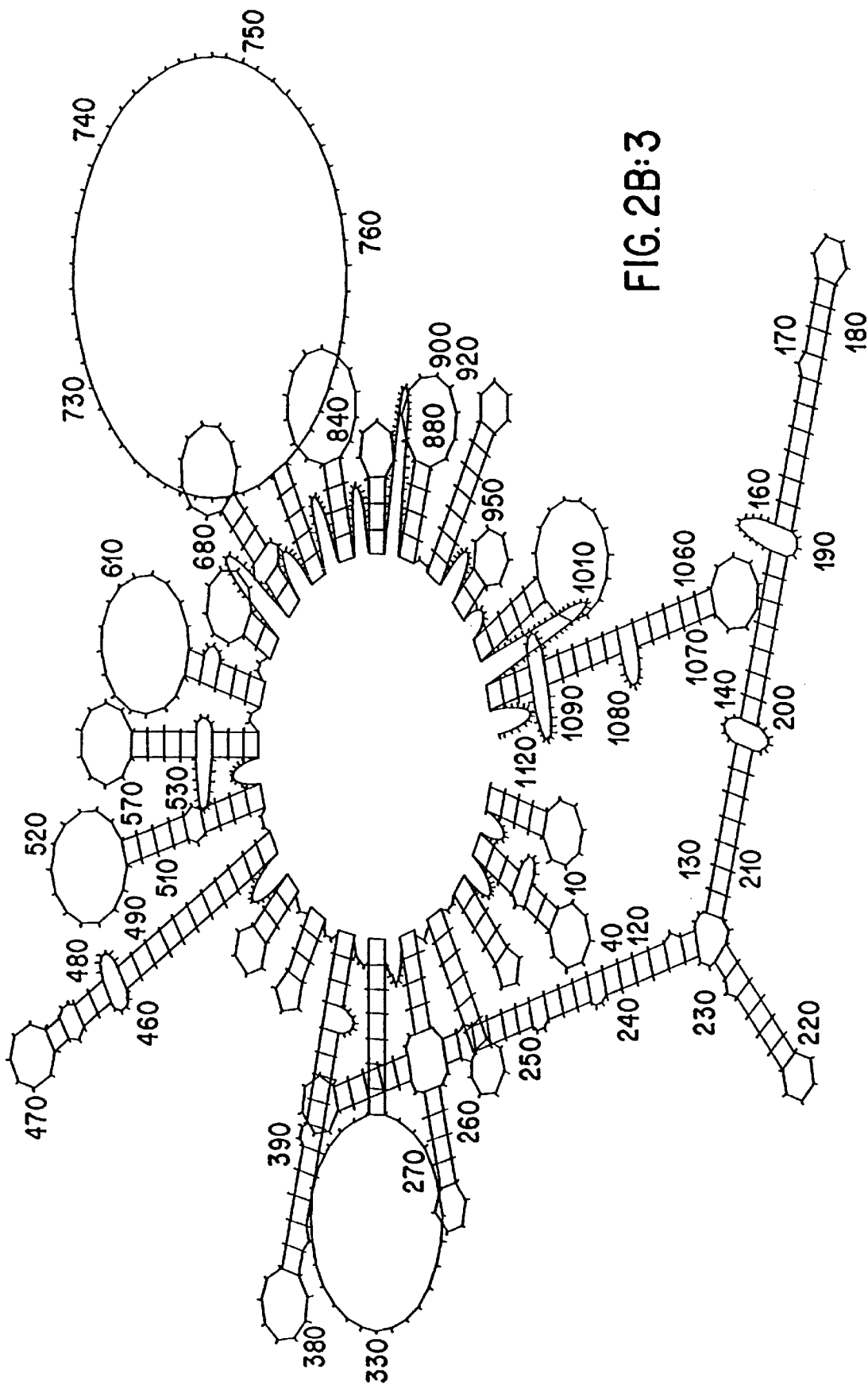
FIG. 2B:3

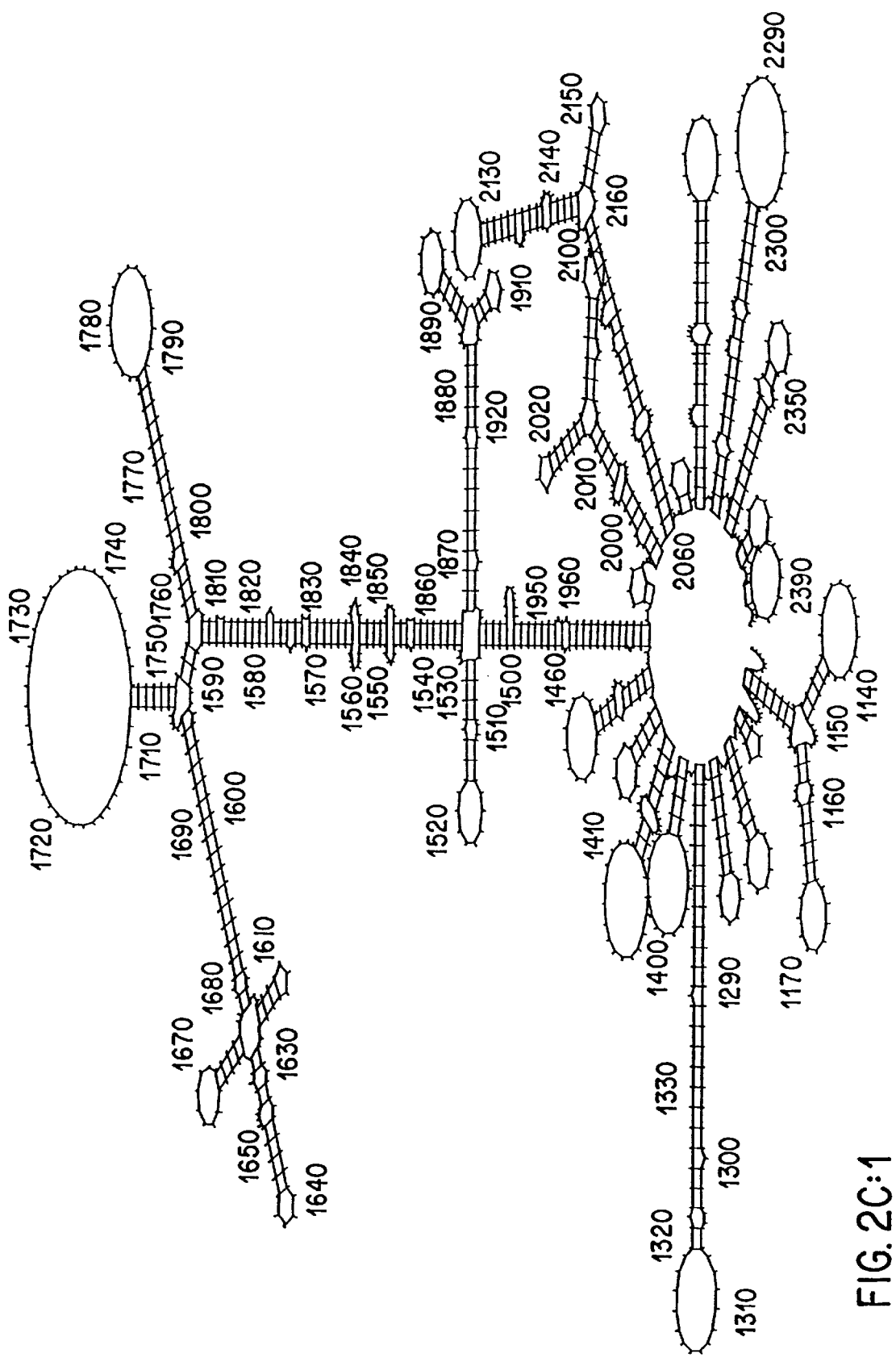
FIG. 2C:1

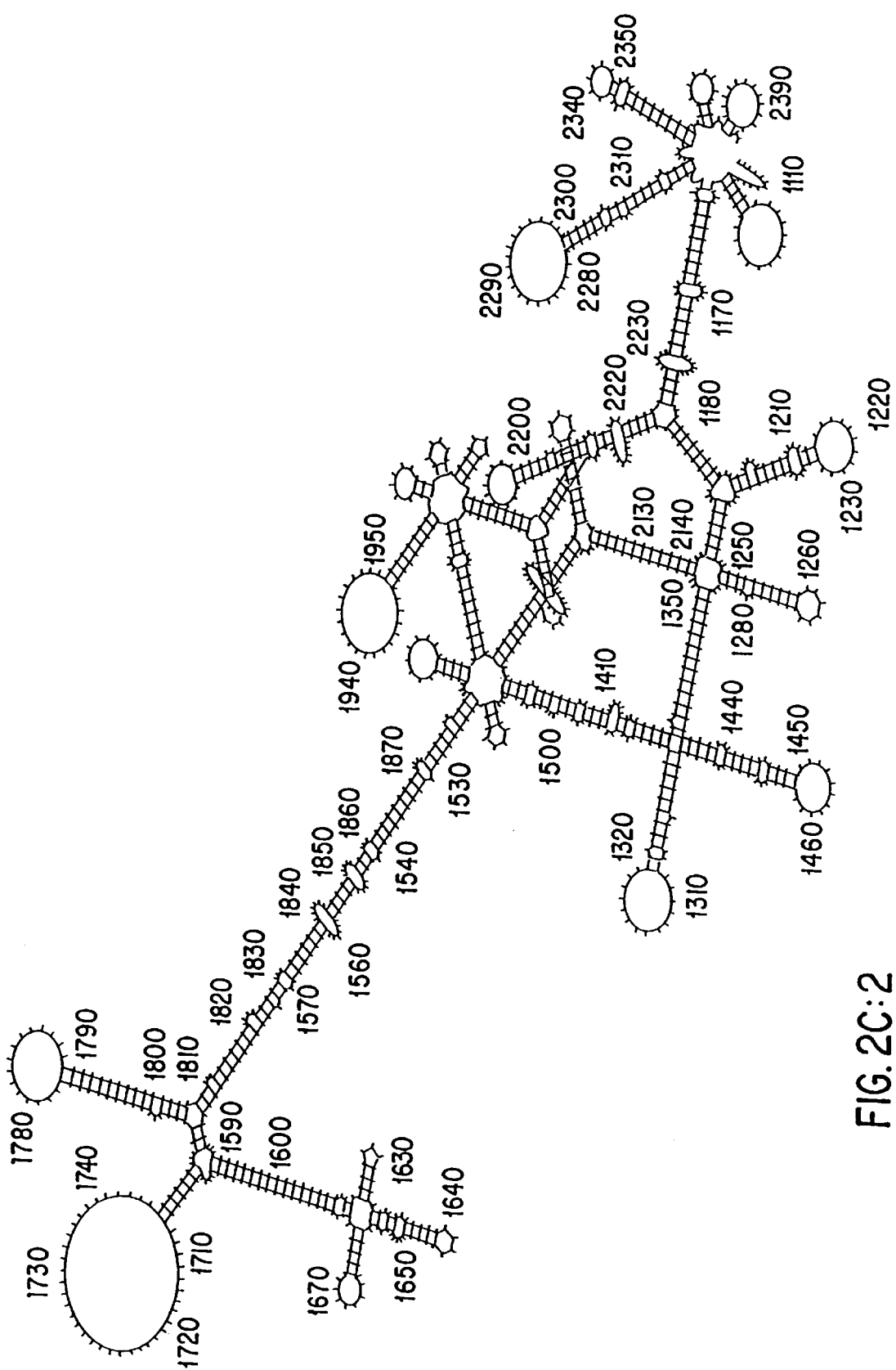
FIG. 2C:2

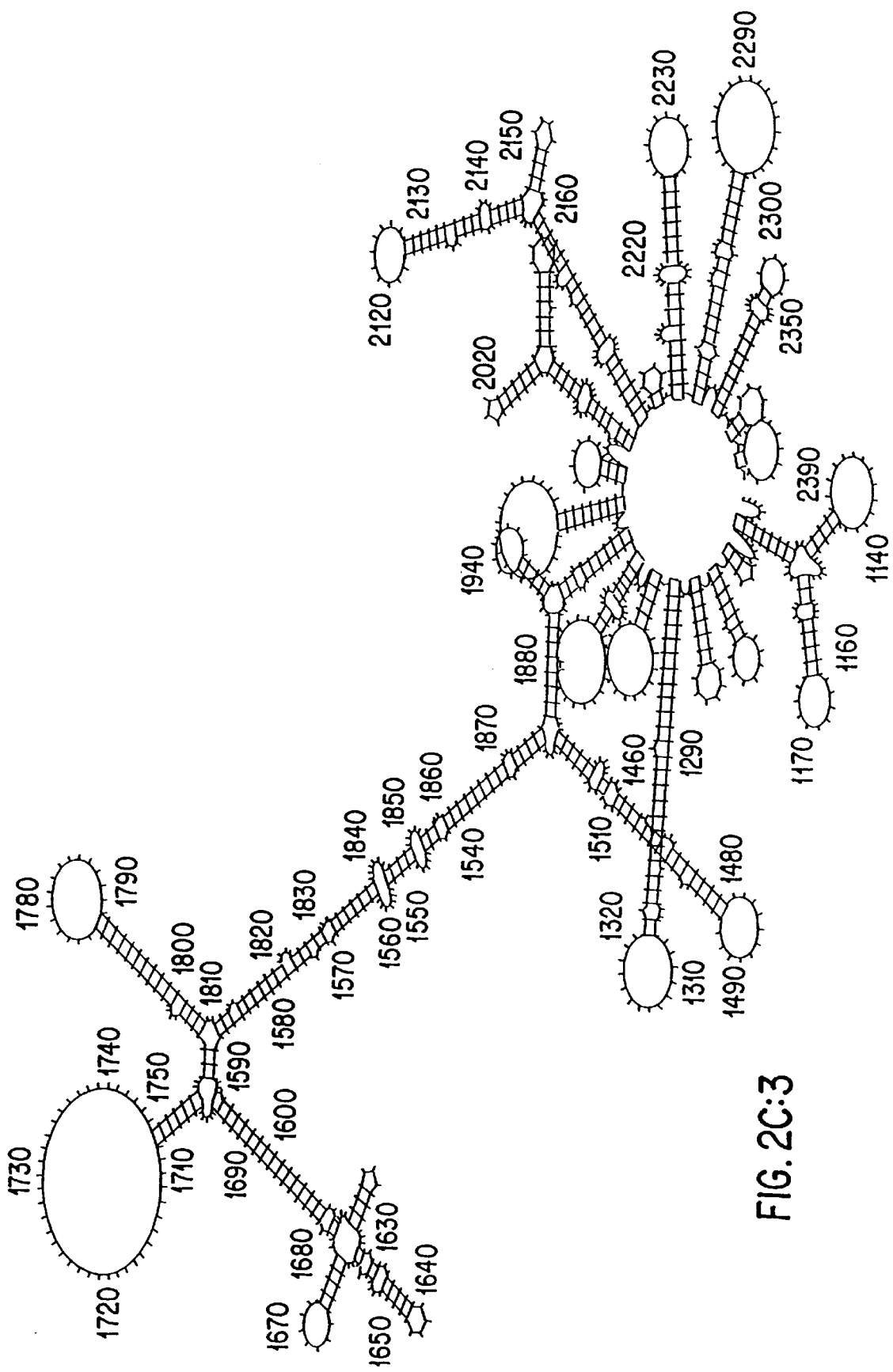
FIG. 2C:3

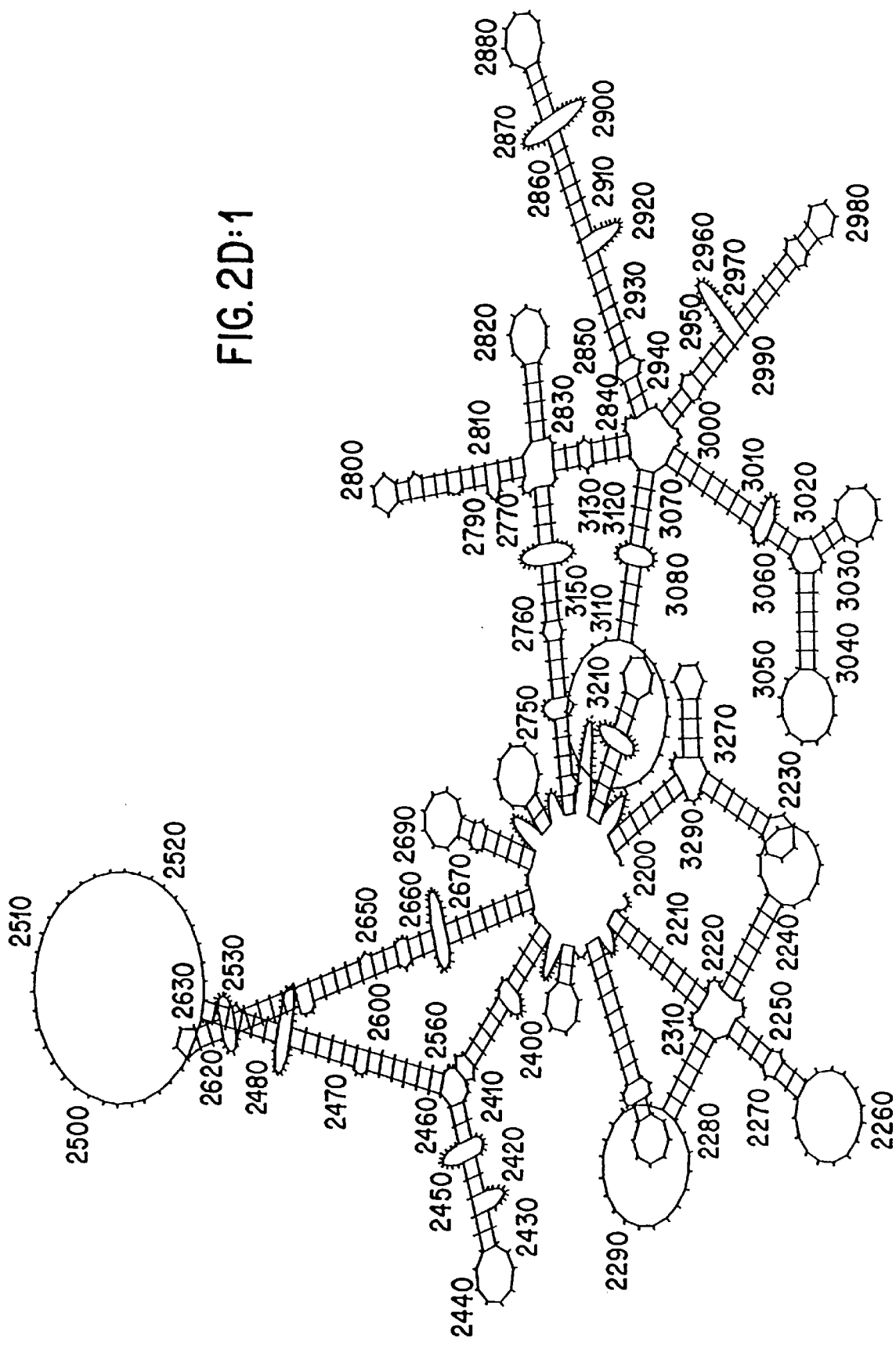
FIG. 2D:1

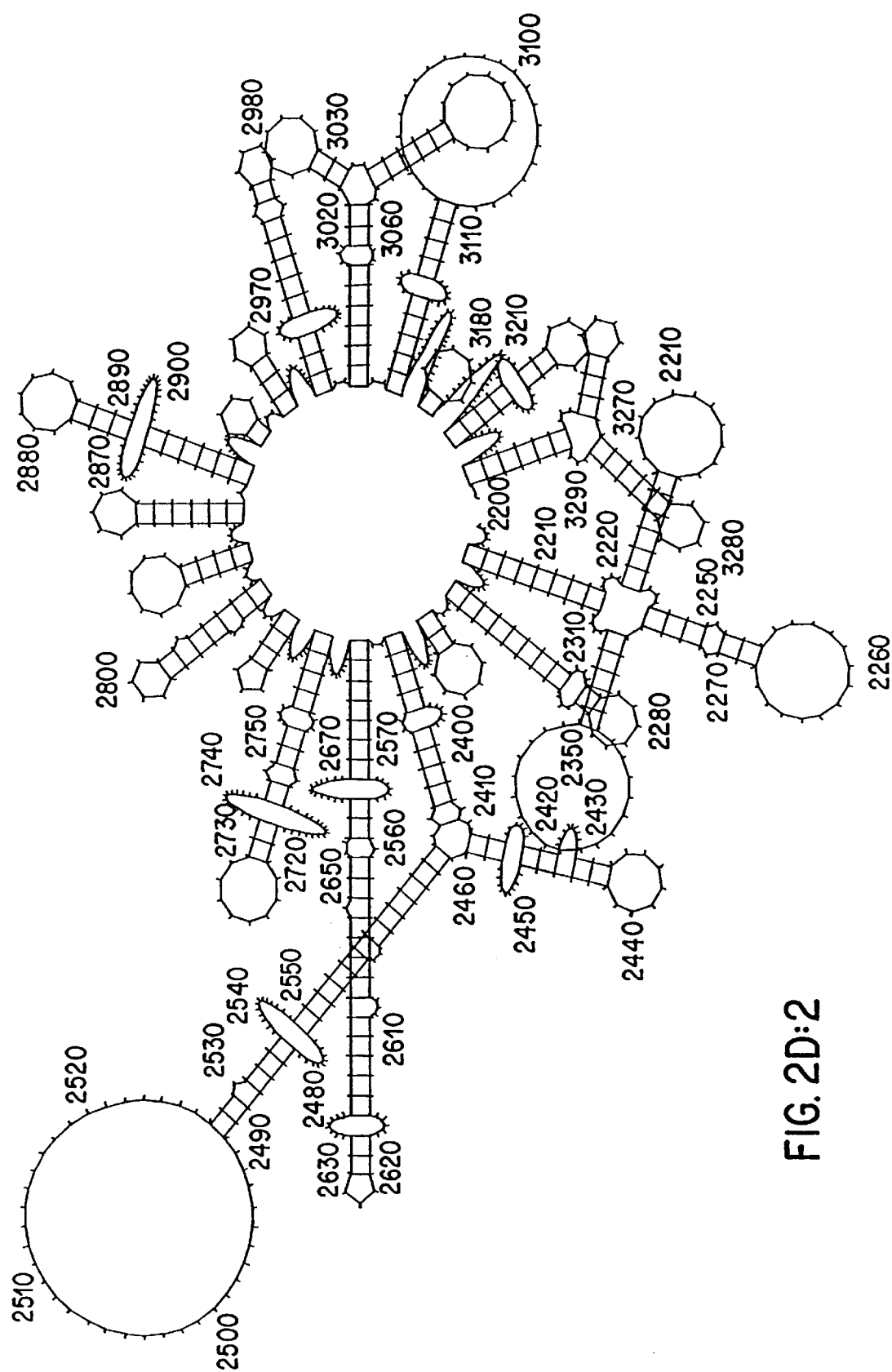
FIG. 2D:2

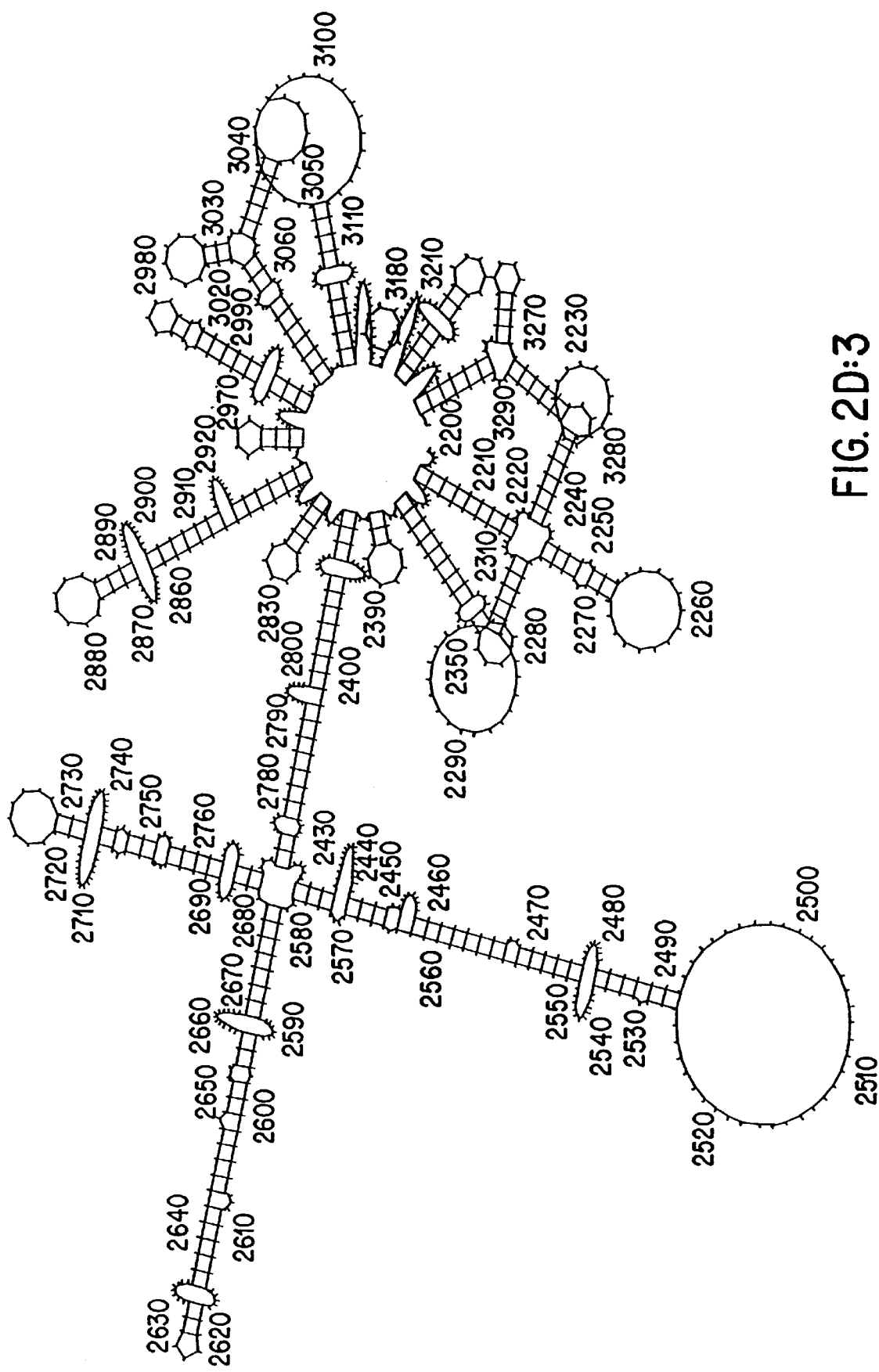
FIG. 2D:3

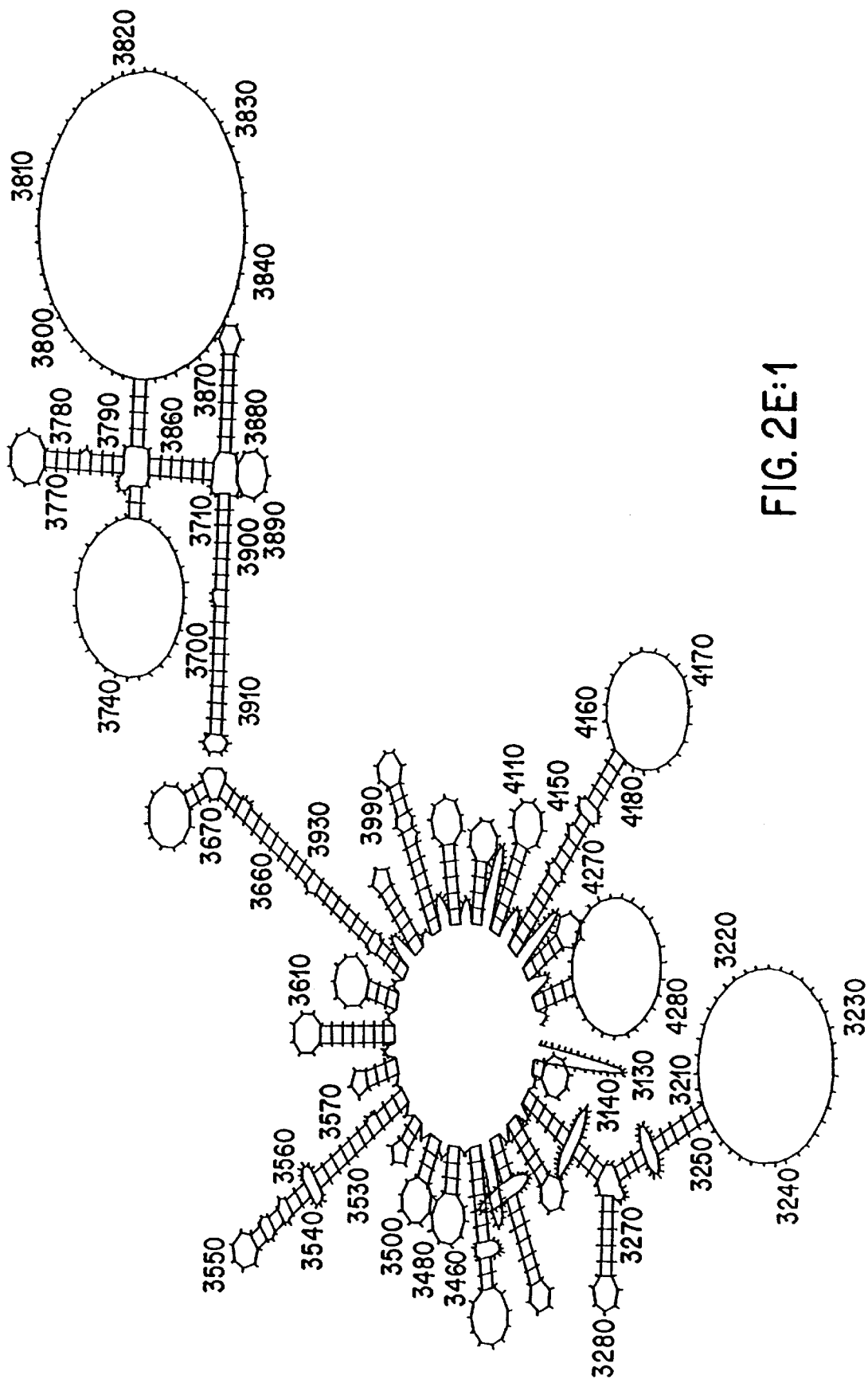
FIG. 2E:1

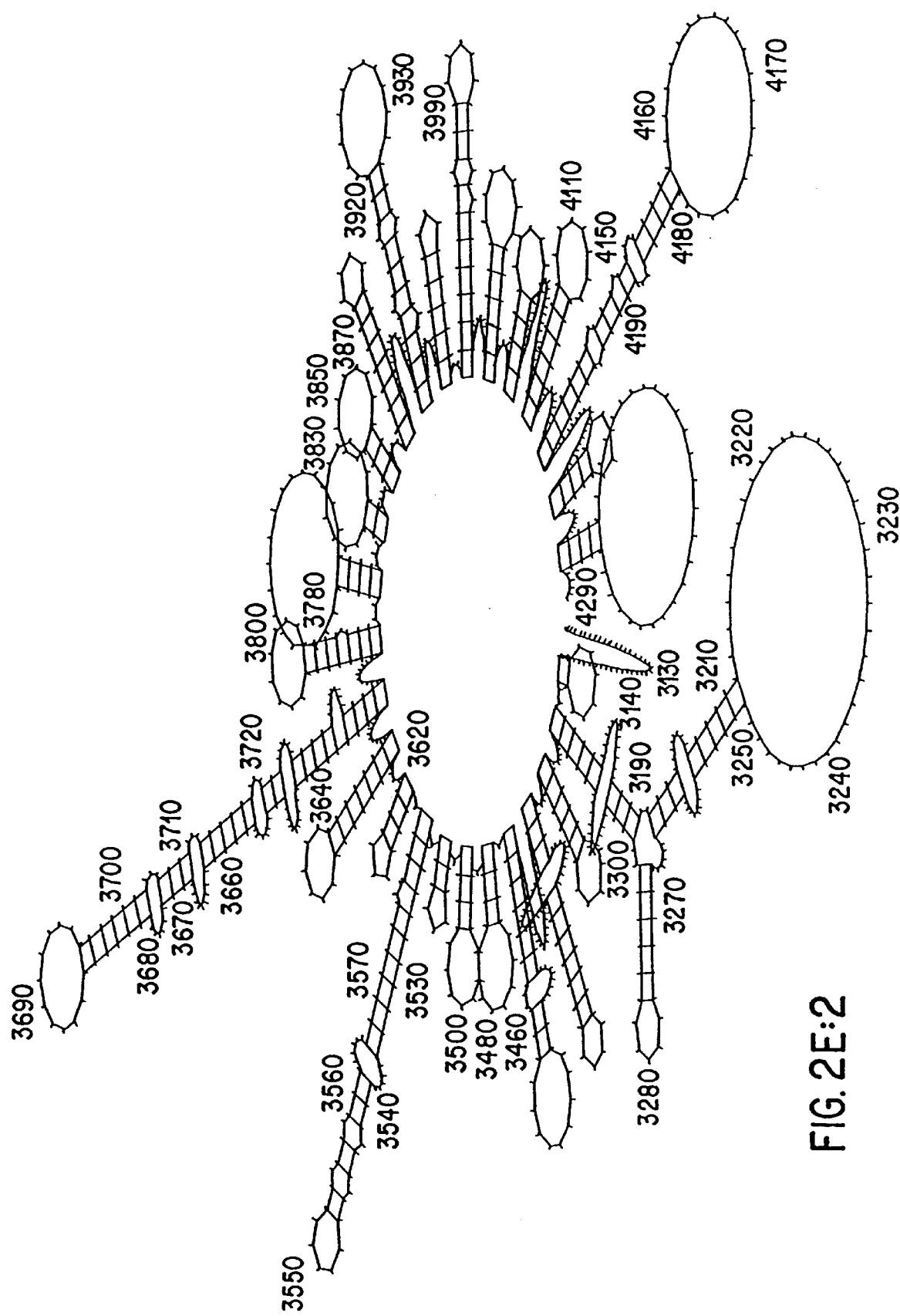
FIG. 2E:2

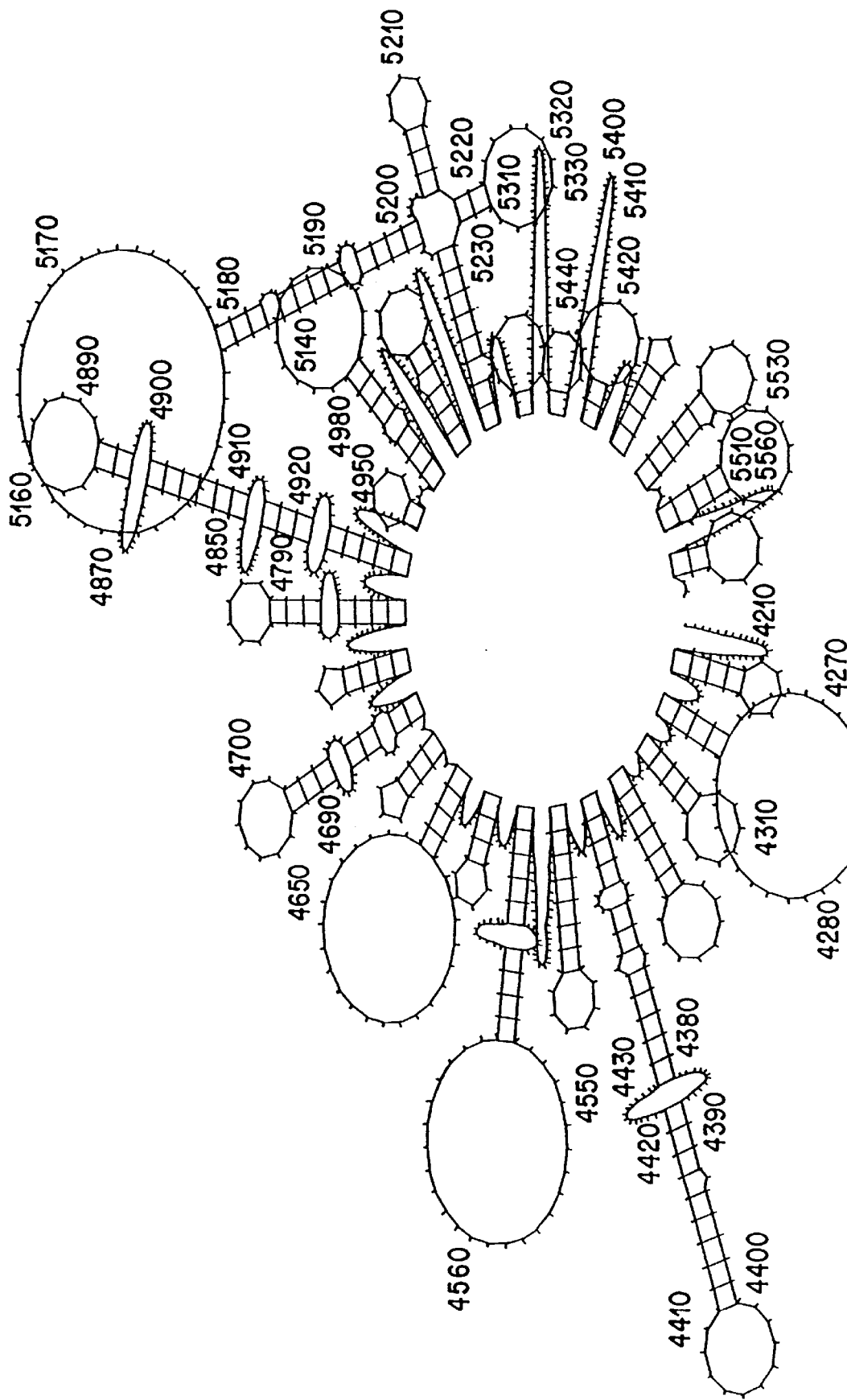
FIG.2F:1

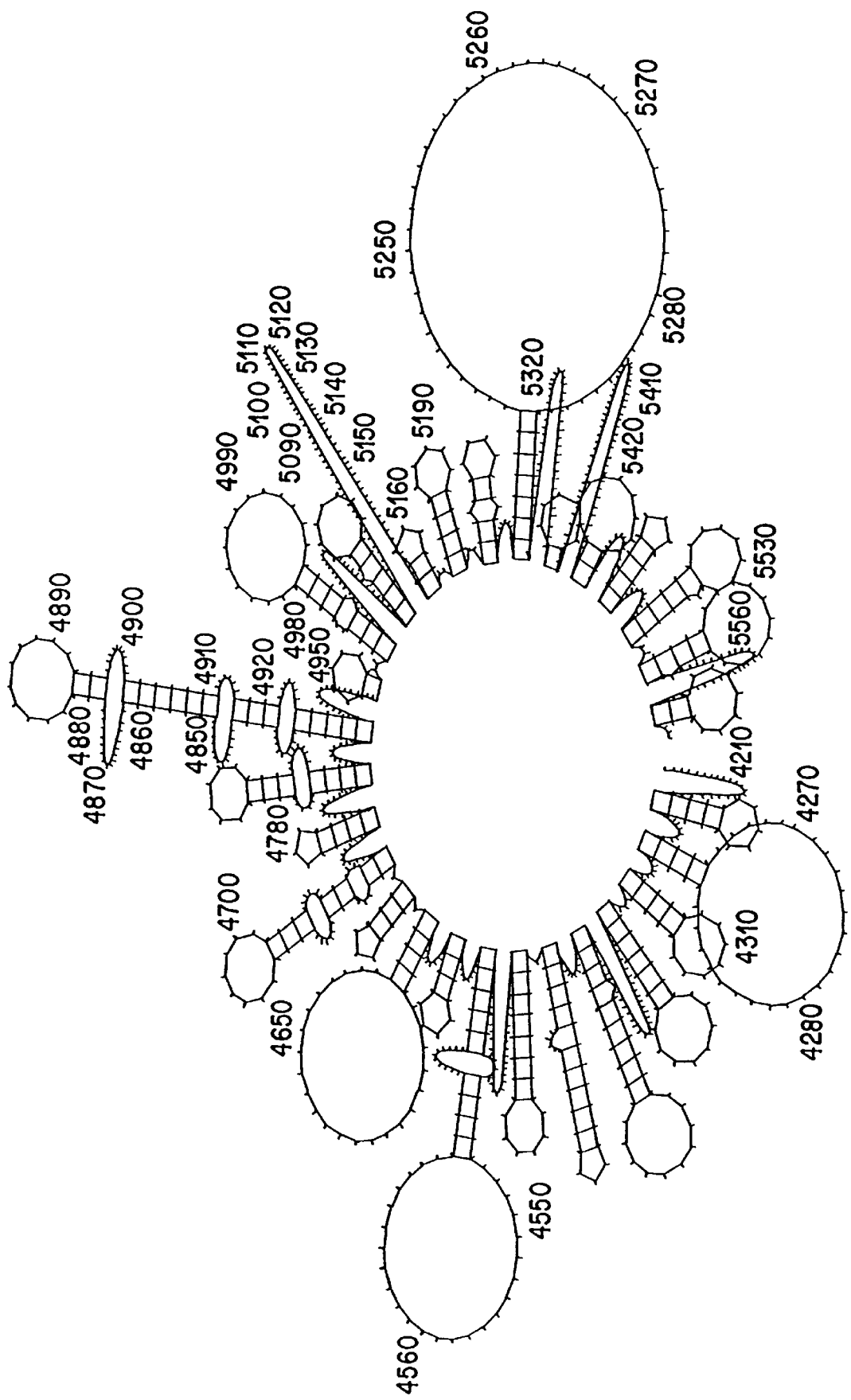
FIG.2F:2

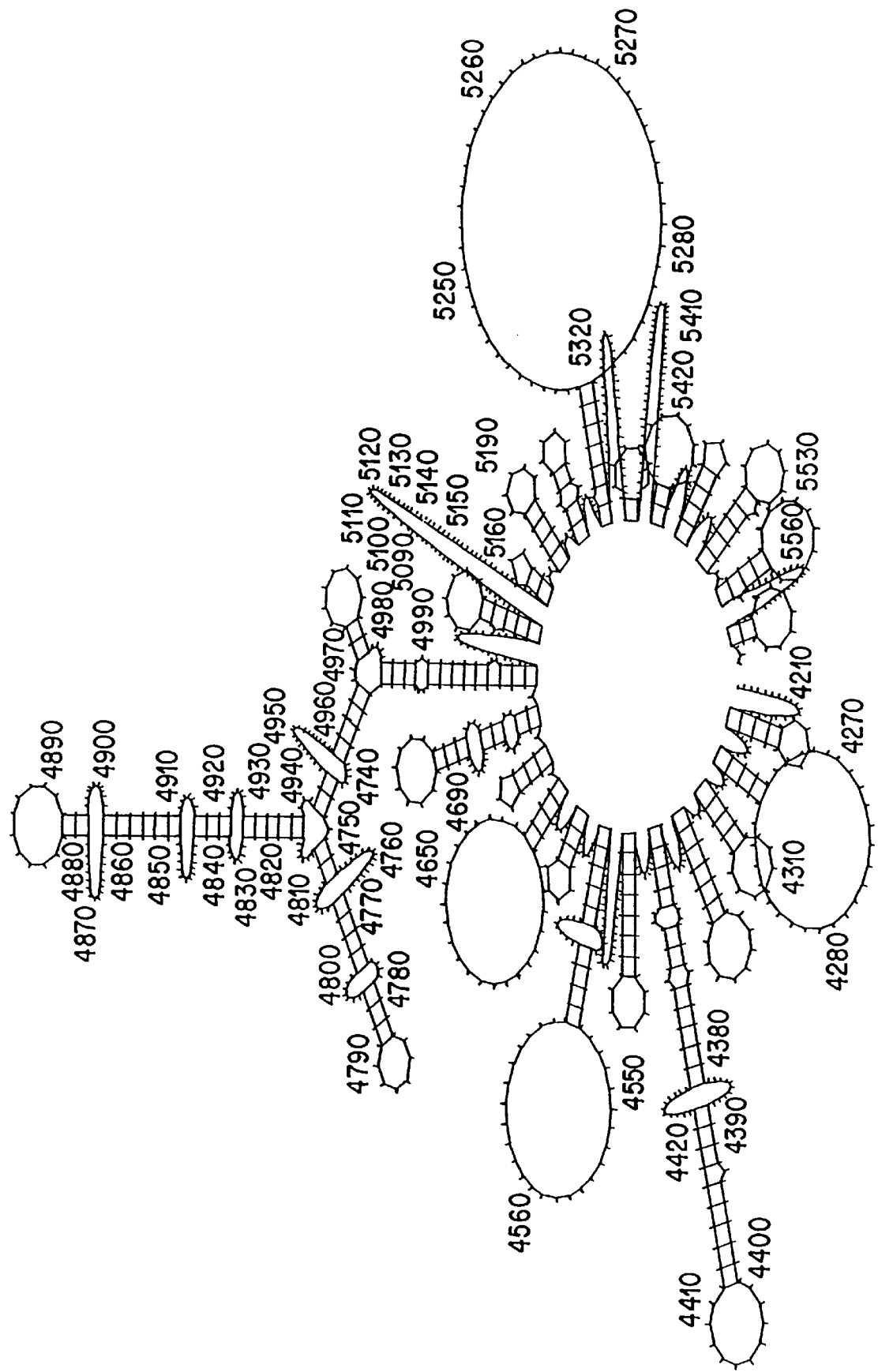
FIG.2F:3

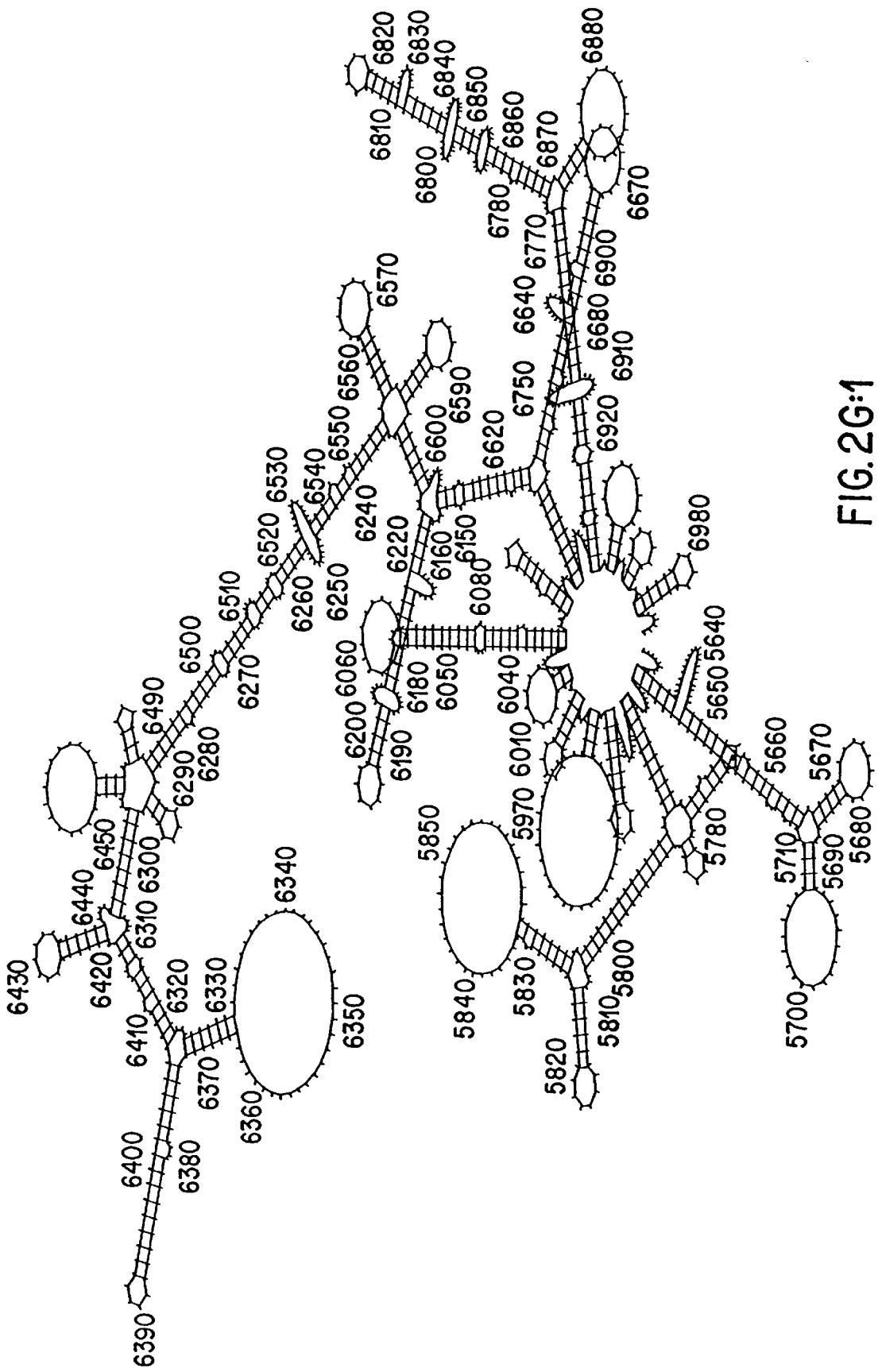
FIG. 2G:1

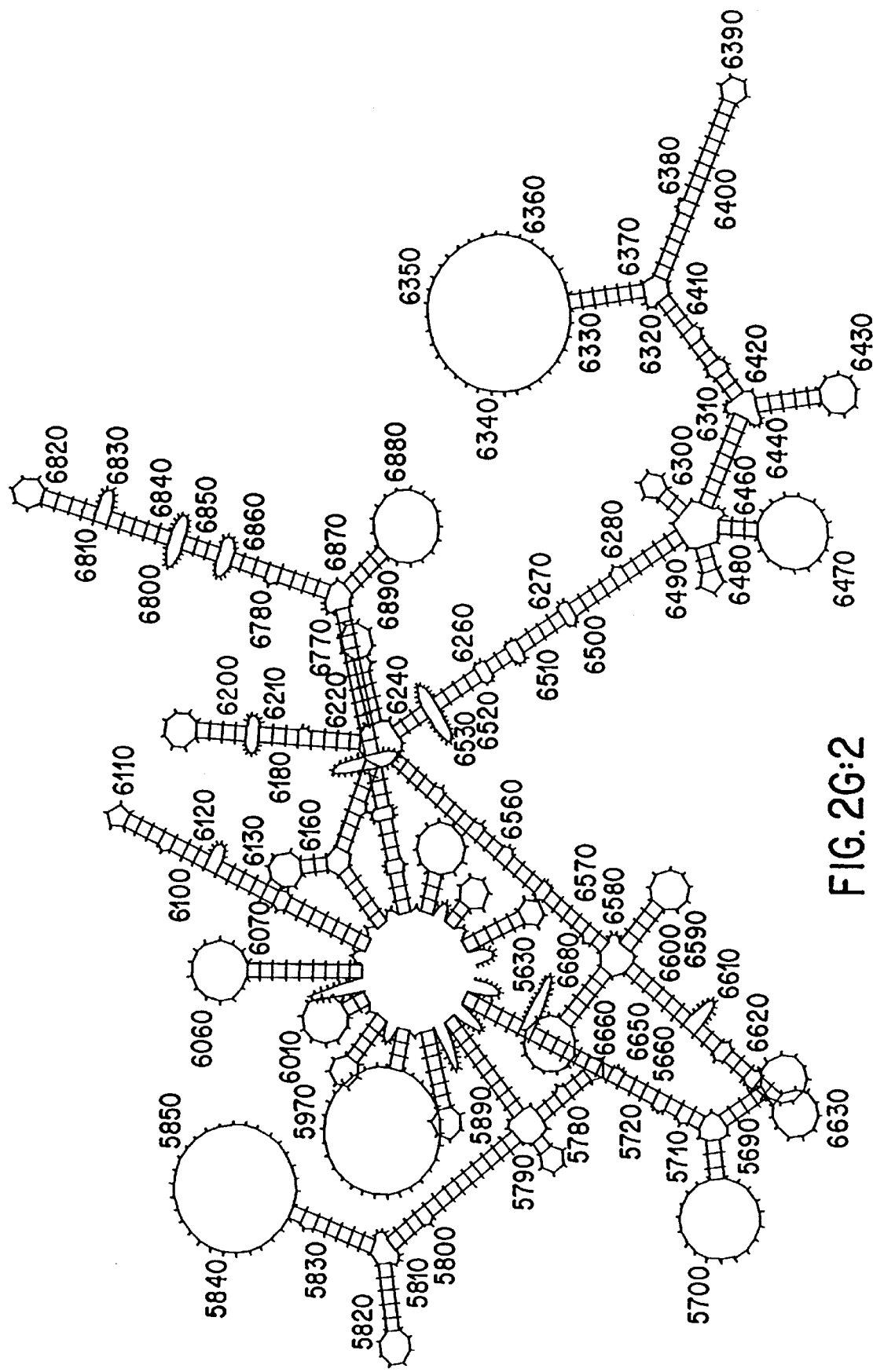
FIG. 2G:2

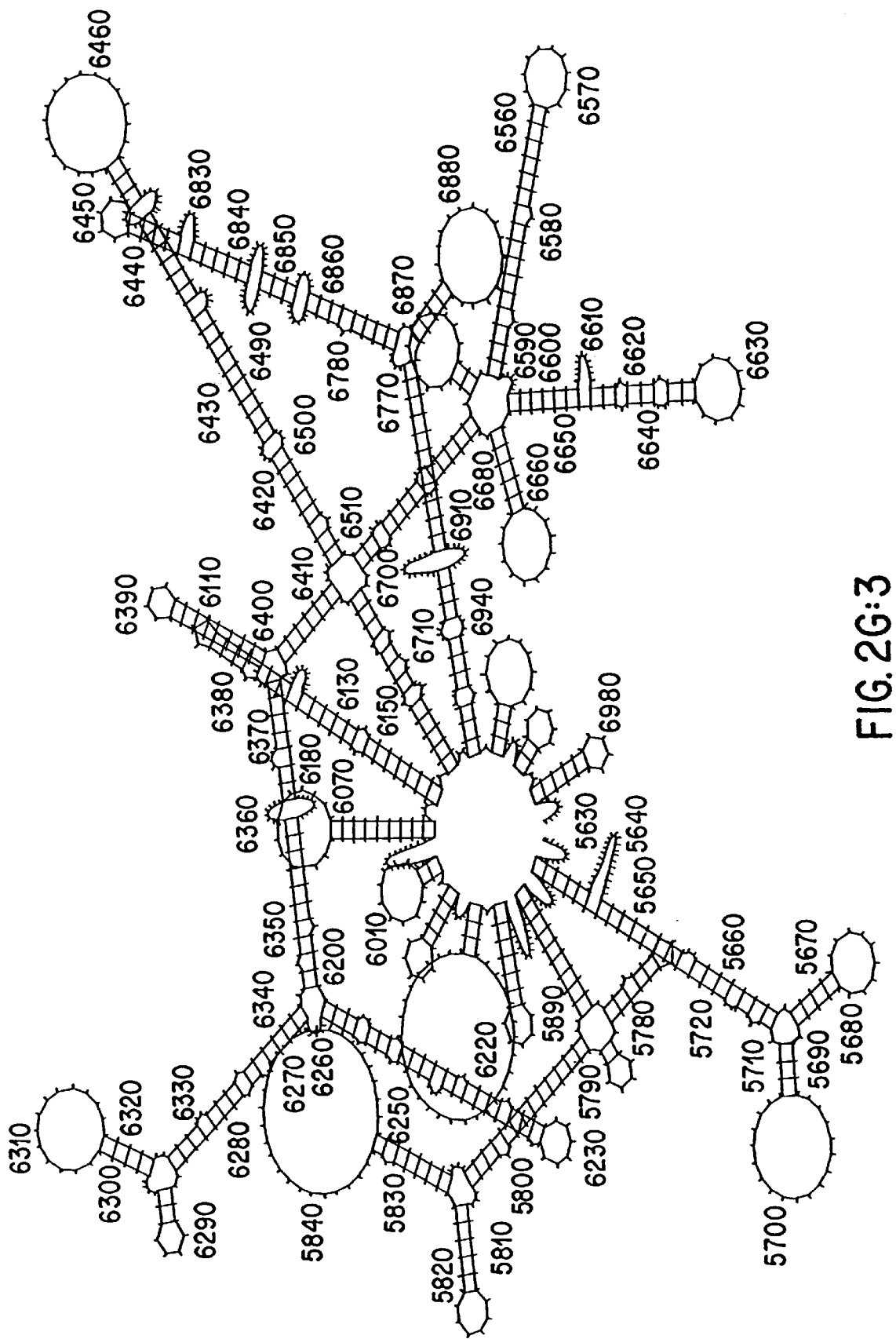
FIG. 2G:3

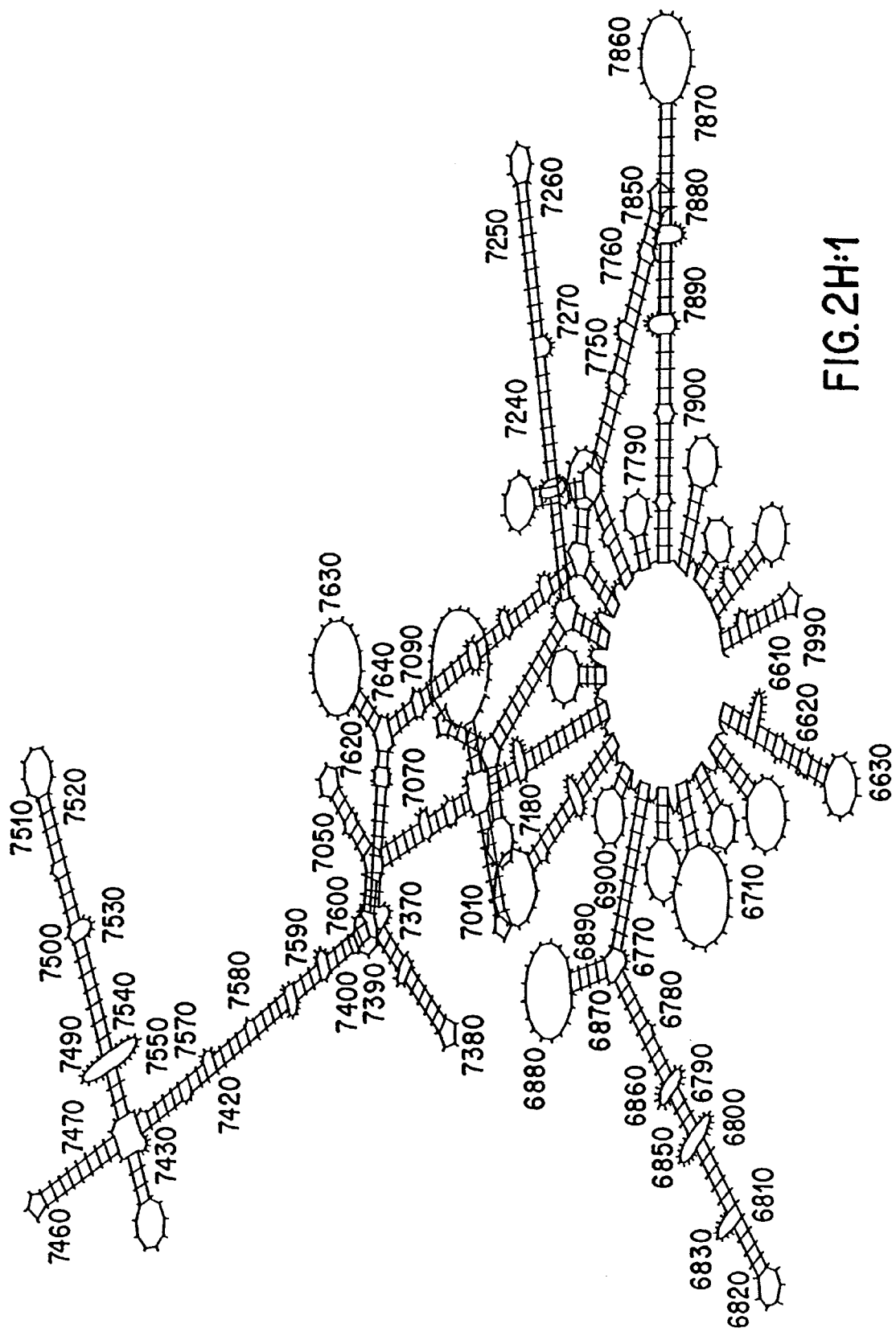
FIG.2H:1

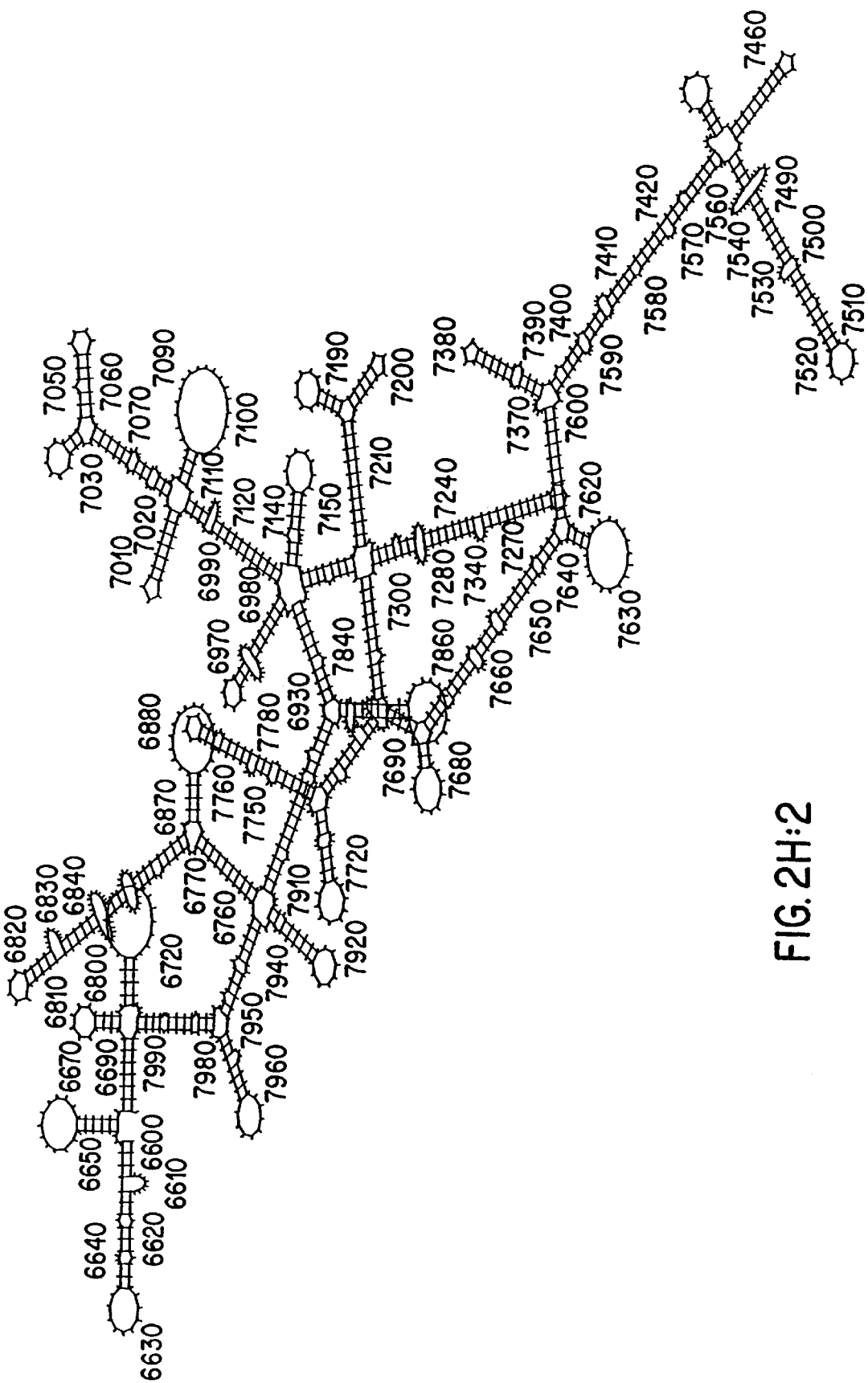
FIG. 2H:2

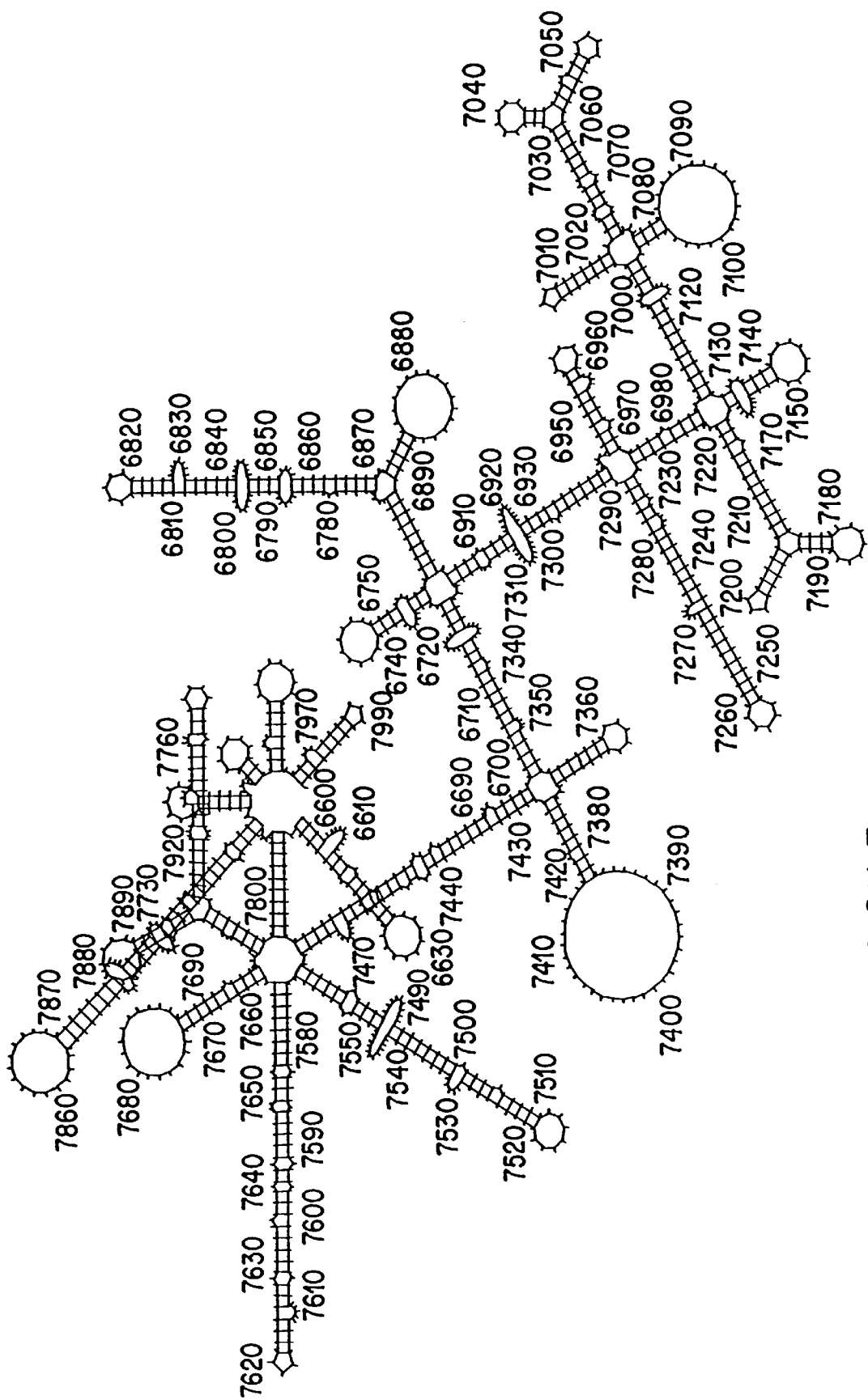
FIG.2H:3

US 6,214,805 B1

RNASE L ACTIVATORS AND ANTISENSE OLIGONUCLEOTIDES EFFECTIVE TO TREAT RSV INFECTIONS

This application is a continuation-in-part of U.S. application Ser. No. 08/801,898, filed Feb. 14, 1997, now U.S. Pat. No. 5,998,602, which claims benefit of U.S. provisional application Serial No. 60/011,725, filed Feb. 15, 1996, each of which is incorporated herein by reference in its entirety.

1. INTRODUCTION

The present invention relates to a chimeric molecule comprising an oligonucleotide complementary to a region of the genome of a negative strand RNA virus attached to an activator of RNase L ("activator-antisense complexes") to specifically cleave a genomic strand, antigenomic strand or mRNAs of the RNA virus. The present invention relates to compounds useful for treating humans infected by RNA viruses, such as Respiratory Syncytial Virus (RSV), and methods of their use. Particularly, the invention relates to a complex of an oligonucleotide that is complementary to some portion of the genomic strand, antigenomic strand or mRNAs of RSV and a covalently linked activator of RNase L (henceforth, "activator-antisense complexes"). More particularly, the invention relates to activator-antisense complexes, in which the oligonucleotide is selected to bind to regions of the RSV RNA genome that possess repeated or consensus sequences. The invention further relates to activator-antisense complexes, in which the oligonucleotide is selected to bind to a portion of the RNA genome that normally has no self-hybridizing secondary structure.

2. BACKGROUND TO THE INVENTION

Negative-strand RNA viruses may be divided into two categories, the nonsegmented RNA viruses, including Rhabdoviridae, Filoviridae and Paramyxoviridae, and the segmented RNA viruses, including Orthomyxoviridae, Bunyaviridae and Arenaviridae. These families of RNA viruses include the following important pathogens: parainfluenza viruses, mumps virus, measles, respiratory syncytial virus, vesicular stomatitis virus, rabies, and influenza virus, etc. These viruses share many similarities in genomic organization and structure. The genomes of negative strand RNA viruses consist of single-stranded RNA of negative polarity. The genomic RNA must be transcribed into mRNA to direct the synthesis of viral proteins in the host cell. The viral RNA-dependent RNA polymerase controls transcription and replication of the RNA genome, thus no DNA of viral origin is involved in viral replication.

Respiratory syncytial virus (RSV), a non-segmented, negative-strand RNA virus in the pneumovirus subfamily of Paramyxoviridae, is a widespread human pathogen accounting for over 1 million deaths per year worldwide (McIntosh and Chanock, 1990, in Virology, 2nd edition. Raven Press, Ltd. NY 1045–1072). While the majority of serious cases are children from developing countries, there are estimated to be 300,000 hospitalized cases per year in the United States (Zisson, 1993, Shamen Pharmaceuticals, Inc. Company Report). It is also believed that of childhood deaths from pneumonia caused by respiratory viral infections, 62% are due to RSV (Heilman, 1994 RFA: "Mechanism of RSV Vaccine Immunopotentiation" N.I.A.I.D., Bethesda, Md.).

Similar to other negative-strand RNA viruses, the RSV genomic RNA is transcribed and translated into specific mRNAs that are translated into viral proteins required for virus reproduction followed by replication of the genome. Such replication provides additional templates for transcription as well as genomic RNA for progeny virus (Collins et al. 1996 in Fields Virology, eds. Lippincott, Philadelphia, 3rd edition p. 1313–1351). The single stranded RNA genome of RSV codes for ten virus-specific proteins. The negative stranded genome is packaged in a nucleocapsid and is surrounded by a lipid envelope containing two glycoproteins. One is the fusion protein which facilitates entry of RSV into cells through host membrane and viral membrane fusion.

The approved treatment for RSV is aerosolized ribavirin (1-b-D-ribofuranosyl-1,2,3-triazole-3-carboxamide). Ribavirin is administered as an aerosol which is inhaled. Ribavirin therapy has several limitations including minimal efficacy in clinical use, the requirement of a tent around the patient, the potential to clog ventilating units, and the observation of some teratogenicity in animal models (Froelich, 1994 SPI Pharmaceuticals, Inc. Company Report, Pershing Division), significant side effects and high cost. Recently, another treatment has been approved for the treatment for RSV, RESPIGAM, a polyclonal antibody administered by injection.

RSV replicates in several alveolar cell types including macrophage and epithelial lineages (Panuska et al., 1992, Am. Rev. Resp. Dis. 145: 934–939). Accordingly, ribavirin is administered to RSV infected individuals by inhalation of an aerosol (Taber et al., 1983, Pediatrics 72:613–18; Hall et al., 1983, N. Eng. J. Med. 308:1443–7; Englund et al., 1994, J. Pediatrics 125:635–41.)

Activator-antisense complexes (termed therein "2-5A:AS") have been described previously (Torrence et al., 1993, WO 94/09129 by Torrence et al.). Although antisense oligonucleotides have been used as antiviral agents, e.g.: to inhibit HIV replication, see Zamecnik et al.; 1986; Goodchild et al., 1988; Letsinger et al., 1989; Balotta et al., 1993; to inhibit RSV infection, WO95/22553 by Kilkuskie et al., no examples of the successful use of activator-antisense complexes as an antiviral therapy have been reported.

The mechanism of action of activator-antisense complexes is different than the mechanism of action of other antisense oligonucleotides. The activator portion of the activator-antisense complexes activates RNase L and the antisense domain serves as a specific, high affinity binding site for the target RNA. The result is the selective cleavage of the target RNA by RNase L.

Physiologically, RNase L functions as part of the interferon system in restricting virus replication in cells of higher vertebrates (reviewed in Silverman, 1994). Interferon treatment of cells activates genes encoding 2-5A synthetases, double-stranded RNA (dsRNA)-dependent enzymes that produce 5'-triphosphorylated, 2',5'-linked oligoadenylates (2',5'A) from ATP. Viral dsRNAs are potential activators of these enzymes (Gribaudo et al., 1991). The 2',5'A binds to and activates RNase L resulting in the general cleavage of cellular and viral RNA; thus restricting the replication of some picornaviruses (Chebath et al., 1987; Rysiecki et al., 1989; and Hassel et al., 1994).

RNase L is not specific for cleaving viral RNA. For instance, in interferon-treated, encephalomyocarditis virus infected cells, RNase L causes degradation of ribosomal RNA (Wreschner et al., 1981, Nature 289: 414–417). Through the activator-antisense approach, RNase L is converted from a non-specific nuclease to a highly specific endoribonuclease that selectively cleaves mRNA targets. This has been demonstrated in a cell-free system from Daudi cells, a human lymphoblastoid cell line, in which a modified HIV-1 vif mRNA was targeted for cleavage by an activator-antisense complex (Torrence et al., 1993, Proc. Natl. Acad. Sci. 90:1300–1304). Subsequently, purified RNase L has been directed by an activator-antisense complex to cleave selectively an mRNA target encoding the protein kinase PKR in the presence of a nontargeted mRNA (Maran et al., 1994, Science 265: 789–792). Furthermore, in HeLa cells, the use of activator-antisense complexes, which were directed to a sequence in PKR mRNA, resulted in the ablation of PKR mRNA and enzyme activity (Maran et al., 1994, Science 265: 789–792) such that the dsRNA-mediated activation of transcription factor, NF-κB was ablated. More recently, it was shown that the activation of RNase L by an activator-antisense complex results in the catalytic degradation of PKR mRNA ($k_{cat}$ of about 7 $sec^{-1}$) (Maitra et al., 1995 J. Biol. Chem. 270: 15071–15075).

3. SUMMARY OF THE INVENTION

The present invention relates to chimeric molecules comprising an oligonucleotide complementary to a region of the RNA genome, the RNA antigenome or mRNAs of a negative strand RNA virus attached to an activator of RNase L ("activator-antisense complexes") which specifically cleave a genomic or antigenomic strand of the RNA virus.

The present invention relates to methods of inhibiting infection of a negative strand RNA virus with activator-antisense complexes targeted to the RNA genome of the RNA virus. In particular, the invention relates to a complex of an oligonucleotide that is complementary to some portion of the genomic or antigenomic strand of an RNA virus, such as RSV, coupled to an activator of RNase L.

In a preferred embodiment, the present invention relates to a complex that is useful for the treatment of infection by a negative strand RNA virus, in particular infection by RSV. The invention relates to a complex of an activator of RNase L coupled to an oligonucleotide complementary to a region of the virus RNA genome characterized by repeated or consensus sequences. In particular, the oligonucleotide component of the complex has a sequence of approximately 17 nucleotides complementary to a number of repeated or consensus sequences that occur within the critical gene-end-intragenic-gene-start signals of the virus RNA genome.

In another embodiment, the present invention relates to a complex of an oligonucleotide complementary to a region of the virus RNA antigenome or mRNA coupled to an activator of RNase L. The essential components of the complex are an antisense oligonucleotide which has a sequence that is complementary to between about 10 and about 30 nucleotides of the antigenomic RNA strand, i.e., the template strand for genome synthesis, of a strain of RSV and an activator of RNase L (henceforth, "activator-antisense complexes"). In a further alternative embodiment the invention consists of an antisense oligonucleotide having a sequence of at least 10–30 nucleotides and preferably 15–25 nucleotides, and more preferably which is 17, 18 or 19 nucleotides. The elements of the activator-antisense complex are preferably covalently linked by a linker.

In a preferred embodiment, but not by way of limitation, the activator-antisense complexes of the invention are transported across the cell membrane without the use of carriers or permeabilizing agents. Once internalized the activator-antisense complexes lead to the formation of enzyme-antisense complexes, which causes destruction of the antisense targeted RNA. To treat RSV infection the antisense complexes can be administered by inhalation of an aerosol, the same method as is used to administer ribavirin. Ribavirin and the antisense complexes of the invention can, therefore, be administered in a common pharmaceutical composition.

4. BRIEF DESCRIPTION OF THE FIGURES

FIGS. 1A–1H. The sequence of Respiratory Syncytial Virus strain A2, positions numbered in the 5'→3' direction (SEQ ID NO:12).

FIGS. 2A–2H:3. Squiggle plot output of MFOLD calculations of the secondary structure of portions of the RSV antigenomic RNA, positions numbered in 5'→3' order. FIG. 2A. Squiggle plot of residues 7900–8800 of RSV antigenomic RNA. FIGS. 2B:1–2B:3. Three alternative squiggle plots of residues 1–1124 of RSV antigenomic RNA. FIGS. 2C:1–2C:3. Three alternative squiggle plots of residues 1100–2400 of RSV. FIGS. 2D:1–2D:3. Three alternative squiggle plots of residues 2200–3300 of RSV antigenomic RNA. FIGS. 2E:1–2E:2. Two alternative squiggle plots of residues 3100–4300 of RSV antigenomic RNA. FIGS. 2F:1–2F:3. Three alternative squiggle plots of residues 4200–5599 of RSV. FIGS. 2G:1–2G:3. Three alternative squiggle plots of residues 5600–6999 of RSV antigenomic RNA. FIGS. 2H:1–2H:3. Three alternative squiggle plots of residues 6600–7999 of RSV antigenomic RNA.

Figure 3:
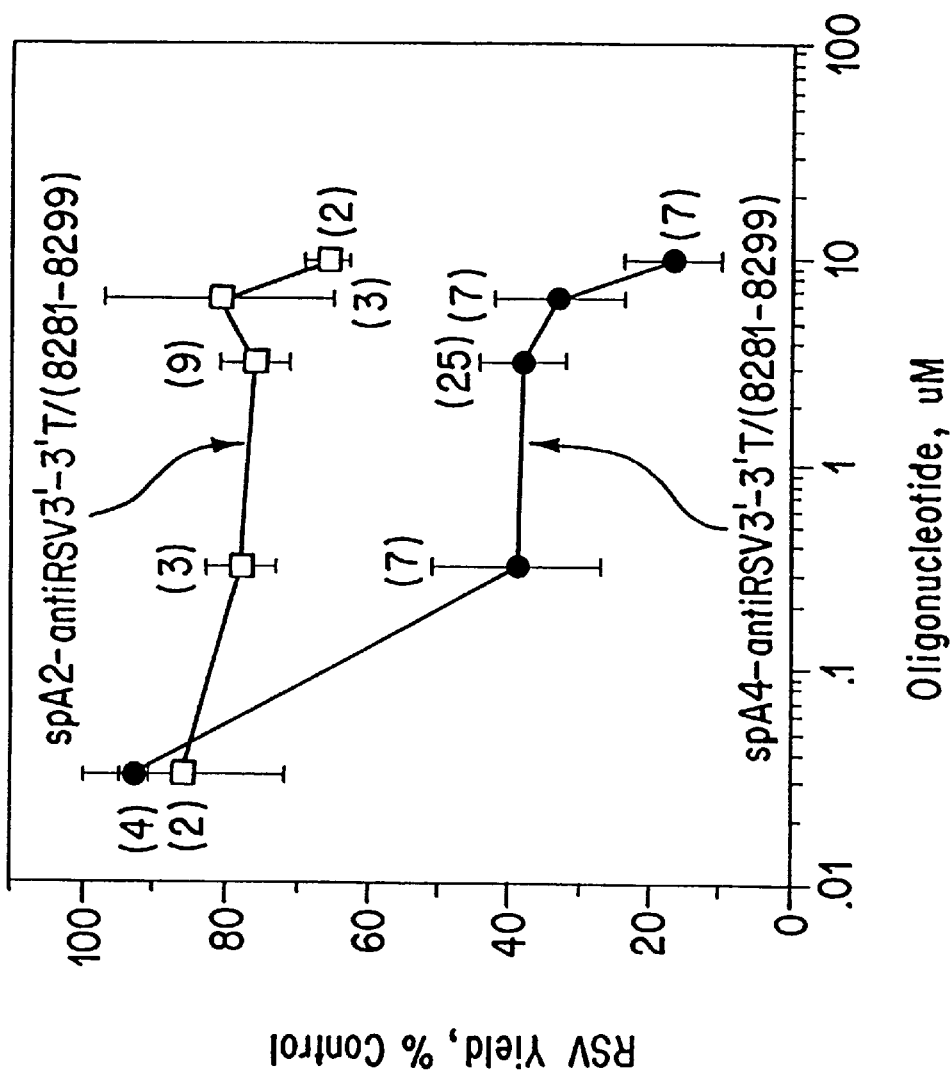

FIG. 3. Comparison of anti-RSV activities of $spA_4$-antiRSV3'-3'T/(8281–8299) and $spA_2$-antiRSV3'-3'T/(8281–8299).

5. DETAILED DESCRIPTION OF THE INVENTION

The present invention relates to methods of inhibiting infection by RNA viruses with complexes of an activator of RNase L and an oligonucleotide that is capable of binding to the genome, antigenome or mRNAs of a negative strand RNA virus to specifically cleave the genomic, antigenomic RNA strand or mRNAs of the virus.

The present invention relates to a covalently-linked complex of an activator of RNase L and an oligonucleotide that is capable of binding to the genomic RNA strand of an RNA virus and/or binding to the antigenomic or mRNA of the negative strand RNA virus. In accordance with the present invention, the methods and complexes of the invention may be applied to target any negative strand RNA virus, including, but not limited to, parainfluenza virus, mumps virus, rabies, and influenza virus. The invention in one embodiment relates to a complex of an oligonucleotide that is capable of binding to the genomic or antigenomic template RNA strand of a negative strand RNA virus and/or binding to an mRNA of a viral protein (an "antisense oligonucleotide") coupled to an activator of RNase L. In accordance with the present invention, the complex of the antisense oligonucleotide and the activator of RNase L may be covalently or non-covalently linked.

In a preferred embodiment of the present invention, the oligonucleotide component of the complex is complementary to a region of the viral genomic RNA strand characterized by repeated or consensus sequences. In particular, the oligonucleotide component of the complex has a sequence of approximately 17 nucleotides complementary to a number of repeated or conserved sequences that occur within the critical gene-end-intragenic-gene-start signals of the viral RNA genome.

In another embodiment of the present invention, the oligonucleotide component of the complex is complementary to a region of the virus RNA antigenome or mRNA which are characterized by an absence of self-hybridizing secondary structure. According to the invention, the portion of the antigenome targeted by the oligonucleotide component can be determined from the sequence of the RNA antigenome and secondary structure determining algorithms such as MFOLD. A suitable portion of the antigenome is one that is normally in a single stranded conformation, e.g., forms a loop of the stem and loop secondary structure of RNA. Since in some embodiments of the present invention the antisense activator complexes are designed to target antigenomic RNA, they are also complementary to the mRNA that directs translation of the viral proteins.

In a preferred embodiment the antisense oligonucleotide is complementary to a portion of the RSV genome or antigenome that is normally single stranded. The activator is attached through a linker to either the 3' or the 5' terminus of the antisense oligonucleotide by a linker. In one embodiment, a blocker is attached to the 3' terminus of antisense oligonucleotide and the linker is attached to the 5' terminus of the antisense oligonucleotide. In an alternative embodiment the linker is attached to the 3' end of the antisense oligonucleotide and serves as both linker and blocker. The antisense oligonucleotide is between about 15 and about 20 nucleotides in length and preferably 17, 18 or 19 nucleotides in length. Those skilled in the art will understand that oligonucleotides with high GC content can be shorter than those with low GC content.

The internucleotide phosphodiester bonds of the antisense oligonucleotide can be any bonds that are compatible with the formation of Watson-Crick base pairs with complementary RNA. These include as non-limiting examples phosphodiesters, phosphorothiodiesters, methylphosphonodiesters and methylphosphonothiodiesters, which provide for increased resistance to degradation after administration. The nucleotides of the antisense oligonucleotide can be 2'-deoxynucleotides or 2'O-methyl nucleotides.

5.1 DETERMINATION OF THE SEQUENCE OF THE ANTISENSE OLIGONUCLEOTIDE

The present invention relates to activator-antisense complexes designed to specifically target and cleave the RNA of negative strand RNA viruses. The antisense component of the activator-antisense complex may be complementary to either the genomic strand (negative sense strand), the antigenomic strand (positive sense strand) or mRNAs of the RNA virus. The activator-antisense complexes of the present invention can be designed to be complementary to either the genomic, antigenome or mRNAs of any negative strand RNA virus, including but not limited to, respiratory syncytial virus, parainfluenza virus, influenza virus, mumps virus, and rabies virus. The present invention is exemplified by oligonucleotides directed to RSV strain A2, (the sequence of RSV strain A is given in FIGS. 1A–1H, in the 5'→3' orientation) but the invention can be practiced with any other negative strand RNA virus having a known genomic sequence. The antigenomic sequence can be derived therefrom by routine techniques. Negative strand RNA viruses have multiple genes, i.e., the virion contains the complement of the coding strand. On entry into a host cell the genome is transcribed to produce the various mRNAs encoding the viral proteins and also to produce an entire complementary RNA, i.e., the RSV antigenome, from which the genomic strands of the progeny virus are transcribed. According to the invention, the sequence of the antisense oligonucleotide is selected so that the activator-antisense complex binds to and thereby causes the catalytic destruction of the RNA virus genomic, antigenomic strand or mRNAs.

5.1.1 ANTISENSE OLIGONUCLEOTIDES TARGETING THE GENOMIC RNA STRAND

The present invention relates to a complex of an oligonucleotide complementary to a region of the virus RNA genomic strand characterized by repeated or conserved or consensus sequences coupled to an activator of RNase L. In particular, the oligonucleotide component has a sequence of approximately 17 nucleotides complementary to a number of repeated or consensus sequences that occur within the critical gene-end-intragenic-gene-start signals of the virus RNA genome.

In a preferred embodiment of the present invention, the genomic strand of RSV is targeted to those conserved sequences that occur in gene-start, intragenic and gene-end signals. In a preferred embodiment, the following sequence is used as the antisense cassette of the 2-5A-antisense chimera:

5' AAA AAT GGG GCA AAT AA3' (SEQ ID NO:13).

This 17-mer targets a number of sequences that occur within the critical gene-end-intragenic-gene-start signals of the RSV genomic RNA.

In another embodiment of the present invention, the genomic strand of RSV may be targeted using any of the following sequences as the antisense cassette of the 2-5 A-antisense chimera:

5' GAA GAT GGG GCA AAT AC 3' (SEQ ID NO:14)
5' AAG GGA GGG GCA AAT AT 3' (SEQ ID NO:15)
5' ACA CAT GGG GCA AAT AA 3' (SEQ ID NO:16)
5' AAC ACA GGG GCA AAT AT 3' (SEQ ID NO:17)
5' AAA ACT GGG GCA AAT AT 3' (SEQ ID NO:18)
5' AGT TGT GGG ACA AAA TG 3' (SEQ ID NO:19)

Each gene of the RSV genomic RNA begins with a conserved nine-nucleotide gene-start signal, 3'CCCCGUUUA, with the exception of the L gene, which has the signal 3'CCCUGUUUUA (SEQ ID NO:20). Transcription begins at the first nucleotide of the gene-start signal. Each RSV gene terminates with a semi-conserved 12- to 13-nucleotide gene-end signal, 3' UCAA-UUNAUAUAUUUU (SEQ ID NO:21), which directs transcriptional termination and polyadenylation. Antisense oligonucleotides, in accordance with the present invention, are those that are complementary to the critical gene-start or gene-end signals required to initiate or terminate transcription.

In accordance with the present invention, the activator-antisense complexes can also be designed to target repeated or consensus sequences of the genomic strand of other negative strand RNA viruses. In this aspect of the invention, Sendai, vesicular stomatitis and influenza viral genes are transcribed from 3' to 5' from a single promoter at the 3' terminus of the genomic RNA. The 3' and 5' termini also contain sequences required for viral replication and viral packaging. These sequences can also be targeted by the antisense oligonucleotides of the present invention to specifically target and cleave the genomic strand of the negative strand RNA genome.

Critical sequences are abstracted from the genome and illustrated in Table 1. Here it is clear that the above 17-mer antisense cassette is a perfect hybridization match for three such vital RSV genomic RNA signal sequences. Also clear is the fact that this consensus oligonucleotide antisense sequence may additionally target other critical regions with lowered but significant efficiency. For instance, the nucleotide sequence signal at the F/intragenic M2 gene start signal, has but two mismatches to the consensus antisense sequence. Moreover, one of these is a terminal mismatch which would have a smaller effect on hybrid duplex stability than a similar internal mismatch. Likewise, the signal at the NS2-intragenic-NS2 gene-start has three mismatches, but only one is of the more critical internal variety. Following this logic, the expected order of hybridization efficiency of the consensus antisense cassette 17-mer with the different listed targets would be: 1=2=4>8>3>6,7>5>>9. In addition, another possible hybridization reaction may be possible, albeit of reduced stability compared to the perfect matches alluded to above. This would involve the possibility of interaction of the 17-mer cassette with both gene-end and gene-start sequences by a looping out of mismatches occurring in the intragenic regions, such as those in sequences 5,6,7, and 9.

TABLE 1

RSV 5A-ANTISENSE OLIGONUCLEOTIDES TARGETING THE GENOMIC RNA

| antisense (SEQ ID NO: 13) | 5'AAA AAT GGG GCA AAT AA3' | mis-matches | |
|---|---|---|---|
| sense Seq ID | | terminal | internal |
| 1. 3'-leader/ NS1 start (SEQ ID NO: 22) | 3'UUU UUA CCC CGU UUA UU5' | 0 | 0 |
| 2. NS1/NS2 gene start (SEQ ID NO: 23) | 3'UUU UUA CCC CGU UUA UU5' | 0 | 0 |
| 3. NS2/N gene start (SEQ ID NO: 23) | 3'CUU CUA CCC CGU UUA UG5' | 2 | 1 |
| 4. N/P gene start (SEQ ID NO: 24) | 3'UUU UUA CCC CGU UUA UU5' | 0 | 0 |
| 5. P/M gene start (SEQ ID NO: 25) | 3'UUC CCA CCC CGU UUA UA5' | 1 | 3 |
| 6. M/SH gene start (SEQ ID NO: 26) | 3'UGU GUA CCC CGU UUA UU5' | 0 | 2 |
| 7. G/F gene start (SEQ ID NO: 27) | 3'U UG UGA CCC CGU UUA UA5' | 1 | 1 |
| 8. F/M2 gene start (SEQ ID NO: 28) | 3'UUU UGA CCC CGU UUA UA5' | 1 | 1 |
| 9. L gene start (SEQ ID NO: 29) | 3'UCA ACA CCC UGU UUU A C5' | 1 | 7 |

The result of this design is that a single 2-5A-antisense chimera would be targeted, with varying degrees of efficiency, to a large number of nucleotide sequence signals that are critical for transcription of the RSV genome to yield RSV mRNAs. Such a strategy should lead to a number of disruptions in the parent RSV genomic RNA, any one of which would, according to the model of RSV transcription and replication, be sufficient to shut down virus replication.

5.1.2 ANTISENSE OLIGONUCLEOTIDES TARGETING THE ANTIGENOMIC OR mRNA STRAND

The present invention relates to a complex of an oligonucleotide complementary to a region of the virus RNA antigenomic strand or mRNAs characterized by an absence of self-hybridizing secondary structure. According to the invention, the portion of the antigenome or mRNAs that normally have no self-hybridizing secondary structure can be determined by the sequence of the RNA antigenome and secondary structure determining algorithms, such as MFOLD.

Thus, in another embodiment of the invention the sequence of the antisense oligonucleotide of the invention is selected so that the antisense oligonucleotide is complementary to a portion of the RSV genome, antigenome or mRNA and will bind to it, i.e., the activator-antisense complex targets activated RNase L to the portion of the RSV antigenome or mRNA complementary to the antisense oligonucleotide. Single stranded RNA molecules have regions in which the polymer "folds back" by self hybridizing. These regions of self hybridizing duplex RNA ("stems") are separated by single-stranded "loops" and "bubbles." Thus, not all portions of the RSV genome, antigenome or mRNA are susceptible to binding to the antisense oligonucleotide with equal affinity and, thus, not all portions of the RSV antigenome are suitable as targets of the activator-antisense complexes.

Which portions of an RNA molecule are in stems and which are in loops or bubbles for the purposes of the invention is determined by a computer modeling program such as "FoldRNA" or "MFOLD", which are in the public domain (e.g., through the Biocomputing Office, Biology Department, Indiana University, Bloomington, Ind.). Such programs systematically assess all possible conformations and determine the conformation that is the most thermodynamically favored, i.e., has the lowest "free energy." Routinely, conformations that have a free energy within 5% or 10% of the optimal conformation are also determined. Most often these nearly optimal conformations are closely related to each other, for example the position of a small bubble can differ by one or two nucleotides. As used herein a RNA strand is said to be "normally single stranded" when it is single stranded in the conformation having the lowest free energy or a free energy equivalent to the lowest free energy.

The algorithm that is implemented by these programs is described in Zuker et al., 1989, SCIENCE 244:48. The number of steps needed to calculate the lowest free energy state of a polynucleotide, according to the algorithm of Zuker is proportional to the cube of length of the polynucleotide. At present, conformations of 2 KB polynucleotides can be routinely calculated while the calculations of polynucleotides that are the length of the entire RSV antigenome (≈15 KB) are burdensome.

However, because of the kinetics of the intramolecular hybridization of polynucleotides, it is unlikely that conformations involving hybridization between widely separated portions of the polynucleotide do in fact occur even if the modeling programs indicate that they would yield a lower free energy state. Thus, no practical purpose is served by calculating the thermodynamically most stable conformation of the entire RSV antigenome. Rather, for the purposes of the invention, the conformation of the RSV antigenome can be calculated using fragments that are about 1–2 KB in length. If the predicted conformation of a particular portion of the RSV antigenome is dependent upon the length or the boundaries of the nucleotide fragment that is modeled, then the modeling program of the shorter fragment, greater than 1 KB in length, and the fragment wherein the portion is located closest to the middle of the fragment is considered to be the "normally" occurring conformation.

There are several major considerations in selecting which portions of the antisense genome are suitable as targets.

1. Since the RNase L is active only on single-stranded sequences and not on double-stranded sequences, it is important that there be significant stretches of non-base-paired or minimally base-paired nucleotides near the chosen RNA target sequence.

2. Since the RNase L prefers cleavage after UNp sequences, it is preferred that the single-stranded region where cleavage may occur should contain uridine. This is preferred but not essential as it has been shown that the activator-antisense complex can direct cleavage to other nucleotides. Maran et al., 1994.

3. Since cleavage occurs on the 5'-side of the RNA target sequence, it is preferred that such uridine-containing single-stranded regions should be on the 5'-side of the target sequence.

4. Since the antisense domain of the activator-antisense complex must form a double-helical complex with an RNA target sequence, it is preferable that such a targeted sequence be located in a single-stranded or predominantly singly-stranded region of the target RNA. This is due to the consideration that such complex formation is an equilibrium process, and the magnitude of association constant for the process is reduced according to the degree and stability of secondary structure within the specific target sequence.

5. For the reasons expressed in (4) above, Zuker's MFOLD algorithm is used to generate a group of plausible RNA secondary structures. A set of structures can be generated using this program which differ only slightly in energy. Typically the folding program generates secondary structures differing in increments of 0.1 Kcal/mol, and are therefore are energetically very similar.

6. Consideration of (1–5) above leads to a search for the most preferred target sequence in an RNA target. This target ideally should be single-stranded throughout the entire sequence that serves as the antisense binding site as well as a region upstream on the RNA of at least 16 and preferable at least 21 nucleotides. Thus in the ideal situation the preferred target site should be the length of the antisense domain (e.g., 18) plus 16 equals 34nucleotide in length. Thus, a search would be made for regions in a potential target RNA for single-stranded regions at least 34 nucleotides long and more preferably at least 45 nucleotides long.

7. One additional preference in the design of the activator-antisense complex relates to the composition of the antisense oligonucleotide. Because the activator-antisense complex operates catalytically, there must exist a necessary mechanism for the dissociation of the complex from its complementary sequence in the target RNA. Thus, it is to be expected that duplexes with a large fraction of GC base pairs would undergo dissociation with more difficulty than those having a large fraction dA-rU or dT-rA pairings. This consideration would also be a preferred design consideration.

FIG. 2A shows the results of the modeling of residues 7900–8800 of the mRNA or antigenomic strand. FIG. 2A also contains indications of the locations of the antisense oligonucleotides that were tested in the Examples below. FIGS. 2B:1–2H:3 show alternative results of modeling residues segments of the RSV antigenome from 1 to 7999, 1100 to 2400 and 2200 to 3300, respectively. Two or three different models of each region, with virtually equivalent energies, are shown. These plots indicate, for example, that preferred embodiments the invention target residues 2490–2530, which is single stranded in all three models, residues 617–663, 3212–3247 and 5240–5288 which are single stranded in at least two of the models shown, and residues 718–772, which is single stranded in one of the three models. It must be remembered that the entire family of generated models differ only by 1.1 kcal/mol, and, therefore, each model represents conformations that can be assumed by the RSV antigenome.

5.2 THE STRUCTURE OF THE ACTIVATOR

Examples of the structure of the activator are described in patent publication WO94/09129, at pages 10, 45 and 46–51, which is hereby incorporated by reference. Briefly, the activator can contain at least three riboadenylate residues, linked by 2'-5'phosphodiester bonds, having a free 5' mono-, di- or triphosphate or thiophosphate. The 5' thiophosphate-tetra-adenylate activator (sp5'A2'(p5'A2')$_3$—O—) is the preferred activator. Other activators include p5'A2'(p5'A2')$_2$—O—, sp5'A2'(p5'A2')$_2$—O—, and p5'A2'(p5'A2')$_3$—O—.

Phosphorothioate and phosphorodithioate linkages between adenine nucleosides can be used as well as phosphodiester. The use of these linkages results in decreased degradation but also decreased activity. Beigelmann, L., et al., 1995, Nucleic Acid Research 23:3989–94. The use of a 5'-thiophosphate results in greatly improved activity and stability. Those skilled in the art appreciate that other nucleotides can be attached to the 3'hydroxyl or 2'hydroxyl of the 2'-5'tri- or tetra-adenylate without changing its activity as an RNase L activator. Thus, these embodiments are also included in the scope of the term "activator of RNase L." Those skilled in the art will further recognize that oligo-nucleotides containing bases other than adenine, such as inosine at the second nucleotide (counting 5'→3') can also be used. Those skilled in the art also recognize that non-nucleotide activators of RNase L can be used in the invention and are equivalents of nucleotide activators. As used herein the term "2-5A" refers to any nucleotide activator of RNase L and the term "activator of RNase L" refers to any activator of RNase L including 2-5A. The term 2',5'A refers specifically to 2',5'-linked oligoadenylates.

5.3 THE STRUCTURE OF THE ANTISENSE OLIGO-NUCLEOTIDES

The antisense oligonucleotide can have any structure now known or to be developed in the antisense art. These include phosphodiesters, phosphorothiodiesters, methylphosphono-diesters and methylphosphonothiodiesters, which provide for increased resistance to degradation after administration. The nucleotides of the antisense oligonucleotide can be 2'-deoxynucleotides or 2'O-methyl nucleotides.

The preparation of modified and unmodified oligonucle-otides is well known in the art (reviewed in Agrawal et al. (1992) Trends Biotechnol. 10:152–158; Agrawal in Protocols for Oligonucleotides and Analogs, Synthesis and Properties (Agrawal, ed.), Humana Press, Totowa, N.J. (1993), Chapter 20). For example, nucleotides can be covalently linked using art-recognized techniques such as phosphoramidate, H-phosphorate chemistry, or methylphosphoramidate chemistry (see, e.g., Uhlmann et al. (1990) Chem. Rev. 90:543–584; Agrawal et al. (1987) Tetrahedron. Lett. 28: (31):3539–3542); Caruthers et al. (1987) Meth. Enzymol. 154:287–313; U.S. Pat. No. 5,149,798). Oligomeric phosphorothioate analogs can be prepared using methods well known in the field such as methoxyphosphoramidite (see, e.g., Agrawal et al. (1988) Proc. Natl. Acad. Sci. (USA) 85:7079–7083) or H-phosphorate (see, e.g., Froehler (1986) Tetrahedron Lett. 27:5575–5578) chemistry. The synthetic methods described in Bergot et al. (J. Chromatog. (1992) 559:35–42) can also be used.

In a preferred embodiment of the present invention a blocker is attached to the 3' terminus of the antisense oligonucleotide to increase resistance to degradation by endonucleases. In one embodiment of the present, a blocker is attached to the 3' terminus of the antisense oligonucleotide and the linker is attached to the 5' terminus of the antisense oligonucleotide. In an alternative embodiment, the linker is attached to the 3' terminus of the antisense oligonucleotide and serves as both linker and blocker. The blocker may be selected from the group consisting of a -p3'N5' nucleotide, a p-O-alkylamine, a p-o-hydroxylalkylamine, a sp-O-alkylamine, a Sp-O-hydroxyalkylamine, ethyl and methyl. In yet another embodiment of the present invention, the 3' terminus of the antisense domain is altered to include a terminal inverted 3'—3' phosphodiester linkage which considerably increases resistance to degradation by exonucleases.

In another embodiment of the present invention a variable number of backbone phosphorothioate residues can be placed at the 5' end and/or 3' end and/or within the antisense domain. The phosphorothioate modification to the antisense enhances the stability of the oligonucleotide. In a particular embodiment of the present invention, three phosphorothioate residues (PS linkages) can be added to both the 5' and 3' ends of the antisense cassette.

5.4 PREFERRED EMBODIMENTS OF THE 2-5A ACTIVATOR ANTISENSE COMPLEXES

In a preferred embodiment of the present invention, the activator-antisense complexes designed to target the genomic strand of an RNA virus comprise an oligonucleotide component having the sequence:

5' AAA AAT GGG GCA AAT AA 3' (SEQ ID NO:13).

In another preferred embodiment of the present invention, the activator-antisense complexes comprise an oligonucleotide component having the sequence:

5' GAA GAT GGG GCA AAT AC 3' (SEQ ID NO:14)

5' AAG GGA GGG GCA AAT AT 3' (SEQ ID NO:15)

5' ACA CAT GGG GCA AAT AA 3' (SEQ ID NO:16)

5' AAC ACA GGG GCA AAT AT 3' (SEQ ID NO:17)

5' AAA ACT GGG GCA AAT AT 3' (SEQ ID NO:18)

5' AGT TGT GGG ACA AAA TG 3' (SEQ ID NO:19)

In another preferred embodiment of the present invention, the 2-5A activator antisense complexes include, but are not limited to:

pA$_4$-anti RSV/(8490–8509), directed against nucleotides 8490–8509;

pA$_4$-3'antiRSV 5'/(8490–8509), directed against nucleotides 8490–8509;

spA$_4$-antiRSV3'-3'A/(8251–8270), directed against nucleotides 8251–8270;

spA$_4$-antiRSV3'-3'T/(8261–8279), directed against nucleotides 8281–8299 in the ORF2 region of M2;

spA$_4$-antiRSV3'-3'T/(8281–8299), directed against nucleotides 8281–8299 in the ORF2 region of M2;

spA$_4$-antiRSV3'-3'A/(8530–8547), directed against nucleotides 8530–8547;

spA$_4$-antiRSV3'-3' C/(8561–8578), directed against nucleotides 88561–8578;

spA$_4$-antiRSV3'-3'G/(8599–8618), directed against nucleotides 8599–8618;

spA$_4$-antiRSV3'-3'T/(1–19), directed against nucleotides 1–19;

spA$_4$-antiRSV3'-3'T/(51–69), directed against nucleotides 51–69;

spA$_4$-antiRSVGe3'-3'T/(1–18), directed against nucleotides 1–18;

spA$_4$-antiRSVGe3'-3'T/(84–101), directed against nucleotides 84–101;

spA$_4$-antiRSVGe3'-3'T/(369–386), directed against nucleotides 369–386.

In the practice of the RSV literature, position 1 of the RSV genome (the virion RNA) is the 3' terminus; position 1 of the RSV antigenome (mRNA) is the 5' terminus. Thus, for example, the antisense oligonucleotide labeled antiRSV/(8490–8509) has the sequence (5'→3') of residues 8509 to 8490 of the RSV genome and is complementary to residues 8490–8509 of the RSV antigenome. Note, however, that the RSV strain A2 genome sequence of FIGS. 1A–1H is in conventional 5' to 3' order. Hereinafter activator-antisense complexes wherein the activator is a 2',5'A are termed "2-5A antisense chimeras."

The secondary structure of the 5' terminus of the RSV antigenomic strand can be more readily disrupted than the internal portions. Thus, the following activator-antisense complexes can be used to practice the invention despite the absence of large loops in modeling of the secondary structure of the antigenomic strand.

| | |
|---|---|
| spA$_4$-antiRSV3'-3'T/(1–19): (Seq ID NO: 7) | sp5'A2'(p5'A2')$_3$-[(Bu)p]$_2$-(5'ttg tac gca ttt ttt cgc g3'-3't5') |
| spA$_4$-antiRSV3'-3'T/(51–69): (Seq ID NO: 8) | sp5'A2'(p5'A2')$_3$-[(Bu)p]$_2$-(5'gta ctt atc aaa ttc tta t3'-3't5') |

At the 3'-terminus of the RSV genome, there is a block of about 50 nucleotides which is not incorporated into the protein encoding transcript of the 3'-proximal gene but which is transcribed to yield a small RNA species that has been called a "leader RNA." Evidence indicates that the exact 3'-end of the genome is the entry site for the RNA transcriptional machinery and that leader RNA synthesis, which involves termination at a purine-rich sequence at the leader-template-NP-gene boundary, is an obligatory prelude to progression of the transcriptase through the rest of the genome. In addition, since the 3'-end of the genome is where both replicative and transcriptional RNA synthesis initiate, this site provides a site at which the critical switch between the two kinds of RNA synthesis may operate. Finally, the 3'-terminus of the RSV genome is rich in uridylate residues which may be more readily susceptible to cleavage by the 2-5A-dependent RNase.

These functions of the 3'-terminus of the genomic strand can be disrupted more readily than other portions of the genomic strand. Thus the following activator-antisense complexes, which bind to the genomic strand can be used to practice the invention:

| | |
|---|---|
| spA$_4$-antiRSVGe3'-3'T/(1–18): (Seq ID NO: 9) | sp5'A2'(p5'A2')$_3$-[(Bu)p]$_2$-(5'acg cga aaa aat gcg tac3'-3't5') |
| spA$_4$-antiRSVGe3'-3'T/(84–101) | (SEQ ID NO: 10): sp5'A2'(p5'A2')$_3$-[(Bu)p]$_2$-(5'ctc cct tgg tta gag atg3'-3't5') |
| spA$_4$-antiRSVGe3'-3'T/(369–386) | (Seq ID NO: 11): sp5'A2'(p5'A2')$_3$-[(Bu)p]$_2$-(5'gaa atg atg gaa tta aca3'-3't5') |

5.5 THE STRUCTURE OF THE LINKER

Any linker that covalently connects an activator of RNase L and the antisense oligonucleotide and does not prevent the activator from activating RNase L can be used in accordance with the present invention. In a preferred embodiment, the linker is attached to the 3' or 2' terminus of a 2-5A activator. In a further preferred embodiment the linker consists of a bis-1,4-butanediol-phosphodiester which connects the 3' or 2' terminus of a 2-5A activator and the 5' or the 3' terminus of the antisense oligonucleotide. Attachment to a terminus of the antisense oligonucleotide is selected for the convenience of synthesis. Those skilled in the art appreciate that attachment to an internal 2' hydroxyl or to a portion of the nucleotide base that is not critical to base pairing are alternative embodiments of the invention.

5.6 USE OF THE ACTIVATOR-ANTISENSE COMPLEXES

The activator-antisense complexes of the invention may be used to inhibit infection by a negative strand RNA virus to which the activator-antisense complex is targeted, in particular RSV infection. The activator-antisense complexes of the invention can be administered to a subject having an RSV infection by any route effective to deliver the activator-antisense complexes to the epithelium of the bronchi, bronchioles and alveoli of the subject. In one embodiment the activator-antisense complexes are delivered by use of an inhaled aerosol, according to the techniques well known in the art for the delivery of ribavirin. In a further embodiment of the invention a mixture of ribavirin and an activator-antisense complex of the invention can be administered in a common pharmaceutical carrier.

In an alternative embodiment the activator-antisense complex can be administered parenterally, e.g., by intravenous infusion. When delivered by intravenous administration, the dose of activator-antisense complex can be determined by routine methods well known to pharmacologists so that the serum concentration approximates the concentration at which antiviral activity is seen in the in vitro examples described below, e.g., a concentration of about 10 $\mu$M of spA$_4$-antiRSV3'-3'T/(8281–8299). When delivered by aerosol administration the dose should be selected so that the tissue concentration in the lung approximates the concentration at which antiviral activity is seen in the in vitro examples.

In yet another embodiment of the present invention, the activator-antisense complexes of the present invention have utility as a diagnostic tool to determine the presence of a specific negative strand virus in a test sample. The activator-antisense complexes of the present invention further have utility as a research tool which may be employed to better understand the negative strand RNA virus life cycle.

5.7 SYNTHESIS OF 2-5A ANTISENSE CHIMERAS

The following is an example of a method to synthesize the 2-5A antisense activators or chimeras of the present invention. Any methods known to those of skill in the art may be used to substitute or modify the methods described herein.

5.7.1 SYNTHESIS AND PURIFICATION OF ANTISENSE ACTIVATORS

Oligonucleotide Structural Types Synthesized. The following generic oligonucleotide types may be prepared:

I. p5'A2 'p(5'A2'p)$_3$-[O(CH$_2$)$_4$Op]$_2$-5'dN3'p(5'dN3 'p)$_n$5'dN
II. A2'p(5'A2'p)$_3$-[O(CH2)$_4$Op]$_2$-5'dN3'p(5'dN3'p)$_n$5'dN
III. dN3'p(5'dN3'p)$_n$5'dN
IV. p5'A2'p(5'A2'p)$_3$-[O(CH$_2$)$_4$Op]$_2$-5'dN3'p(5'dN3'p)$_m$5'dN3'p-3'pdN5'
V. sp5'A2'p(5'A2'p)$_3$-[O(CH$_2$)$_4$Op]$_2$-5'dN3'p(5'dN3'p)$_m$5'dN3'p-3'pdN5'
VI. A2'p(5'A2'p)$_3$-[O(CH$_2$)$_4$Op]$_2$-5'dN3'p(5'dN3'p)$_m$5'dN3'p-3'pdN5'
VII. sp5'A2'p(5'A2'p)$_3$-[O(CH$_2$)$_4$Op]$_2$-5'dN3'p(5'dN3'p)$_n$5'dN
VIII. p5'A2'p(5'A2'p)$_3$-[O(CH$_2$)$_4$Op]$_2$-3'dN5'(p3'dN5')$_n$p3'dN

The following procedures are illustrative of those which may be employed to synthesize the 2-5A-antisense chimeric oligonucleotides in classes I–VIII above. In general, they follow the synthetic strategy developed in Lesiak et al., 1993.

Reagents and Chemicals Employed.

1. For initiation of synthesis on solid support:
   dA-3'-lcaa-CPG (500 Å)
   5'-O-dimethoxytrityl-N6-benzoyl-2'-deoxyadenosine-3'-lcaa-CPG
   dC-3' lcaa-CPG (500 Å)
   5'-O-dimethoxytrityl-N4-benzoyl-2'-deoxycytidine-3'-lcaa-CPG
   dG-3' lcaa-CPG (500 Å)
   5'-O-dimethoxytrityl-N2-isobutyryl-2'-deoxyguanosine-3'-lcaa-CPG
   dT-3'-lcaa-CPG (500 Å)
   5'-O-dimethoxytritylthymidine-3'-lcaa-CPG These solid supports are used to synthesize oligonucleotides with the normal 3'→5' phosphodiester bonds. All were 1 $\mu$mole size. These DMT protected nucleosides are attached to controlled pore glass (CPG) through a succinyl group and a long chain alkyl amine (lcaa) linker are commercially available products of Applied Biosystems (Foster City, Calif.). These supports are employed in the synthesis of generic oligonucleotide types I, II, III, and VII.

dA-5'-lcaa-CPG (500 Å)
   3'-O-dimethoxytrityl-N6-benzoyl-2'-deoxyadenosine-5'-lcaa-CPG
   dC-5' lcaa-CPG (500 Å)
   3'-O-dimethoxytrityl-N4-benzoyl-2'-deoxycytidine-5'-lcaa-CPG
   dG-5' lcaa-CPG (500 Å)
   3'-O-dimethoxytrityl-N2-isobutyryl-2'-deoxyguanosine-5'-lcaa-CPG
   dT-5'-lcaa-CPG (500 Å)
   3'-O-dimethoxytritylthymidine-5'-lcaa-CPG These solid supports are obtained form Glen Research (Sterling, Va.) and are used to synthesize oligonucleotides with the reversed polarity 5'→3' phosphodiester bonds. All were 1 $\mu$mole size. These supports are employed for the synthesis of generic oligonucleotide types IV, V, VI, and VIII.

2. Elongation of the DNA antisense chain.

For normal 3'→5' phosphodiester bond oligonucleotides, a total of 500 mg of each of the following phosphoramidites (Applied Biosystems) is dissolved in the indicated amount of anhydrous acetonitrile to make a 0.1 M phosphoramidite solution:

5'-O-dimethoxytrityl-N6-benzoyl-2'-deoxyadenosine-3'-(2-cyanoethyl-N,N-diisopropyl)phosphoramidite (5.6 mL)
5'-O-dimethoxytrityl-N4-benzoyl-2'-deoxycytidine-3'(2-cyanoethyl-N,N-diisopropyl)phosphoramidite (5.9 mL)
5'-O-dimethoxytrityl-N2-isobutyryl-2'-deoxyguanosine-3'-(2-cyanoethyl-N,N-diisopropyl)phosphoramidite (5.8 mL)
5'-O-dimethoxytrityl-2'-deoxythymidine-3'-(2-cyanoethyl-N,N-diiso propyl)phosphoramidite (6.6 mL)

The foregoing were used in the preparation of generic oligonucleotide types I, II, III, IV, V, VI, and VII.

For the synthesis of oligonucleotides with all DNA phosphodiester bonds with reversed polarity, the following phosphoramidites may be obtained from Glen Research (Sterling, Va.).

3'-O-dimethoxytrityl-N6-benzoyl-2'-deoxyadenosine-5'-(2-cyanoethyl-N,N-diisopropyl)phosphoramidite (5.6 mL)
3'-O-dimethoxytrityl-N4-benzoyl-2'-deoxycytidine-5'(2-cyanoethyl-N,N-diisopropyl)phosphoramidite (5.9 mL)
3'-O-dimethoxytrityl-N2-isobutyryl-2'-deoxyguanosine-5'-(2-cyanoethyl-N,N-diisopropyl)phosphoramidite (5.8 mL)
3'-O-dimethoxytrityl-2'-deoxythymidine-5'-(2-cyanoethyl-N,N-diisopropyl)phosphoramidite (6.6 mL)

The above intermediates were employed to synthesize generic oligonucleotide type VIII.

3. Linker to join chimeric domains.

The linker, (2-cyanoethyl-N,N-diisopropyl)-[4-O-(4,4'-dimethoxytrityl)butyl]phosphoramidite, is synthesized by a modification of an earlier described procedure (Lesiak et al., 1993), and a 0.1 M solution was made by dissolving 100 mg linker in 1.7 mL of anhydrous acetonitrile.

4. For synthesis of 2',5'-oligoadenylate domain of the chimera.

5'-O-dimethoxytrityl-N6-benzoyl-3'-O-t-butyldimethylsilyladenosine-2'-N,N-diisopropylcyanoethylphosphoramidite (ChemGenes Corp., Waltham, Mass., cat no. ANP 5681). A 0.1 M solution is made by dissolving 500 mg of monomer in 5.0 mL of anhydrous acetonitrile.

5. Phosphorylation Reagent for 5'-terminus of 2',5'-oligoadenylate domain of chimera.

2-[2-(4,4'-dimethoxytrityl)ethylsulfonyl]ethyl-(2-cyanoethyl)-(N,N-diisopropyl)-phosphoramidite (Glen Research, Sterling, Va. cat no. 10-1900-90) is used at a concentration of 0.2 M in anhydrous tetrazole/acetonitrile (ABI) for semi-automated synthesis.

6. Other Reagents.

All other DNA synthesis reagents may be obtained from Applied Biosystems Inc. which includes diluent (acetonitrile), activator solution (tetrazole/acetonitrile), capping solutions (A: acetic anhydride solution and B: N-methylimidazole solution), deblocking reagent (trichloroacetic acid solution), oxidizer (iodine solution), and tetraethylthiuram disulfide sulfurization reagent.

Tetrabutylammonium fluoride in tetrahydrofuran (Aldrich, Milwaukee, Wis.) was used to deblock the t-butyldimethylsilyl group used for protection of the 3'-hydroxyls of (2',5')-oligoriboadenylate domain.

5.7.2 AUTOMATED PROCEDURES FOR THE SYNTHESIS OF ACTIVATOR-ANTISENSE COMPLEXES

The following is an example of modified automated or semi-automated procedures to synthesize the 2',5'-oligoadenylate antisense activators or chimeras of the present invention.

All of the chemicals are dried over $P_2O_5$ in vauco overnight before use. The 1 μmole deoxynucleoside-lcaa-CPG column was used.

The core (2',5')-oligoadenylate/antisense chimera refers to the complete 2',5'A-antisense chimera minus the 5'-terminal monophosphate group and has three regions defined for synthetic purposes: an antisense region, a linker region, and (2',5')-oligoadenylate region.

1 μmole scale standard synthesis cycle is used. The cycle is modified by changing the coupling time (coupling of monomer) for each different region. The monomer/acetonitrile solution is installed on the DNA synthesizer by a double change procedure to avoid contaminants. After the synthesis of each region, the column is dried completely by Argon for at least 3 min. and the synthesis cycle, trityl mode, and sequence are edited for the synthesis of next region of the desired oligonucleotide.

For preparation of the 5'-monophosphate terminating chimeras, the core oligonucleotide may synthesized with the trityl group on, and the column was dried and removed from the DNA synthesizer.

Cleavage and Deprotection

1. The oligonucleotide is cleaved from the CPG support by concentrated ammonium hydroxide/ethanol (3:1 v/v) at room temperature for 2 hours.

2. The ammonium hydroxide/ethanol solution of crude oligonucleotide is removed into a 3 mL vial and sealed tightly. The solution is incubated at 55° C. for 8 hours to remove the protecting groups on the bases.

3. The resulting ammonium hydroxide/ethanol solution of oligonucleotide is transferred to a glass tube, and cooled completely in a ice-bath. The solution is then evaporated to dryness in a speedvac concentrator and a solution of tetrabutylammonium fluoride (2 mL, 1.0 M) in THF is added, and the entire mixture is vortexed for at least 1 min. This reaction mixture was allowed to incubate at room temperature for at least 10 hours.

An equivalent volume of 0.1 M TEAA (tetraethylammonium acetate) (pH 7.0) buffer is added, mixed and evaporated to half volume to remove THF. The residue is subjected to purification by HPLC.

Purification of the Oligonucleotides

1. Polystyrene Reverse-Phase Ion-Pair Chromatography (PRP-IPC) Protocol (a modification of the method of Swiderski, et al., 1994).

The oligonucleotide is dissolved in about 4–5 mL water to make a clear solution (centrifuged if necessary), and the clear solution is directly injected into the PRP-1 HPLC column (300×7 mm). The reaction mixture is thus simultaneously desalted and purified.

Solvent A: 10 mM tetrabutyl ammonium phosphate (TBAP), pH 7.5 in water.

Solvent B: 10 mM TBAP, pH 7.5 in acetonitrile/water (8:2 v/v).

The sample is eluted with a convex gradient of 5–90% solvent B in A in 60 min. at a flow rate of 1.5 mL/min.

Fractions containing desired oligo are pooled and evaporated to about 1–2 mL. The oligo-TBA ion-pair is converted into its sodium salt form by the following procedure:

1 mL of Dowex 50W ion exchange wet resin ($Na^+$ form) is added into oligonucleotide/water solution. The solution is stirred for at least 30 min. in the cold room. The resin is removed by passing the solution through a Poly-Prep chromatography column (Bio-Rad, Cat. # 731-1550). The resin is washed with extra water until no oligonucleotide remained on the resin.

Alternately, prior to Dowex treatment the oligonucleotide is passed through a C-18 Sep-Pak cartridge according to the following procedure.

a. The C-18 cartridge is pre-washed with 10 mL methanol and 10 mL water.

b. The oligo solution is loaded onto the cartridge.

c. The cartridge is washed with 20 mL water to remove salt from the column.

d. The oligonucleotide is eluted with 10 mL of 50% methanol in water.

e. The desalted oligonucleotide is detected by UV spectrophotometer and the fractions containing oligo are combined and concentrated.

Dialysis of (2',5')-Oligoadenylate/antisense Chimeras

After Purification by HPLC and ion exchange, the oligonucleotide (sodium salt) is dialyzed to remove small molecules and excess salt. The dialysis is carried out at 4° C. The oligonucleotide is dialyzed against 0.02 M NaCl first for 4–6 hours and then against water for 48 hours. If the oligonucleotide is desalted on C-18 sep-pak cartridges after HPLC purification, the time of dialysis can be shortened to 6–10 hours.

Post-treatment of Oligoadenylate/antisense Chimeras

The oligonucleotide, after dialysis, is passed through a 0.22 μM millex-GV filter unit (Millipore, Cat. No. SLGV025LS) for sterilization. The resulting solution is quantitated as O.D. A260 by UV/Vis spectrophotometry.

5.7.3 Nucleotide Composition Analysis of (2',5')-Oligoadenylate/antisense Chimeras 1. Nucleotide Composition Analysis.

The nucleotide composition of the chimeric oligonucleotide is analyzed by enzymatic digestion with snake venom phosphodiesterase (*Crotallus durissus*) (Pharmacia, cat # 27,0821-01).

A purified oligonucleotide (0.2 A260 O.D.U.) is incubated with snake venom phosphodiesterase (0.15 units) in 50 mM Tris/HCl, pH 8.0, 0.5 mM $MgCl_2$, pH 8.0. The 100 μL mixture is incubated at 37° C. for at least 3 hours. For chimeric oligonucleotides containing a 3'-3'dN, such as Oligonucleotide Structural Type IV, the incubation time was extended to 10 hours.

After digestion, the solution is filtered with a Microconcentrator-10 (Amicon, Inc. product No. 42406). The microconcentrator is first spin-rinsed with water before addition of 100 μL sample solution. The centrifugation time is typically 45 min. The clear solution is used for HPLC analysis.

An aliquot (5–10 μL) of the hydrolysate is analyzed by reverse phase HPLC using a Beckman Ultrasphere C-18 ODS column (0.46×25 cm). Separation of the digestion products is accomplished under the following conditions: 2% B isocratically for 20 min. linear gradient 2–50% B for 15 min. and held isocratically 10 min where solvent A was 100 mM ammonium phosphate, pH 5.5 and solvent B is methanol/water (1:1 v/v). The flow rate may be 0.5 mL/min. The standard markers dCMP, TMP, dGMP, AMP and dAMP (Aldrich Chem. Co.) may be used to compare retention times and elution orders of the hydrolysis products. Typically, the peaks obtained from the enzymatic hydrolysis of an oligonucleotide have retention times of 9.7 min. (dCMP), 27.3 min. (TMP), 29.6 min. (dGMP), 31.7 min. (AMP), 39.5 min. (Alinker) and 41.2 min. (dAMP). The retention times vary depending on the column, pH value of mobile phase and the equilibrium times of the column. The integrated peak areas provide the relative content of each nucleotide. The extinction coefficients of 7610 (dCMP), 8158 (TMP), 9969 (dGMP), 12342 (AMP & Alinker), 14361 (dAMP) measured at 260 nm in 100 mM ammonium phosphate, pH 5.5 may be used in the analysis.

Oligonucleotide Purity Confirmation

The purities of (2',5')-oligoadenylate/antisense chimeras may be checked by HPLC or gel capillary electrophoresis (GCE). The purity may be obtained by the integration of peak area detected at 260 nm.

1. Gel Capillary Electrophoresis (GCE) Method

The measurement of oligonucleotide purity is performed on an Applied Biosystems 270A-HT capillary electrophoresis instrument using MICRO-GEL100 (Applied Biosystems Inc.) gel filled capillaries (50 μM i.d., effective length 27 cm, running buffer, 75 mM Tris phosphate (pH 7.6), 10% methanol). Detection was at 260 nm. A typical electrophe of (2',5')-oligoadenylate/antisense chimera may be obtained by the following conditions: sample concentration approx. 0.1 O.D./mL, electrokinetic injection was 2 s at −5 kv. Voltage was −14 mA (19 mA) and the operation temperature are 30° C. Under this condition, the (2',5')-oligoadenylate/antisense chimera has about 1 min. earlier elution time than that of its core analogue.

2. Dionex PA-100 Ion Exchange HPLC Method.

The purities of oligonucleotides could also be measured by a Dionex Ion exchange HPLC. Usually, the dionex PA-100 ion exchange column could provides higher resolution and better peak shape compared with other HPLC chromatographic method for the analysis of (2',5')-oligoadenylate/antisense chimera.

A typical chromatogram of (2',5')-oligoadenylate/antisense may be obtained by the following conditions: Dionex PA-100 (4×250 mm) column (Dionex, cat # 43010). Solvent A is 25 mM Tris/HCl and 0.5% acetonitrile (pH 7.0), solvent B is 25 mM Tris/HCl, 0.5% acetonitrile and 1 M ammonium chloride (pH 7.0). The sample is eluted in linear gradient of 10–70% B in A during 30 min. and held isocratically for 10 min. at a flow rate of 1 mL/min. Detection is at 260 nm.

6. EXAMPLE: SELECTION OF TARGET

The following describes a preferred method of the present invention for the selection of highly effective 2-5A antisense chimera based on a computer analysis of the RNA secondary structure.

A computer-assisted analysis of the secondary structure of the RSV mRNA was performed to identify single-stranded regions as oligonucleotide binding sites. Computer prediction of the secondary structure of RSV genomic or antigenomic strand, nucleotides 7900 to 9079, including a 3'portion of the M2 gene, encoding a viral envelope protein, and a 5' region of the L gene, was performed using the program MFOLD which finds a secondary structure of minimum free energy for an RNA molecule based on published values of stacking and loop destabilizing energies. MFOLD is the program of Michael Zuker (Zuker, 1989). The energies used by Zuker's program were first described by Salser (1977) and are now defined by Turner and colleagues (Freier et al., 1986). The analysis showed a large loop from positions 8250 to 8299. This loop was present in a 90 codon open reading frame of unknown function downstream (3') of the major M2 open reading frame. Three chimeric compounds were synthesized which were complementary to sequences in the loop, $spA_4$-antiRSV3'-'3A/(8251–8270), $spA_4$-antiRSV3'-3'T/(8261–8279), and $spA_4$-antiRSV3'-3'T/(8281–8299). In addition, three oligonucleotides were synthesized to other regions in RNA that included a bulge, a hair-pin and a small loop, $spA_4$-antiRSV3'-3'A/(8530–8547), $spA_4$-antiRSV3'-3'C/(8561–8578), and $spA_4$-antiRSV3'-3'G/(8599–8618), respectively. When added to the RSV infected 9HTE cells at concentrations of 3.3 μM, the three oligonucleotide directed to the large loop had the greatest level of antiviral activity (78 to 91% inhibition). These three oligonucleotides had very substantially improved anti-RSV activity compared to the previously described 2-5A antisense molecules (3 to 16.5% inhibition at 3.3 μM). The chimera with the greatest anti-RSV effect was $spA_4$-antiRSV3'-3'T/(8281–8299), which produced 97 and 99.6% inhibition of RSV replication at doses of 6.6 and 9.9 μM, respectively. The oligonucleotide directed to the region in the RNA with the bulge, $spA_4$-antiRSV3'-3'A/(8530–8547), showed almost no antiviral effect at 3.3 μM. The 2-5A antisense molecules to the hairpin and small loop, $spA_4$-antiRSV3'-3'C/(8561–8578), and $spA_4$-antiRSV3'-3'G/(8599–8618), had intermediate activities, 57 and 43% inhibition of RSV replication at concentrations of 3.3 μM.

FIG. 3 presents a comparison of $spA_4$-antiRSV3'-3'T/(8281–8299) and $spA_2$-antiRSV3'-3'T/(8281–8299). Only the tetraadenylate is an activator of RNase L, hence the greater potency of the $spA_4$-linked oligonucleotide compared to the $spA_2$-linked oligonucleotide establishes the role of RNase L activity in the protective effects of the present invention.

7. EXAMPLE: ANALYSIS OF ANTIVIRAL ACTIVITY OF 2-5A ANTISENSE CHIMERAS

The following example provides a preferred embodiment of the present invention for the determination of the antiviral activities of the 2-5A antisense activators of the present invention. In particular this example demonstrates the correlation of antiviral activities and RNA levels after treatment of RSV-infected 9HTE cells with the 2-5A antisense chimeras.

To determine if RSV RNA levels correlated with antiviral activity, RT-PCR analysis was performed on RNA isolated from RSV-infected and uninfected 9HTE cells with and without treatment with $spA_4$-antiRSV3'3'T/(8281–8299) or $spA_4$-antiRSV3'3'A/(8530–8547). An M2 RNA sequence in RSV (from nucleotides 7879 to 8465) was converted to cDNA and amplified by PCR. M2 RNA from the RSV-infected cells produced an RT-PCR DNA product that was clearly visible. In contrast, there was no M2 RNA detected from the RSV-infected cells treated with $spA_4$-antiRSV3'3'T/ (8281–8299). The chimera directed against the RSV L mRNA and the corresponding sequence in the antigenomic RNA, $spA_4$-antiRSV3'3'A/(8530–8547), had little effect on levels of M2 RNA (17% inhibition). Accordingly, the levels of viral M2 RNA were dramatically reduced in 9HTE cells treated with $spA_4$-antiRSV3'-3'T/(8281–8299) while those treated with a relatively inactive control chimera against the RSV L mRNA, $spA_4$-antiRSV3'-3'A/(8530–8547), had no effect on levels of M2 RNA. Levels of GAPDH transcripts were similar in all of these RNA preparations. These results showing loss of the specific RSV mRNA target are consistent with involvement of RNase L.

8. EXAMPLE: 2-5A ANTISENSE ACTIVATORS INHIBITS RSV REPLICATION IN PREVIOUSLY RSV INFECTED HUMAN EPITHELIAL CELLS

The following example demonstrates the efficacy of the 2-5A antisense activator complexes of the present invention designed to target mRNAs or the antigenomic strand of RSV RNA genome to inhibit RSV infection. To develop 2-5A antisense chimeras with the potential to block RSV replication, an oligonucleotide binding site in the viral RNA polymerase (RSV L) mRNA, which encodes a low abundance message that is absolutely required for RSV replication was selected. The first chimera synthesized and evaluated was $pA_4$-antiRSV/(8490–8509). The binding sites for the chimeric oligonucleotide's antisense domain are to the transcripts of nucleotides 8490–8509 in the RSV genome, which spans the translation start codon for the L protein, and to nucleotides 8490–8509 of the antigenomic strand (the template for reproduction of the genome). Since to function as an effective treatment, a candidate agent must be able to inhibit viral replication subsequent to diagnosis, the anti-RSV effect of the 2-5A antisense chimera was determined on human tracheal epithelial cells, 9HTE, with treatments beginning either 4 h before RSV infection (pre-/post-infection treatments) or 2 h following infection (post-infection treatments). In the post-infection treatments, $pA_4$-antiRSV/(8490–8509) at (10 μM final concentration), was added at $t_{+2}$, $t_{+14}$ and $t_{+26}$, (numbers represent time in h relative to time of infection, $_0$) For pre-infection treatment, $pA_4$-antiRSV/(8490–8509) (10 μM final concentration), was added at $t_{-4}$, and $t_0$ in addition to $t_{+21}$; $t_{+14}$ and $t_{+26}$. Virus harvested from control and oligonucleotide-treated 9HTE cells was measured by infecting CV-1 cells and subsequently counting viral plaques. Post-infection treatment of 9HTE cells with $pA_4$-antiRSV/(8490–8509) was found to be just as effective as pre-/post-infection treatment; both resulted in about 70% inhibition of RSV replication. On the basis of these experiments, all subsequent experiments were performed with post-infection treatments only. Additionally, these experiments indicate the potential use of these compounds as a treatment for active infection as compared to a prophylactic measure.

8.1 MATERIALS AND METHODS

Cell culture, RSV propagation and infection, and viral titer assays.

The human tracheal epithelial cell line, 9HTE, (Gruenert et al., 1988) and CV-1 cells, (American Type Culture Collection, Rockville, Md., CCI#70) a green monkey kidney cell line which is highly permissive to RSV infection, were cultured in minimal essential medium (MEM) supplemented with 10% (v/v) fetal bovine serum (FBS), 2 mM L-glutamine, 1× MEM amino acids solution, 1× MEM non-essential amino acids solution, 100 U/ml penicillin, 100 μg/ml streptomycin and 0.25 μg/ml amphotericin B ("culture medium") (all reagents from Gibco BRL, Bethesda, Md.). RSV strain $A_2$ (ATCC No. VR1302) was propagated in CV-1 cells. CV-1 monolayers were infected at a multiplicity of infection (M.O.I.) of 0.2 and cultured 46 h in MEM, 2% FBS, 1× Penicillin/Streptomycin (PS) in 5% $CO_2$, 95% $O_2$ at 37° C. Cells were then washed 2 times in MEM and subsequently covered in MEM, 2% FBS, 1× PS, 50 mM HEPES (pH7.5), 100 mM $Mg(SO_4)$. After 2 h at 37° C., cells were scraped and sonicated as previously described (Panuska et al., 1995). Aliquots (1 ml each) of cell sonicates were flash frozen in ethanol/dry ice within 20 min of scraping. Several aliquots were then thawed and titered by a plaque assay on CV-1 cells as previously described (Cirino et al., 1993). The range of virus yield from this procedure was 2 to $7 \times 10^6$ plaque forming units (pfu) per ml.

Oligonucleotide, interferon α and ribavirin treatments of 9HTE cells before and after RSV infection.

Infection of 9HTE cells was performed as previously described (Merolla et al., 1994). Briefly, confluent monolayers were exposed to RSV diluted in MEM, 2% FBS, for 2 h at 37° C. in 5% $CO_2$, 95% $O_2$. After exposure, cells were washed two times with serum-free MEM media and then fresh culture media (with 10% FBS) was added. Oligonucleotides were either added 4 h prior to infection ($t_{-4}$) or immediately after infection ($t_{+2}$) and also at $t_{+14}$ and $t_{+26}$. Cells were harvested for plaque assays at 36 h post-infection to determine viral titers as previously described (Cirino et al., 1993). Cells were washed twice to remove any residual antisense and were then scraped in MEM containing 2% FBS, 1× PS. 9HTE cells were sonicated for 20 sec on ice then the extracts were serially diluted and transferred to a confluent monolayer of CV-1 for quantitation of infectious viral particles. CV-1 were exposed to sonicated 9HTE for 2 h then washed once in MEM and overlaid with Eagle's minimal essential medium (EMEM, BioWhittaker, Walkersville, Md.) containing 2% FBS, 200 U/ml penicillin, 200 μg/ml streptomycin, 0.5 μg/ml amphotericin B, and 0.4% agarose. Five days later, cells were fixed in 10% formalin for 1 h, the agarose plugs removed, and 0.2% crystal violet in 10% formalin was added for 2 min. CV-1 were subsequently washed in water to remove excess dye and the number of syncytia (plaques) were quantified under a microscope.

In certain experiments (data not shown), interferon a (Schering, Intron A, interferon α-2B, $10^5$ U/ml) or Ribavirin (ICN Pharmaceuticals, Costa Mesa, Calif., 100 μg/ml) were also added after infection. Interferon a was added to a final concentration of 50 U/ml when chimeric antisense was added, i.e. $t_{+2}$, $t_{+14}$ and $t_{+26}$. In contrast, ribavirin, which has a half-life of 40 days in vivo, was added only at $t_{+2}$ to a final concentration of $10^{-13}$ M.

Reverse Transcriptase-coupled Polymerase Chain Reaction (RT-PCR)

RNA was collected from 2×10$^5$ 9HTE cells at 8 h post-infection (M.O.I.=10) by RNAzol treatment as described by the manufacturer (Tel-Test, Inc, Freindswood, Tex.). RNA was isolated after 8 h to limit RSV replication to a single cycle. Isolated RNA (≈1 μg) was incubated with 100 pmoles of the appropriate downstream (−) primer listed below or 100 pmoles of random hexamer (used for glyceraldehyde-3-phosphate dehydrogenase, GAPDH, mRNA only). RNA and primers were heated to 70° C. for 10 min then cooled rapidly on ice for 5 min. A final reaction volume of 30 ml contained: 300 μM each dNTP, 200 U SuperScript reverse transcriptase (GibcoBRL, Bethesda, Md.), 50 mM Tris-HCl (pH 8.3), 75 mM KCl, 3 mM MgCl2, and 10 mM DTT. Reverse transcription was allowed to proceed for 1 h at 37° C.

PCR reactions were performed using 50 μl Hot-Start tubes (Molecular Bio-Products, San Diego, Calif.) with 25 μl lower buffer containing 40 mM Tris-HCl (pH=8.4), 100 mM KCl, 2 mM MgCl2, 600 μM each dNTP, and 100 pmoles each of the appropriate primer pairs;

| TARGET | SEQUENCE | ANNEALING TEMP |
|---|---|---|
| RSV(L+) (Seq ID NO: 1) | [5'-TCAATGGTCCTTATCTCAA-3'] | 46° C. |
| RSV(L−) (Seq ID NO: 2) | [5'-GAGCTTTATTAGCAGCATC-3'] | |
| GAPDH(+) (Seq ID NO: 3) | [5'-AAATCCCATCACCATCTTC-3'] | 57° C. |
| GAPDH(−) (Seq ID NO: 4) | [5'-CACCACCCTGTTGCTGTAG-3'] | |
| RSV(M2+) (Seq ID NO: 5) | [5'-AAACAATCAGCATGTGTTG-3'] | 46° C. |
| RSV(M2−) (Seq ID NO: 6) | [5'-AATGTAACGATGTGGTGAG-3'] | |

25 μl Hot-Start upper buffer contained 5 U Taq DNA polymerase (GibcoBRL) and 1/10th of the cDNA from the RT reaction. 30 cycles of PCR were performed with 1 min at 92° C., 1.5 min at the annealing temperature indicated above, and 2 min at 72° C. Aliquots of the RT/PCR mixtures were analyzed on 1% agarose/TBE gels.

8.2 RESULTS

The following results demonstrate the antiviral activities of 2-5A antisense and control chimeric oligonucleotides directed against the viral L polymerase mRNA translation start site.

An initial series of oligonucleotides included various controls and additional modifications designed to stabilize the chimeras against enzymatic decay in the cell culture (Table 3). To compare the antiviral effects of these oligonucleotides, 9HTE cells were infected with RSV and subsequently treated three times ($t_{+2}$, $t_{+14}$, and $t_{+26}$ h) with three concentrations of oligonucleotides (3.3, 6.6 and 9.9 μM) and virus was harvested after 36 h. Chimeric antisense lacking only the 5'-phosphate, in A$_4$-antiRSV3'-3'C/(8490–8509), deficient in the ability to activate RNase L (Maran et al., 1994), was used as a control. This derivative showed only minimal anti-RSV activity (28.3% inhibition at 9.9 μM/treatment as compared to 64.8% inhibition by the 5'-phosphorylated derivative, pA$_4$-antiRSV3'-3'C/(8490–8509)). To stabilize the 3' termini of the chimeras, these ends were masked. In one derivative, pA$_4$-3'antiRSV5'/(8490–8509), the 2-5A portion of the chimera was linked to the 3' end of the antisense moiety instead of to the 5' end of the oligonucleotide. In this way, the 3' terminus of the antisense is protected from exonuclease digestion though its attachment to the linker (Li et al., J. Med Chem. 18: 2959–2966, 1997). This analog produced a 69% inhibition of virus production at the highest concentration tested (9.9 μM) (Table 3). In another chimera, pA$_4$-antiRSV3'-3'C/(8490–8509), the 3' terminal deoxynucleotide was connected by a 3'-3'phosphodiester linkage to the penultimate deoxynucleotide thereby slowing 3' exonuclease digestion (G.L., W.X., & P.F.T., unpublished observations). This compound produced a 1.6-fold enhanced antiviral activity at 6.6 μM (64.3% inhibition) compared with the standard, unmodified chimera, pA$_4$-antiRSV3'-3'C/(8490–8509) tested at the same concentration (38.8% inhibition). Alternately, a 5'-thiophosphate was used to stabilized the 2-5A domain of the chimera against phosphatase. Such thiophosphorylated derivatives of 2-5A and 2-5A antisense were previously shown to be fully capable of activating RNase L when compared to standard, 5'-phosphorylated, 2-5A and 2-5A antisense (Xiao et al., 1994 and Maran et al., 1994). spA$_4$-antiRSV/(8490–8509) showed a substantially increased anti-RSV effect with 71% and 94% inhibition of viral growth at treatment concentrations of 6.6 and 9.9 μM, respectively (Table 3).

9. EXAMPLE: COMPARATIVE DATA OF spA-antiRSV3'3'T/(8281–8299)

A comparison of the efficacies of spA$_4$-antiRSV3'3'T/(8281–8299) treatment and conventional ribarvirin treatment can be obtained by determining the RSV-inhibitory concentration and the cytotoxic concentration of each compound. Cultures of the human laryngeal carcinoma cell line HEp-2 and the murine renal cell line MA-104 were established and infected with an MOI=0.005. Cultures were fed twice daily. Treatment with either ribavirin or spA$_4$-antiRSV3'3'T/(8281–8299) was begun simultaneously with infection and continued for four days. Treatment was then withdrawn and the test read on day 5. The effects of treatment on RSV infection were reported as 1) an EC$_{50}$, the concentration at which there was a 50% reduction in the observable cytopathic effects of infection and 2) an EC$_{90}$, the concentration at which there was a 90% reduction in viral production. The cytotoxic concentration, the IC$_{50}$ was taken as the concentration that resulted in a 50% reduction in cell number. Therapeutic efficacy is estimated by the Selectivity Index, which is the ratio of IC$_{50}$/EC$_{50}$.

The results are shown in Tables 5 and 6. Table 5 shows that in HEp-2 cells spA$_4$-antiRSV3'3'T/(8281–8299) had an EC$_{50}$ of 0.3 μM; ribarvirin had an EC$_{50}$ of 4 μM. The IC$_{50}$s were >10 μM and 41 μM, respectively. Thus, spA$_4$-antiRSV3'3'T/(8281–8299) had an SI more than three fold higher than ribavirin.

Table 6 shows the analogous results concerning MA-104 cells. The SI of spA$_4$-antiRSV3'3'T/(8281–8299) and ribavirin were found to be >500 and about 200, respectively.

10. EXAMPLE: POTENT INHIBITION OF RSV USING 2-5A-ANTISENSE CHIMERA TARGETED TO THE VIRUS GENOME

The following example demonstrates the efficacy of the 2-5A activator-antisense complexes of the present invention designed to target the genomic strand of RSV RNA genome. In particular, the conserved sequences that occur in gene-start, and gene-end signals have been targeted. The antisense cassettes have been modified with phosphorothioates in order to improve stability of the antisense cassette. In particular, the phosphorothioate G quartet motif has been modified to produce an ideal 2-5-A antisense structure.

10.1 MATERIALS AND METHODS

SYNTHESIS PROCEDURE

The 2-5A-antisense chimeras were synthesized by a fully automated procedure. All solid chemicals were dried over $P_2O_5$ in vauco overnight before use. The 1 µmole deoxynucleoside-lcaa-CPG column was used.

The 2-5A-antisense chimera denotes the complete 2-5A-antisense chimera minus the 5'-terminal monophosphate group and has three regions defined for synthetic purposes: and antisense region, a linker region, and the (2',5')-oligoadenylate region and a 5'-monophosphate or region. One µmole scale standard synthesis cycles were used. The 2-5A-antisense chimera was synthesized by a fully automated method listed in Table 2. The cycles were modified by changing the coupling wait times (for coupling of monomer amidites) fore each different region. For preparation of core 2-5A-antisense chimeras without a 5'-monophosphate or 5'-monophosphorothioate group.

The 2-5A-antisense chimera also has variable numbers of phosphorothioate linkages contained within the oligonucleotide backbone. For synthesis of phosphodiester internucleotide linkages within the chimera, the synthetic cycle in Table 2 was used. For synthesis of the phosphorothioate internucleotide linkages within the chimera, the synthetic cycle in Table 2 was used.

Cleavage and Deprotection

1. The oligonucleotide was cleaved from the CPG support by concentrated ammonium hydroxide/ethanol (3:1,v/v) at room temperature for 2 hours.

2. The ammonium hydroxide/ethanol solution of crude oligonucleotide was placed into a 3 mL vial and sealed tightly. The solution was heated at 55° C. for 8 hours to remove the protecting groups on the bases.

3. The ammonium hydroxide/ethanol solution of oligonucleotide was transferred to a glass tube, and cooled at 0° C. The solution was ten evaporated to dryness in a speedvac concentrator and a solution of tetrabutylammonium fluoride (2 mL, 1.0M) in dry THF was added, and the entire mixture was vortexed for at least 1 min. This reaction mixture was allowed to incubate at room temperature for 24 hours.

An equivalent volume of 0.1 TEAA (tetraethylammonium acetate) (pH 7.0) buffer was added, mixed and evaporated to half volume to remove the majority of the THF. The residue was subjected to purification by HPLC.

Purification of the 2-5A-Antisense Chimeras

1. Polystyrene Reverse-Phase Ion-Pair Chromatography (PRP-IPC) Protocol (27) (Swiderski et al. 1994 Analytical Biochemistry 216:83–88.)

The oligonucleotide was dissolved in about 4–5 mL water to make a clear solution (centrifuged if necessary), and this solution was directly injected into the PRP-1 HPLC column (300×7 mm). The reaction mixture was thus simultaneously desalted and purified.

Solvent A: 10 mM tetrabutyl ammonium phosphate (TBAP), Ph 7.5 in water.
Solvent B: 10 mM TBAP, pH 7.5 in acetonitrile/water (8:2, v/v).

The sample was eluted with a convex gradient of 5–95% solvent B in A in 45 min. at a flow rate of 1.5 mL/min. Fractions containing desired oligo were pooled and evaporated to about 1–2 mL.

Excess TBAP was removed from the purified oligonucleotide according to the following procedure. Desalting took place by passing the oligonucleotide solution through a C-18 Sep-Pac cartridge.

a. The C-18 cartridge was pre-washed with 10 mL methanol and 10 mL water.

b. The oligo solution was loaded onto the cartridge at a 1 drop/sec flow rate.

c. The cartridge was washed with 20 mL water to remove salt from the column.

d. The oligonucleotide was eluted with 20 mL of acetonitrile:methanol:water (1:1:1, v/v/v).

e. The desalted oligonucleotide was detected by UV spectrophotometer and the fractions containing oligo were combined and concentrated.

The oligo-TBA ion-pair was converted into its sodium salt form by the following procedure. One m: of Dowex 50W ion exchange wet resin $Na^+$ form) was added to oligonucleotide/water solution. The solution was kept at 4° C. for three hours. The resin was removed by passing the solution through a Poly-Prep chromatography column (Bio-Rad, Cat # 731-1550). The resin was washed with extra water until no oligonucleotide remained on the resin.

Dialysis of the 2-5A-Antisense Chimeras

After purification by HPLC and ion exchange, the oligonucleotide ($Na^+$ salt) was dialyzed to remove small molecules and excess salt. The dialysis was carried out at 4° C. The oligonucleotide was dialyzed against 0.02 M NaCl first for 4–6 hours and then against water for 48 hours.

Post-treatment of 2-5A-Antisense Chimeras

The oligonucleotide, after dialysis, was passed through a 0.22 µM Millex GV filter unit (Millipore Cat. No. SLGV025LS) for sterilization. The resulting solution was quantitated as O.D. $A_{260}$ by UV/V is spectrophotometry.

Oligonucleotide Purity Confirmation

The purities of 2-5A-antisense chimeras were checked by HPLC or gel capillary electrophoresis (CGE). The purity was obtained by the integration of peak area detected at 260 nm.

1. Capillary Gel Electrophoresis (CGE) Method.

The measurement of oligonucleotide purity was performed on an Applied Biosystems 270A-HT capillary electrophoresis instrument using MICRO-GEL$_{100}$ (Applied Biosystems Inc.) gel filled capillaries (50 uM i.d., effective length 27 cm, running buffer, 75 mM Tris phosphate (pH 7.6), 10% methanol). Detection was at 260 nm. A typical electropherogram of a 2-5A-antisense chimera was obtained by the use of the following conditions: sample concentration of approximately 0.1 O.D./mL, electrokinetic injection during 2 s at −5 kEv. Voltage was −14 mA (19mA) and the operation temperature was 30° C. Under these conditions, the 2-5A-antisense chimeras had about a 1 min. earlier elution time than that of its core analogue, the latter of which corresponds to the n-1 synthetic failure sequence.

2. Dionex PA-100 Ion Exchange HPLC Method.

The purities of oligonucleotides could also be measured by a Dionex ion exchange HPLC. Usually, the Dionex PA-100 ion exchange column could provide higher resolution and better peak shape compared with other HPLC chromatographic methods for the analysis of 2-5A-antisense chimeras.

A typical chromatogram of a 2-5A-antisense chimera was obtained by the use of the following conditions: Dionex PA-100 (4×250 mm) column (Dionex Cat # 43010). Solvent A was 25 mM Tris/HCI and 0.5% acetonitrile (pH 7.0), solvent B was 25 mM Tris/HCI, 0.5% acetonitrile and 1 M ammonium chloride (pH 7.0). The sample was eluted in linear gradient of 10–70% B in A during 30 min. followed by isocractic conditions for 10 min. at a flow rate of 1 mL/min. Detection was at 260 nm.

Cells and Virus

Embryonic African green monkey kidney cells (MA-104) were obtained from BioWhittaker, Inc. (Walkersville, Md.).

HEp-2 cells were propagated from a human epidermoid carcinoma of the larynx (American Type Culture Collection, ATCC; Rockville, Md.). The cells were grown in minimal essential medium. (MEM, Gibco-BRL, Gaitherburg, Md.) supplemented with 0.1% $NaHCO_3$ and 10% fetal bovine serum (FBS, Hyclone Laboratories, Logan Utah.). When performing antiviral assays, serum was reduced to 2% and 50 μg/ml gentamicin (Sigma Chemical Company, St. Louis, Mo.) was added to the medium.

Respiratory syncytial virus (RSV) strains A2 and Long were acquired from ATCC.

Cytopathic Effect (CPE) Inhibition Assay

The CPE inhibition assay used in this study was performed as described by Sidwell and Huffman (Sidwell et al., 1971, Appl. Microbiol. 22:7979–7801) with slight modifications. Varying concentrations of test compounds were added to each plate containing near confluent cell monolayers ($1 \times 10^5$ cells/well) followed immediately by the addition of virus at a multiplicity of infection (MOI)=0.01, and then incubated at 37° C. On the following day, the medium from each plate was removed and fresh compound added. The assay was stopped at the end of the sixth day when the virus cytopathic effect in the virus infected, untreated control cells affected all cells. All compounds were assayed for virus inhibition in quadruplicate and for cytotoxicity in duplicate. For each compound, two wells were set aside as uninfected, untreated cell controls per test and four wells per test received virus only and represented controls for virus replication. Changes due to viral cytopathic effect were graded on a scale of 1–4, grade 4 representing a scenario in which the entire (100%) monolayer in a well showed viral cytopathic effect. For all CPE-based assays, the 50% effective concentration ($EC_{50}$) was calculated by regression analysis using the means of the CPE ratings at each concentration of compound.

Morphological changes due to compound cytotoxicity were graded on a scale of 0–5; grade 5 was defined as 100% cytotoxicity. The 50% cytotoxic dose ($IC_{50}$ was calculated by regression analysis. A selective index (S.I.) was calculated for each compound [S.I.=$(IC_{50})/(EC_{50})$].

Neutral Red Assay (NR) of CPE Inhibition and Cytotoxicity

This assay was performed by a modified method as described by Cavenaugh et al. (Cavenaugh et al. 1990, Invest. New Drugs 8:347–354). Briefly, medium was removed from each well of a plate scored for CPE from a CPE inhibition assay, 0.2 ml of neutral red (0.034% in PSS) was added to each of the wells of that plate and the plate incubated for 2 hr at 37° C. in the dark. The neutral red solution was removed from the wells and the wells rinsed twice with PBS (pH 7.4). Equal volumes (0.1 ml) of absolute ethanol and Sörenson citrate buffer (0.1 M sodium citrate, 0.1 M HCI, pH 4.2) were mixed together and added to each well. Plates were incubated in the dark for 30 min. at room temperature to solubilize the dye. The plates were then gently mixed on a 96-well plate adapted vortexer for 1 min. Absorbances at 540 nm and 450 nm were read with a microplate reader (Bio-Tek EL 1309; Bio-Tek Instruments, Inc. Winooski, Vt.). Absorbance values were expressed as percents of untreated controls and EC50 and IC50 values were calculated by regression analysis.

10.2 RESULTS

Using the 2-5A-antisense strategy the genomic strand of RSV has been targeted, and most specifically, the conserved sequences that occur in gene-start, intragenic, and gene-end signals were targeted. To illustrate this approach, the antisense cassette of the 2-5A-antisense chimera: 5'AAA AAT GGG GCA AAT AA3' (SEQ ID NO:13) was used. This 17-mer targets a number of sequences that occur within the critical gene-end-intragenic-gene-start signals of the RSV genomic RNA.

The first oligonucleotide synthesized was an all phosphorothioate 17-mer with the consensus sequence described above (Table 8). This material (MP273) was able to inhibit RSV replication in HEP-2 cells ($EC_{50}$=3 μM) with low toxicity ($IC_{50}$>10 μM). However, this all PS oligonucleotide contained a G quartet motif. Therefore, as a control, a second all PS oligonucleotide (MP317) was prepared that still contained the G quartet motif, but which was otherwise scrambled so as not to match the target sequence but which retained the same overall nucleotide composition. This material (MP317) proved also to have significant antiviral activity ($EC_{50}$=1 μM) and detectable toxicity ($IC_{50}$=5 μM). Since this sequence did not match any within the RSV genome or RSV mRNA, it was concluded that the observed antiviral activity was not a true antisense effect, but was rather related to the G quartet-containing phosphorothioate oligonucleotide. (Ojwang et al., 1995 in Anti Microb Agents Chemo 39: 24; Burgess et al., 1995 PNAS 92:4051) In accord with this conclusion, the toxicity (non-specificity) of this oligonucleotide was significant. Finally, an all phosphorothioate oligonucleotide (MP318) was prepared in which the entire nucleotide sequence was scrambled. This alteration caused a tenfold drop in anti-RSV activity ($EC_{50}$=10 μM) which was not specific ($IC_{50}$=8 μM). Thus, a significant non-antisense effect would be inherent in any all PS oligonucleotide containing the 17-mer consensus sequence, and this effect was related to the presence of the PS G-quartet.

TABLE 8

2-5A-Antisense Chimerase
Targeting the RSV Genome (−) RNA

| OLIGO | | SEQUENCE | $EC_{50}$ | $IC_{50}$ |
|---|---|---|---|---|
| allPS | MP273 (SEQ ID NO: 8) | AsAsAsAsAsTsGsGsGsGsCsAsAsAsT sAsA | 3 | >10 |
| allPS | MP317 (SEQ ID NO: 30) | AsTsAsAsGsGsGsGsAsAsCsAsTsAsA sAsA | 1 | 5 |
| G4 Scr allPS, Scr | MP318 (SEQ ID NO: 31) | GsAsAsGsAsCsAsGsAsAsTsAsAsGsA sTsA | 10 | 8 |
| Gapmer | MP320 (SEQ ID NO: 8) | AsAsAsAsAATGGGGCAAAsTsAsA | 10 | >10 |
| 2-5A-Gapmer | MP351 (SEQ ID NO: 8) | 2-5A-$L_2$-AsAsAsAATGGGGCAAAsTsAsA | 0.3 | >10 |

$EC_{50}$ Concentration for 50% inhibition of virus replication (microM)
$IC_{50}$ Conc. for 50% cytotoxicity grade by morphological change (microM)
Determined in MA-104 cells, A2 strain RSV
L in this table refers to the standard linker, 1,4-butanediolphosphate, used in 2-5A antisense formulations.

To reduce the non-antisense (and nonspecific antiviral effect) associated with the all PS 17-mer, the extent of sulfur substitution was dramatically reduced and the G quartet motif was completely changed from PS to PO. Only three internucleotide linkages at both the 5'- and 3'-termini of the antisense oligonucleotide were thiophosphorylated. The resulting antisense oligonucleotide (MP320) possessed a significantly reduced anti-RSV activity compared to MP273 and was of low toxicity. This antisense cassette was then used to construct a 2-5A-antisense chimera (MP351) with the identical antisense sequence and structure. This addition of 2-5A to the parent antisense molecule (MP351) resulted in a 33-fold increase in anti-RSV activity (Table 8).

When this 2-5A-antisense composition was examined in a virus yield reduction assay (Table 9) in comparison to the accepted anti-RSV drug, ribavirin, it showed an $EC_{50}$ of 0.32 μM compared to an $EC_{50}$ of 40 μM for ribavirin. In addition, the $EC_{90}$ for MP351 was 1 μM and that for ribavirin was 80 μM. Thus, this novel anti-RSV 2-5A-antisense chimera was 80–125 times more potent than ribavirin when assayed in human HEp-2 cells.

TABLE 9

Virus Yield Reduction Assay
HEp-2 Cells
MP351
2-5A-L2-AsAsAsAATGGGGCAAAsTsAsA (SEQ ID NO: 13)

| Compound | EC50 | EC90 |
|---|---|---|
| MP351 | 0.32 μM | 1 μM |
| ribavirin | 40 μM | 80 μM |

$EC_{50}$ & $EC_{90}$: concentration required to reduce virus (RSV strain A2) replication by 50% and 90%, respectively.
Both compounds were added to the cells twice daily.

In a separate experiment, two additional questions were addressed. The first question asked was whether or not this was a true antisense effect. Thus, the nucleotide sequence antisense domain of the active MP351 2-5A-antisense chimera as scrambled (MP426), while the nucleotide composition was aintained. The 2-5A-antisense control sequence was sp(5'A2')$_4$BupBupd (GsAsTsAGAAATAGAAAsGsCsA)(SEQ ID NO:32), the exact same overall structural pattern as MP351 with only the nucleotide sequence varied. As shown in Tables 10 and 11, this resulted in a large decrease in anti-RSV activity, regardless of the dosage regime. The parallel study of the effects of frequency and duration of chimera administration revealed that MP351 could be administration to the cells only once on day 1 after infection in order to obtain a significant antiviral effect. However, MP351 showed the most potent effects when given once a day for three days or twice a day for two days.

TABLE 10

Effects Of Frequency And Duration Of
Compound Administration On The RSV Inhibitory Properties
Of MP426, & 351: CPE Inhibition Assay

| | Compound (μM) | | | | | | | | |
|---|---|---|---|---|---|---|---|---|---|
| Dura- | MP 426 | | | MP 351 | | | Ribavirin | | |
| tion | $EC_{50}$ | $IC_{50}$ | SI | $EC_{50}$ | $IC_{50}$ | SI | $EC_{50}$ | $IC_{50}$ | SI |
| q.d.[a] | | | | | | | | | |
| 1 day[b] | >3.2 | >3.2 | 0 | 0.1 | >3.2 | 32 | 4.0 | 230 | 57 |
| 3 days | 3.2 | >3.2 | >1 | 0.02 | >3.2 | >160 | <4.0 | 230 | >57 |
| 4 days | 1.0 | >3.2 | >3.2 | 0.1 | >3.2 | >32 | <4.0 | 230 | >57 |
| B.I.D.[c] | | | | | | | | | |
| 2 days | 0.1 | >3.2 | >32 | 0.03 | >3.2 | >107 | <4.0 | 230 | >57 |
| 3 days | 0.2 | 3.2 | 16 | 0.04 | >3.2 | >80 | <4.0 | 720 | >180 |
| 4 days | 1.0 | 3.2 | 3.2 | 0.3 | 3.2 | 11 | 4.0 | 230 | 57 |

[a]q.d. = Compound was replenished once a day.
[b]Compound was added along with virus and was never removed or replenished.
[c]B.I.D. = Compound was replenished twice daily, approximately eight hours apart.
The experiments were conducted in HEp2 cells with RSV strain A2.

TABLE 11

Effects Of Frequency And Duration Of Compound Administration
On The RSV Inhibitory Properties Of MP426, & 351:
Neutral Red Uptake Assay

| | Compound (μM) | | | | | | | | |
|---|---|---|---|---|---|---|---|---|---|
| Dura- | MP 426 | | | MP 351 | | | Ribavirin | | |
| tion | $EC_{50}$ | $IC_{50}$ | SI | $EC_{50}$ | $IC_{50}$ | SI | $EC_{50}$ | $IC_{50}$ | SI |
| q.d.[a] | | | | | | | | | |
| 1 day[b] | >3.2 | >3.2 | 0 | 0.1 | >3.2 | 32 | 4.0 | 480 | >120 |
| 3 days | >3.2 | 3.2 | 0 | 0.05 | 2.0 | 40 | 8.0 | 1010 | 126 |
| 4 days | >3.2 | 3.2 | 0 | 0.1 | >3.2 | >32 | 20 | 730 | 36 |
| B.I.D.[c] | | | | | | | | | |
| 2 days | 0.3 | >3.2 | >11 | 0.03 | 3.2 | >107 | 8.0 | 1050 | 130 |
| 3 days | 1.0 | 3.2 | 3.2 | 0.1 | >3.2 | >32 | <4.0 | 700 | >175 |
| 4 days | >3.2 | 3.2 | 0 | 0.3 | 3.2 | 11 | 8.0 | 600 | 75 |

[a]q.d. = Compound was replenished once a day.
[b]Compound was added along with virus and was never removed or replenished.
[c]B.I.D. = Compound was replenished twice daily, approximately eight hours apart.
The experiments were conducted in HEp2 cells with RSV strain A2

In a separate experiment, the anti-RSV activity of MP351 was examined in MA-104 cells which are a line of embryonic African Green monkey cells. MP351 inhibited RSV strain A2 replication in MA104 cells with an $EC_{50}$ of 1 μM by CPE assay and 0.2 μM by neutral red dye uptake assay. MP351 needed to be added only once or once daily for 2 days to achieve this effect. Thus, MP351 showed potent anti-RSV activity in monkey as well as human cells.

The anti-RSV activity of MP351 against other strains of RSV is assayed in human HEp-2 cells (Table 12) MP351 showed slightly varying inhibitory activities against other RSV strains; nonetheless, MP351 was a potent inhibitor of representative members of both A and B strains of RSV as well as a clinical isolate.

TABLE 12

Inhibition Of RSV Strains Replicating In HEp-2 cells by MP 351

| Virus | Cytopathic Effect Inhibition Assay | | | | | | Neutral Red Uptake Assay | | | | | |
|---|---|---|---|---|---|---|---|---|---|---|---|---|
| | MP 351 | | | Ribavirin | | | MP 351 | | | Ribavirin | | |
| IC50 | $EC_{50}$ | $IC_{50}$ | SI | $EC_{50}$ | $IC_{50}$ | SI | $EC_{50}$ | $IC_{50}$ | SI | $EC_{50}$ | $IC_{50}$ | SI |
| CH18537 (B) | 0.1 | >3.2 | >32 | 4 | 208 | 52 | 0.1 | 2.4 | 24 | 12 | 233 | 19 |
| Long (A) | 0.3 | >3.2 | >10 | 12 | 205 | 17 | 0.4 | 2.0 | 5 | 12 | 280 | 23 |
| 393 (clinical isolate) | 0.3 | >3.2 | >10 | 4 | 96 | 24 | 1.6 | >3.2 | >2 | 4 | 96 | 24 |

In this series, MP351 was added once a day for two days with fresh medium change.

The results of multiple administrations of MP351 in HEp-2 cells on anti-RSV activity are shown in Table 13. MP351 was most inhibitory to RSV replication when added once a day up to two days post infection for a total of three doses (Table 13). However, significant efficacy was also achieved when it was added only one or twice to infected cell cultures.

TABLE 13

Effects of multiple administrations (q.d.a) of compound ($\mu$M) on the RSV inhibitory properties of MP 351 CPE inhibition assay and neutral red uptake

| | Cytopathic Effect Inhibition Assay | | | | | | Neutral Red Uptake Assay | | | | | |
|---|---|---|---|---|---|---|---|---|---|---|---|---|
| | MP 351 | | | Ribavirin | | | MP 351 | | | Ribavirin | | |
| Time | $EC_{50}$ | $IC_{50}$ | SI | $EC_{50}$ | $IC_{50}$ | SI | $EC_{50}$ | $IC_{50}$ | SI | $EC_{50}$ | $IC_{50}$ | SI |
| Day 0[b] | 0.1 | >3.2 | >32 | 12 | 240 | 30 | 0.2 | >3.2 | >16 | 12 | 328 | 27 |
| Day 1[c] | 0.1 | >3.2 | >32 | 4 | 320 | 8 | 0.32 | >3.2 | >10 | 40 | 1130 | 28 |
| Day 2[c] | 0.03 | 2.2 | 73 | 4 | 320 | 80 | 0.01 | 2.2 | 220 | 4 | 320 | 80 |

[a]q.d. = one dose per day.
[b]Compound was added immediately after virus exposure to cells.
[c]Compound and any supernatant virus was removed and fresh compound in test medium added on the day indicated post infection.

10.3 CONCLUSIONS

The present disclosure documents an approach, using 2-5A-antisense, that permits an antiviral strategy with the RSV genomic RNA (or minus RNA) as target. The 2-5A-antisense strategy has been used to target specifically repeated critical consensus regions in the respiratory syncytial virus genomic RNA. The result is a highly active 2-5A-antisense chimera which has approximately 100 times the anti-RSV potency of the presently employed therapeutic, ribavirin. It shows potent activity in both human and monkey cells, and against other strains (both A and B) of RSV. It is potently active with only a single administration in tissue culture. This finding represents an innovative approach to the control of respiratory syncytial virus infection.

The present invention is not to be limited in scope by the specific embodiments described which are intended as single illustrations of individual aspects of the invention, and any constructs, viruses or enzymes which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

TABLE 2

Synthesis Procedure for 5'-Terminal Phosphorylation

| Step | Solvent/reagent | Time | Volume |
|---|---|---|---|
| 1. coupling | 0.2 M phosphorylation reagent in tetrazole/acetonitrile | 3 min. | 0.15 mL |
| 2. washing | acetonitrile | | 3 mL |
| 3. drying | argon | 3 min. | |
| 4. oxidation | 0.1 M I2 in lutidine:THF:water (20:80:1) | 0.75 min. | 1 mL |
| 5. washing | acetonitrile | | 3 mL |
| 6. drying | argon | 3 min. | |
| 7. detritylation | 3% TCA in CH2Cl2 | 1.5 min. | 1 mL |
| 8. washing | 2% Py in acetonitrile | | 1 mL |
| 9. washing | acetonitrile | | 3 mL |

TABLE 3

Antiviral activities of chimeric antisense against RSV L polymerase RNA translation start site.

| Oligo/(site in RSV RNA) | Structure of Compounds [oligonucleotide]/treatment): | % Inhibition of RSV replication | | |
|---|---|---|---|---|
| | | 3.3 μM | 6.6 μM | 9.9 μM |
| $A_4$-antiRSV3'-3'C/(8490–8509) (SEQ ID NO: 32) | A2'p(A2'p)$_3$-[(Bu)p]$_2$-(5'aat ggg atc cat ttt gtc c3'-3'c5') | | 20 (1) | 28.3 (3) |
| p$A_4$-antiRSV/(8490–8509) (SEQ ID NO: 33) | pA2'p(A2'p)$_3$-[(Bu)p]$_2$-(5'aat ggg atc cat ttt gtc cc3') | 3 (2) | 38.8 (4) | 64.8 (5) |
| p$A_4$-3'antiRSV5'/(8490–8509) (SEQ ID NO: 33) | pA2'p(A2'p)$_3$-[(Bu)p]$_2$-(3'ccc tgt ttt acc tag ggt aa5') | | | 69 (1) |
| p$A_4$-antiRSV3'-3'C/(8490–8509) (SEQ ID NO: 33) | pA2'p(A2'p)$_3$-[(Bu)p]$_2$-(5'aat ggg atc cat ttt gtc c3'-3'c5') | 2 (1) | 64.3 (3) | 74 (2) |
| spA4-antiRSV/(8490–8509) (SEQ ID NO: 33) | spA2'p(A2'p)$_3$-[(Bu)p]$_2$-(5'aat ggg atc cat ttt gtc cc3') | 16.5 (2) | 71 (1) | 94 (1) |

Antiviral activity as determined by virus plaque assay at 36 hrs post-infection. In parentheses, are the number of times the experiments were done to produce the data. Results shown are the average of the percent inhibition data from 2 to 7 experiments, except for single experiment data. Percent inhibition is defined as [(infectious virus particles produced in oligonucleotide treated cells)/(infectious virus particles produced in untreated cells)] × 100. M.O.I. was 2.0 p.f.u. per cell.
Chimeric 2-5A-antisense oligonucleotides are abbreviated according to the following convention employed herein for added clarity. The 2-5A domain of the chimera is indicated in bold-face capitalized type; i.e., pA2'p(A2'p)$_3$. The linker moiety is abbreviated as [(Bu)p]$_2$ which stands for two 1,4-butanediol molecules linked through phosphodiester bonds to each other and the 2-5A and antisense domains of the chimera; i.e.,-[(Bu)p]$_2$. The antisense oligonucleotide is represented in lower case bold-face type in triplet repeats with normal 3',5' phosphodiester linkages in the polarity shown; i.e., (3'ccc tgt ttt acc tag ggt aa5'). Exceptions include the inversion of polarity for the entire chain or for the terminal 3'-nucleotide, both of which are clearly indicated. When the 5'-monophosphate of the 2-5A domain of the chimera was modified to the 5'-thiophosphate, the abbrevation used is spA2'p(A2'p)$_3$.

TABLE 4

Antiviral activities of stabilized chimeric antisense against different sites in RSV M2 and L mRNAs.

| Oligo/(site in RSV RNA) | Structure of Compounds [oligonucleotide]/treatment): | % Inhibition of RSV replication | | |
|---|---|---|---|---|
| | | 3.3 μM | 6.6 μM | 9.9 μM |
| sp$A_4$-antiRSV3'-3'N Series: | | | | |
| sp$A_4$-antiRSV3'-3'A/(8530–8547) (SEQ ID NO: 34) | spA2'p(A2'p)$_3$-[(Bu)p]$_2$-(5'cta tcg gtt aga taa ac3'-3'a5') | 2.5 (1) | | |
| sp$A_4$-antiRSV3'-3'G/(8599–8618) (SEQ ID NO: 35) | spA2'p(A2'p)$_3$-[(Bu)p]$_2$-(5'gat aag gac cat tga ata t3'-3'g5') | 44 (1) | | |
| sp$A_4$-antiRSV3'-3'C/(8561–8578) (SEQ ID NO: 36) | spA2'p(A2'p)$_3$-[(Bu)p]$_2$-(5'ctc tga gaa aga gat aa3'-3'c5') | 57 (1) | | |
| sp$A_4$-antiRSV3'-3'T/(8261–8279) (SEQ ID NO: 37) | spA2'p(A2'p)$_3$-[(Bu)p]$_2$-(5'gat tga aat ata gtg tgt3'-3't5') | 78 (2) | 87 (1) | 87 (1) |
| sp$A_4$-antiRSV3'-3'A/(8251–8270) (SEQ ID NO: 38) | spA2'p(A2'p)$_3$-[(Bu)p]$_2$-(5'ata gtg tgt tct ttt gat t3'-3'a5') | 86.7 (2) | 92 (1) | |
| sp$A_4$-antiRSV3'-3'T/(8281–8299) (SEQ ID NO: 39) | spA2'p(A2'p)$_3$-[(Bu)p]$_2$-(5'atg gtt att tgg gtt gtt3'-3't5') | 91.3 (3) | 97 (1) | 99.6 (1) | see legend to Table 3.

TABLE 5

ANTIVIRAL ACTIVITY of spA4-antiRSV3'-3'T/(8281)
Hep-2 Cells
Neutral Red

| Compound | $EC_{50}$ | $IC_{50}$ | SI |
|---|---|---|---|
| spA4-antiRSV3'-3'T/(8281) | 0.3 μM | >10 μM | >33 |
| Ribavirin | 4 μM | 41 μM | 10 | determined with RSV strain A2, MOI = 0.005
Fresh medium and oligo or ribavirin added twice daily for 4 d and test read on d 5.
$EC_{50}$ effective concentration to reduce RSV-induced CPE by 50%.
$IC_{50}$ 50% inhibitory concentration for cytotoxicity to cells (visual and dye uptake as determined in rapidly dividing cells as opposed to stationary cells used for viral assays.
SI selectivity index = $IC_{50}/EC_{50}$

TABLE 6

ANTIVIRAL ACTIVITY of spA4-antiRSV3'-3'T/(8281)
MA-104 Cells
Visual CPE and Virus Yield Reduction

| Compound | $EC_{50}$ | $EC_{90}$ | $IC_{50}$ | SI |
|---|---|---|---|---|
| spA4-antiRSV3'-3'T/(8281) | 0.02 μM | 0.02 μM | >10 μM | >500 |
| Ribavirin | 1 μM | 7 μM | 210 μM | 210 | as determined with RSV strain A2, MOI = 0.005
Fresh medium and oligo or ribavirin added twice daily for 4 d and test read on d 5.
$EC_{50}$ effective concentration to reduce RSV-induced CPE by 50%.
$EC_{90}$ effective concentration to reduce RSV yield by 90%.
$IC_{50}$ 50% inhibitory concentration for cytotoxicity to cells (visual and dye uptake as determined in rapidly dividing cells as opposed to stationary cells used for viral assays.)
SI selectivity index = $IC_{50}/EC_{50}$

REFERENCES

Beigelman, L., Matulic-Adamic,j., et al., Synthesis and biological activities of a phosphorodithioate analog of 2-5A. Nucleic Acid Research 23:3989–94.

Balotta, C, Lusso, P., Crowley, R., Gallo, R C, Franchini, G. 1993. Antisense phosphorothioate oligodeoxynucleotides targeted to the vpr gene inhibit human immunodeficiency virus type 1 replication in primary human macrophages. J. Virology, 67: 4409–4414.

Chebath, J., Benech, P., Revel, M and Vigneron, M. 1987. Constitutive expression of (2'-5') oligo A synthetase confers resistance to picornavirus infection. Nature 330, 587–588.

Cirino, N M, Panuska, J R, Villani, A, Taraf, H, Rebert, N A, Merolla, R, Tsivitse, P, Gilbert, I A. 1993. Restricted replication of respiratory syncytial virus in human alveolar macrophages. J Gen Virol 74:1527–1537.

Floyd-Smith, G, Slattery, E. and Lengyel, P. 1981. Interferon action: RNA cleavage pattern of a (2'-5') oligoadenylate-dependent endonuclease. Science 212: 1020–1032.

Freier, S M, Kienzek, R, Jaegar, J A, Sugimoto, N, Caruthers, M H, Neilson, T, and Turner, D H. 1986. Improved free-energy parameters for predictions of RNA duplex stability. 1989. Proc Natl Acad Sci USA 83:9373–9377.

Froelich, E. A. 1994. SPI Pharmaceuticals, Inc.—Company Report, Pershing Division—Donaldson, Lufkin & Jenrette.

Goodchild, J, Agrawal, S, Civeira, M P, Sarin, P S, Sun, D, Zamecnik, P C. 1988. Inhibition of human immunodeficiency virus replication by antisense oligodeoxynucleotides. Proc. Natl. Acad. Sci. USA. 85: 5507–5511.

Gribaudo, G, Lembo, D, Cavallo, G, Landolfo, S, and Lengyel, P. 1991. Interferon action: binding of viral RNA to the 40-kilodalton 2'-5' oligoadenylate synthetase in interferon-treated HeLa cells infected with encelphalomyocarditis virus. J Virol 65, 1748–1757.

Gruenert, D C, Basbaum, C B, Welsh, M J, Li, M, Finkbeiner, W E, Nadel, J A. 1988. Characterization of human tracheal epithelial cells transformed by an origin defective simian virus 40. Proc Nat Acad Sci, USA. 85: 5951–5955.

Hassel, B, Zhou, A, Maran, A, Silverman, R H. 1993. A dominant negative mutant of 2-5A-dependent RNase suppresses antiproliferative and antiviral effects of interferon, The EMBO Journal 12, 3297–3304.

Heilman, C. 1994. RFA: "Mechanism of RSV vaccine immunopotentiation". N.I.A.I.D., N.I.H., Bethesda, Md.

Lesiak, K.; Khamnei, S.; Torrence, P. F. 1993. 2',5'-Oligoadenylate-antisense chimeras-synthesis and properties. Bioconjugate Chem, 4: 467–472.

Letsinger, R L, Zhang, G, Sun, D K, Ikeuchi, T, Sarin, P S. 1989. Cholesteryl-conjugated oligonucleotides: Synthesis, properties, and activity as inhibitors of replication of human immunodeficiency virus in cell culture. Proc Natl Acad Sci 86: 6553–6556.

Maran, A, Maitra, R K, Kumar, A, Dong, B, Xiao, W, Li, G, Williams, Brg, Torrence, P F, Silverman, R H. 1994. Blockage of NF-kB signaling by selective ablation of an mRNA target by 2-5A-antisense chimeras. Science 265:789–792.

Maitra, R K, Li, G, Xiao, W, Dong, B, Torrence, P F, and Silverman, R H. 1995. Catalytic cleavage of an RNA target by 2-5A-antisense and 2-5A dependent RNase. J. Biol.Chem., 270: 15071–15075.

McIntosh, K, and Chanock, R M. 1990. Respiratory syncytial virus. In Virology, 2nd edition. Edited by B N Fields, D M Knipe et al., Raven Press, Ltd, New York, pp. 1045–1072.

Merolla, R, Rebert, N A, Tsivitse, P, Hoffmann, S P, Panuska, J R. 1995. Respiratory syncytial virus replication in human lung epithelial cells: inhibition by tumor necrosis factor-a and interferon-a8247. Am J Rsp and Crit Care Med.

Midulla, F, Villani, A, Panuska, J R, Dab, I, Kolls, J K, Merolla, R, Ronchetti, R. 1993. Concise Communication: Respiratory syncytial virus lung infection in infants: Immunoregulatory role of infected alveolar macrophages. J Inf Dis 168: 1515–1519.

Panuska, J R, Hertz M I, Taraf, H, Villani, A, Cirino, N M. 1992. Respiratory syncytial virus infection of alveolar macrophages in adult transplant patients. Am Rev Resp Dis 145: 934–939.

Panuska, J R, Merolla, R, Rebert, N A, Hoffmann, S P, Tsivitse, P, Cirino, N M, Silverman, R H, Rankin, J A. 1995. Respiratory syncytial virus induces interleukin 10 by human alveolar macrophages: suppression of early cytokine production and implications for incomplete immunity. submitted to J Clin Invest).

Rysiecki, G, Gewert, D R, Williams, Brc. 1989. Constitutive expression of a 2',5'-oligoadenylate synthetase cDNA results in increased antiviral activity and growth suppression. J Interferon Res 9, 649–657.

Salser, W. 1977. Globin mRNA sequences: analysis of base pairing and evolutionary implications. Cold Spring Harbor Symposium on Quantitative Biology 42:985–1002.

Silverman, R H. 1994. Fascination with 2-5A-Dependent RNase: A unique enzyme that functions in interferon action. J Interferon Res, 14:101–104.

Swiderski, P M, Bertrand, E L, and Kaplan, B E (1994) Polystyrene reverse-phase ion-pair chomatography of chimeric ribozymes. Analytical Biochemistry, 216: 83–88.

Torrence, P F, Maitra, R K, Lesiak, K, Khamnei, S, Zhou, A, and Silverman, R H. 1993. Targeting RNA for degradation with a 2',5'-oligoadenylate-antisense chimera. Proc.Natl Acad Sci USA, 90: 1300–1304.

Wreschner, D H, James, T C, Silverman, R H, and Kerr, I M. 1981. Ribosomal RNA cleavage, nuclease activation and 2-5A(ppp(A2'p)nA) in interferon-treated cells. Nucleic Acids Res. 9, 1571–1581.

Wreschner, D H, McCauley, J W, Skehel, J J, and Kerr, I M. 1981. Interferon action-sequence specificity of the ppp (A2'p)nA-dependent ribonuclease. Nature 289, 414–417.

Xiao, W, Li, G, Lesiak, K, Dong, B, Silverman R H, and Torrence, P F. 1994. Synthesis of a 5'-thiophosphate analogue of 2-5A, a phosphatase resistant activator of the 2-5A dependent ribonuclease. Bioorganic & Med. Chem. Letts: 4, 2609–2614, 1994.

Zamecnik, P C, Goodchild, J, Taguchi, Y, Sarin, P S. 1986, Inhibition of replication and expression of human T-cell lymphotropic virus type III in cultured cells by exogenous synthetic oligonucleotides complementary to viral RNA. Proc Natl Acad Sci USA. 83: 4143–4146.

Zisson, A. 1993. Shaman Pharmaceuticals, Inc.—Company Report. Hambrecht & Quest Institutional Research—Company Report.

Zuker, M. 1989. Computer prediction of RNA structure. Methods in Enzymology 180:262–288.

We claim:

1. A composition comprising:
   a) an oligonucleotide, comprising at least one 2'O methyl nucleotide, in which the oligonucleotide is complementary to between 15 and 20 nucleotides of a conserved gene-start or gene-end-signal of a genomic RNA strand of a Respiratory Syncytial Virus and a terminus of the oligonucleotide is attached to a linker; and
   b) an activator of RNase L attached to the linker.

2. The composition of claim 1 in which the activator is selected from the group consisting of sp5'A2'(p5'A2')$_2$—O—, sp5'A2'(p5'A2')$_3$—O—, p5'A2'(p5'A2')$_2$—O—, and p5'A2'(p5'A2')$_3$—O—.

3. The composition of claim 1 in which the oligonucleotide is blocked by a blocker selected from the group consisting of a -p3'N5' nucleotide, a p-O-alkylamine, a p-O-hydroxyalkylamine, a sp-O-alkylamine, a sp-O-hydroxyalkylamine, ethyl and methyl.

4. The composition of claim 1 in which the Respiratory Syncytial Virus is the A2 strain, and the portion of the genome is found in conserved regions of gene-start or gene-end signals.

5. The composition of claim 1, in which the oligonucleotide contains one or more phospho-moieties selected from the group consisting of phosphorothioate, methylphosphonate and methylphosphonothioate.

6. The composition of claim 1, in which the oligonucleotide is composed entirely of 2' O-methyl nucleotides.

7. The composition of claim 1 or claim 6, in which the oligonucleotide is complementary to that portion of the RSV genome comprising the sequence: 3' CCCCGUUUA 5'.

8. The composition of claim 1 or claim 6, in which the oligonucleotide is complementary to that portion of the RSV genome comprising the sequence: 3' CCCUGUUUUA 5' (SEQ ID NO:20).

9. The composition of claim 1 or claim 6, in which the oligonucleotide is complementary to that portion of the RSV genome comprising the sequence: 3' UCAAUUNAUAUAUUUU 5' (SEQ ID NO:21).

10. A method of inhibiting Respiratory Syncytial Viral (RSV) infection in a mammalian cell infected with RSV which comprises a step of providing an amount of a complex effective to inhibit RSV infection, said complex comprising:
    a) an antisense oligonucleotide, in which the sequence of said oligonucleotide is complementary to between 15 and 20 nucleotides of a conserved region of the genomic RNA strand of a strain of a Respiratory Syncytial Virus and a terminus of the oligonucleotide is attached to a linker; and
    b) an activator of RNase L attached to the linker.

11. A method of inhibiting Respiratory Syncytial Viral (RSV) infection in a mammalian cell infected with RSV which comprises a step of providing an amount of a complex effective to inhibit RSV infection, said complex comprising:
    a) an antisense oligonucleotide, having a hydroxyl moiety at a first end, in which the sequence of said oligonucleotide is complementary to between about 15 and 20 nucleotides of a normally single stranded portion of the genomic RNA strand of a strain of a Respiratory Syncytial Virus and a terminus of the oligonucleotide is attached to a linker;
    b) an activator of RNase L attached to the linker; and
    c) a pharmaceutically acceptable, aerosolizable carrier.

12. The method of claim 10 or 11 in which the antisense oligonucleotide is 17 5'-3'-linked nucleotides.

13. A composition to inhibit RSV infection in a mammalian cell comprising:
    a) an effective concentration of an oligonucleotide, wherein the oligonucleotide comprising at least one 2' O-methyl modified nucleotide, is between 15 and 20 nucleotides of complementary sequence to a conserved gene-start or gene-end signal of a Respiratory Syncytial Virus genomic RNA strand and is attached to a RNase L activator by a linker; and
    b) a pharmaceutically acceptable carrier.

14. The composition of claim 13, which comprises a pharmaceutically acceptable, aerosolizable carrier.

15. The composition of claim 13 which is in a formulation suitable for nasal administration.

* * * * *

SEQUENCE LISTING

<160> NUMBER OF SEQ ID NOS: 40

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 1
tcaatggtcc ttatctcaa                                                    19

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 2
gagctttatt agcagcatc                                                    19

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 3
aaatcccatc accatcttc                                                    19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 4
caccaccctg ttgctgtag                                                    19

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 5
aaacaatcag catgtgttg                                                    19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 6
aatgtaacga tgtggtgag                                                    19

<210> SEQ ID NO 7
<211> LENGTH: 20

-continued

<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7
ttgtacgcat tttttcgcgt 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 8
gtacttatca aattcttatt 20

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 9
acgcgaaaaa atgcgtact 19

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10
ctcccttggt tagagatgt 19

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 11
gaaatgatgg aattaacat 19

<210> SEQ ID NO 12
<211> LENGTH: 15222
<212> TYPE: DNA
<213> ORGANISM: respiratory syncytial virus

<400> SEQUENCE: 12
acgagaaaaa aagtgtcaaa aactaatatc tcgtaattta gttaatacac atataaacca 60
attagattag ggtttaaatt tattcctcca agattaaaat gataacttta ggattagttc 120
actaaaagtt atttaaaaaa ttatatgatt tttaattttt aataactata attgaataca 180
gtgttagtgt atagctatgg gaatttttat tataagatct ttattcatta ttcattatga 240
aagttgtata acagactacc tgtgatttta atcagttttt taagttcatt ggttgtcaag 300

-continued

```
ctgtttaaca attcacttag gtaaggatat gtagattcta ccatatataa atggttatag      360
tttagttctg ttgatctgaa atttaaaaca tgattgaacc attttaagat gttcatatgc      420
ttatgattta taagtttatt gctgaaaact tcattacgtc cagctataga atatgatagt      480
atatctccac taacaacact ctttagtttt gacaatgcag tattaattcc ttttttttgtt     540 atagggtaac aaagaaaggg tatcaaactt ttaatatttg catcaataga ctctttatca      600
gctttcttag gcatgatgaa attttttggtt cttgatagta tcaatttagc attttgtact     660
acattaaata ctgggaatat attcgcagga cctattgtaa ggactaagta aacctccgat      720 cccttttaact tactgcctaa gcatacataa gttttttaata tagttatatt gtctaatttg    780
aaatcaatat catcttgagc atgatatttt actattaaca tacatttatt aactgaggaa      840
cagtacttgc actttcttac atgcttgctc cattctatta taatttttact ccagttgact    900 gttacagaca attcggcatc acagacaaaa agactgatag gttcagcaaa ctttatatgt      960
aaataagacc aatgaatgtt gttggttgca tctgtagcag gaatggtcaa attttcacca    1020
taatcaatgt tgatatgtcc attgtacagc cttaaaaact caataggtaa actatgatca    1080
ttgcaatctt tcagacttct gtaaatatat cttatgtcag gatgaagttc cactactgta    1140
cgcaataata aattccctgc tccttcacct atgaatgcta tacaattggg atctttaatt    1200
ttaagatctt ttaaaatata ctctatacta attttacaac ctgtagaact aaatacaaaa    1260
ttgaatctat taatatgatg ccaaggaagc atgcagtaaa gtgatgtgct attgtgcact    1320
aaagatattt ggtgggaagt agtagtgtaa agttggttgg atttggctgt attgcctgaa    1380
tgatctataa ttctatcaat cacaaccata gggaataaat tatacaaatc ttgtttgctg    1440
taattggttc taatcattgc agacgattta ataagcttct tattagataa caatggtaac    1500
attattgagt caacattttt acctatacaa tagtcattca gtgtcttttt gtcattactt    1560
ttaatcggat tggctagtat attctctagg gtttctggtg taggatgata taatttgttg    1620
taattatttt ctaattcaga attagcaatc cttatatatt tagttaatag atgagtatta    1680
tctgagaagt tataattaat gtagaagaga ttagaagtat aaaattcatc attgaatttg    1740
tgtttatttt taatgtgtat tctatctata tttatcaatc ccattctaac aagatctata    1800
taagttaata ttgctttcat atgtgttgga tgataatcta tgttaacaac ccaagggcaa    1860
actgtgaatt ctgctacatt aagacgttta agaaaccata atttgaagct atgcatcct     1920 tttactctat gtaaacttgc atcttggcta agaatgtatt tgataacttt ttgttctaaa    1980
aataccttag acatagactt ccaataacta ctgtctatta attccaatac acatagaaga    2040
tctgaagtgt tcatatcaca ctccagcttt gctttgccat aacctttatg aaaacacaag    2100
agataggtct tataagcatt gaagaaaact ttcaaattaa taaacatatg atcagttata    2160
tatccctctc cccaatcttt ttcaaaaata cctttagaat cttcataag ttgtataatc     2220 agaatccaat gtccagctaa attagtactt aaaatgtaag tattatgaaa atagtcagat    2280 atttttatgtg ccaatattaa attagaatta acatgagatc cagatttgag tgttttatta    2340
cttaagaata attccacata ttgagtcaaa cttattttgt ctggtaaaaa catatgctgt    2400
ttttgtatca cttgttttaa cttgtgaata tcaacatcac ctgtgaatat gggaggtttc    2460
atcaaatgta tctcattaag cttaggtatg agaataattc tgttaggaca tacattagta    2520
aattgttcta ctactgacat taaactaagg ccaaagctta tacagttttg gaatactatg    2580
tcaatatctt catcaccata cttttctgtt aatatgcgat taatagggct agtgtcaaag    2640
```

| | | | | |
|---|---|---|---|---|
| tgataatttg | ttgttctata | agctggtatt | gatgcaggga | attcacatgg tctactactg | 2700 |
| actgtaaggc | gatgcaaata | attgacactt | aaatattgtg | gaaataattt cttggccttt | 2760 |
| tcatatgtta | acccaagggt | tcctatgctg | agttcttcca | tgaattcatc cttgttatct | 2820 |
| atagatgcat | acacccaatc | caattttgct | aatagatcta | tttgatctct ctgtttttg | 2880 |
| gttaagactt | gtctattata | aactggcatt | gttttttct | cttgtgtaga tgaaccaacc | 2940 |
| catggtttag | tgggtcctct | ctcaccacgt | gttaaactgt | taacattata tttctctata | 3000 |
| attatgccac | tagatatagt | gcttgtagta | tatttgatgt | ccattgtata catgatactg | 3060 |
| ggtgatgtaa | caccaactat | attggataaa | gaccaagatc | tttccctaac atatttgctt | 3120 |
| aattcagtaa | tacttaggtt | ttccatactc | aatatctctc | ttttatctct gttacaatcc | 3180 |
| aatggaagta | tccttataag | caaagttatg | tttttcctca | tcatctcagt ggctctatca | 3240 |
| atatctgtta | agtctatggc | agaagttttt | tccagtatgt | tagttataga ttttgtacct | 3300 |
| gatataagat | ttactatttt | ctctgctta | taaaagggta | aactttcata aacaactctt | 3360 |
| agcccatgag | gatatgtagg | ttctatattt | tgcataatat | catttagatc tatctctgta | 3420 |
| gtagtataat | gttgtgcact | tttggagaat | attttgtttg | gagctgtact caaaacctct | 3480 |
| gtaactgcca | gtctattgat | ttcgctagta | atttagctt | gtctctcaga ccctaaagct | 3540 |
| tgaggatctc | tcatcaatgt | tacgaattca | gcattaggg | ttttgtcaaa cgtgattatg | 3600 |
| catgttaaga | acttattcaa | tctatcatct | gacagatctt | gaagtttatc ttttaagtca | 3660 |
| tggtttgtat | aataactaag | tatgaacaca | gagtgaacta | tagcctctgt gaggaagtca | 3720 |
| ggagttcttc | tatagaaact | tcgatataac | aagttgggat | caccaccacc aaataacatg | 3780 |
| ggtaaattca | tatacaatgt | taatgctgta | tcaatattat | caagattaaa aaggttttt | 3840 |
| aagtgtttca | gaacctttaa | tatgtccaaa | tatagtttat | tgttacataa tgcatgattt | 3900 |
| tttaattgta | gagcaatctg | attatataac | catacatttc | taaatattaa actgcataat | 3960 |
| agactttcac | ctctatattc | taattcttgt | gtcaaactac | ctatagattc tagactcact | 4020 |
| ttgaaatcat | caagtatagt | gtttatccac | ggtcccactc | ttaggacttt ctttatacta | 4080 |
| gctgggtaat | atacaccgtt | atgttgaatt | gttttactca | taaattgcat atctcgtgat | 4140 |
| atataagtct | cagttccttt | taatttgtgg | cctatgcctg | catactcttt atacagtaat | 4200 |
| ttaaggctat | ttaatgctag | caaataatct | gcttgagcat | gagtttgacc ttccatgagt | 4260 |
| ctgattggtt | tgcttatatc | tattgattga | ttgtcaccat | taattaaagc agtaattgag | 4320 |
| aatttccctt | tgagagatat | tagatccaat | agtgatatag | cttctatggt ccatagtttt | 4380 |
| tgacaccacc | cttcgatgcc | acccatgtga | tatctatata | atccactttg ttcatctaca | 4440 |
| ttgttaagat | ctacaatatg | atctcctata | tagggggtg | catgcctata tgtgcatatt | 4500 |
| attgtgacat | gaggaatagt | taaatgtaac | caggaaaata | gagattgtac accatgcagt | 4560 |
| tcatccagca | catcactaca | aatacatgac | gtttcatatc | gaaatgcttg attgaatttg | 4620 |
| ctgagatctg | tgatgataga | gcacttacta | atgtaattgt | tgtaattatc attgtagcga | 4680 |
| tttgatttgt | tacttattcc | tgctttcaat | tctaatattt | tttgtagttc tagatcacca | 4740 |
| tatcttgtaa | gactttcagg | aaagaattgt | aaaatgtttt | cagctatcat tttctctgcc | 4800 |
| aatatttgaa | cctgtctgaa | cattcccggt | tgcattgcaa | acattctacc tacactgagt | 4860 |
| tctctttctt | tgcctgtcaa | tgataccaca | tgattagggt | tgttgagata actttgatta | 4920 |
| actacacagt | tgtataaatc | acattcattg | aatttgttat | ctcttaaata atactctaat | 4980 |
| actcttcttg | atttatcact | ctcggaaaat | tttaattttt | catgttctat atagttttgt | 5040 |

-continued

```
atgtgtgatg gcatgtaatt tctagggaaa ctagtccata tcaaattttt aggaggtgat    5100
atagctttat catttataat catttcaaga tccactttt taggcaaccg aaactcacga    5160
tagaaacgta gtcctgataa cacaatcaaa tctctttctg taagttccaa caaagaagga    5220
taagtgttta gttatagta agttaaccat cttaagggta aaacaatagc atttcttaaa    5280
gtaggccatc tgttgtaatt atttacaaac ccttttataa ttctatatat aaaggcacct    5340
cttaacatac tcagactgct taacaagtaa aatttggtct cattgcaatt aattttaaca    5400
gcatccatgg cttgtctttc atctaccatt gggtgtccaa atattctgaa caaaaaatat    5460
agttcactca gattgttaag gttattgtca cctgcaagct taattaattt aaggaactta    5520
cttaatagaa ttatccatct gccatttatt atattatcgg acactgtctt atctaataat    5580
gtatgacata ctcttgatag cagattttc tgagctttat tagcagcatc tgtgatgttg    5640 ttgagctac tattataaaa tcgttttctg aattgatctt cttctgttat atttaaaatt    5700
agagacataa taaatccctc tacctctttt attatgtaga acccctcatt gtgaaatagc    5760
tttagtatat aatctccata aaggaatagt tgtgtcaaga taacattatt gaatccgcat    5820
cttaagccta agcttttatt taatgtgttc aagcagttac taatccatgt aattaaacaa    5880
acatttaatc tactaaggct aatatctttc catgtcaaga attgattata ggttgtcaca    5940
gtaattcttt tgagttcctt atgataaact atacaaccat attggttcaa ataaattga    6000 aatccactaa gagtttgatt atctatcaat gtaaacccat ggttttttac ctcatttgat    6060
cgatactgtg ttaatatgtt gtttaatttt gtgtataagt taaaccaatg tattaaccat    6120
gatggaggat gttgcattga acacatcaat ttcttcaaga gtgttgtttt gattgtgtct    6180
ttttgttttg tagagtgatt tttgtctgct ttaagatgag attgattatc tttaacagct    6240
gaaagtatat catctttgat tatggtcgta ataactgagt tgtcttcatc ttgtccattg    6300
ttggatttaa tcttgtcctt ttctttaagc cctagtttat tcaatatagc atagactttg    6360
acatcactta tttctatagc tcttcttatt atctttttaa gtaaattagt ggtagcaatc    6420
tgttctgacg aggtcatact cttgtatgtc ataagtaatg actgaaaata agtaggttct    6480 tctaattta tttcaccttt atgatactta gatattaagg actgtgttat atttagtttc    6540
tttagattca tgtgttctat taatggattt tgtctactaa ttaagttggt ataatcattt    6600
ttgagataag gaccattgaa tatgtaactt cctaaagcat tacactctga aaagagata    6660 acaccttta ataactatc ggttagataa acattagcag aatttccatt aataatggga    6720 tccatttgt cccacaactt gaattgtttg aattaataat gtaacgatgt ggtgagtgtt    6780
agaattgagt gttatgacac taatatatat attgtatata tatcctcaat aataccta    6840 tgttgtagaa aattttgaat tgtgtcaatc aattcttgag aggtccaatg gatttcattg    6900
aatgtttgat tcggtgagta catatggtta tttgggttgt tttgattgaa atatagtgtg    6960
ttcttttgat tatacatagt aactctacat ctacttgtta ttagtatgga agttatacta    7020
caaggatatt tgtcaggtag tatcattatt tttggcatgg tcatttgtat cactaacagt    7080
tgattctttt gggttgttga tggttatgct cttatggata tccaatgtgt ttttgatggt    7140
tttcttcaat acgtctgctg gcaatctttt taacagatgg atagtttgtt tattgttttt    7200
cctgttgctt tcaatatatg atatgacagt attgtacact cttatcttgg gtgaatttag    7260
ctcttcattg tccctcagct ttttgatatc atcactattg agttcagtga ggagtttgct    7320
catggcaaca catgctgatt gtttagttat attgtttatt gatcctatat aactctctag    7380
```

-continued

```
cactccaact acaccaagag catactcttc tgttctgtcc aactctgcag ctccacttat    7440
ttctgataag gtatctatac ttttatccat agacttaagt attctgttta acataaagtt    7500
ttgtcttaca agcagtgcat ggggtggcca ttcaaaataa ttatgactaa aatgacacct    7560
cttaccattt aagcaatgac ctcgaatttc aaatttgcaa ggattccttc gtgacatatt    7620
tgccccagtt ttcatttttta cagatggtaa gttaatctgg cattcaattg tgttttatat    7680
aactataaac taggaatcta cttaaatagt gtaagtgaga tggtttatag atgagagttt    7740
cgatgaagtt cagattttaa gaaaatccaa tgacagatgg gttgtctatg agcagatagt    7800
aaaccattgt aagaacatga ttaggtgcta ttttttattta gttactaaat gcaatattat    7860
ttataccact cagttgatct ttgcttagtg tgactggtgt gcttctggcc ttacagtata    7920
agagcagtcc aacagcaatt aatgataaca atattactat aatcactata attatagtag    7980
ttatcatgat atttatggtg gatttaccag catttacatt atgtaataat tcatcggatt    8040
tacgaataaa tgctaggctc tggttaatct tctcgttgac ttgagatatt gatgcatcaa    8100
attcatcaga ggggaatact aatgggtcat agaaatttat tattggttca ccttttacat    8160
agagactttt accttcttgc ttatttacat aatataatgt gttacctaca gacacagtgt    8220
ccacccttt atttgataca taatcgcacc cgttagaaaa tgtctttatg attccacgat    8280
ttttattgga tgctgtacat ttagttttgc catagcatga cacaatggct cctagagatg    8340
tgataacgga gctgcttaca tctgttttttg aagtcataat tttacaatca tatttggggt    8400
tgaatatgtc aacattgcag agatttactt cacttggtaa tgttaaactg ttcattgtgt    8460
cacaaaatac tcgatttgat tgaactttac atgtttcagc ttgtgggaag aaagatactg    8520
atcctgcatt gtcacagtac catcctctgt cagttcttgt taaacagatg ttggaccctt    8580
cttttgtgtt ggttgtacat agaggggatg tgtgtagttt ccaacagggt gtatctataa    8640
caccatatag tggtaattgt actacatatg ctaagacttc ctctttttatt atggacatga    8700
tagagtaact ttgctgtcta actatttgaa cattgttgga cattaacttt ttctgatcat    8760
ttgttatagg catatcattg attaatgaca ataattcact attagttaac atgtaagtgc    8820
ttacaggtgt agttacacct gcattaacac taaattccct ggtaatctct agtagtctgt    8880
tgttcttttg ttggaactct atcacagttg ctatatttga tatgctgcag ctttgcttgt    8940
tcacaatagg taacaattgt ttatctatat agttttttgag gtctaacact ttgctggtta    9000
agacactaac tccatttgat aagctgacta cagccttgtt tgtggatagt agagcacttt    9060
tgatcttgtt cacttcccct tctaggtgca ggaccttaga tacagcaacg ccactggcga    9120
ttgcagatcc aacacctaac aaaaaaccaa gaaatcttct tttccttttc ttgcttaatg    9180
ttacattggt ttttttggca ttgttgagtg tataattcat aaaccttggt agttctcttc    9240
tggctcgatt gtttgttgct ggtgtgcttt gcatgagcaa ctgcaattct gttacagcat    9300
ttttatattt atctaattct tgttttatca attttacctt agcatctgtt ccattacact    9360
tattttcctt gatattactt aattctatag ttataacact ggtataccaa ccagttctca    9420
gagcactaag atagcctttg ctaactgcac tgcatgttga ttgataaaat tcttcagtga    9480
tgttttgacc agaagcaaaa caaaatgtga ctgcagtgag gattgtggta attgcatttg    9540
ctttgaggat tagcaactcc attgttattt gccccagagt ttattttgat tctgtttaag    9600
ttggtcatgg cttttttgtga taatatgttt ttaagtaact actggcgtgg tgtgttgggt    9660
ggagatgaag gttgtgatgg gtactcgat gttgtagaga cttgagaagg gcttggattg    9720
ccttcggagg aagttgagtg gaaggtttcc atttgacttg tgagttctgg atttcctgtg    9780
```

```
gtgttggagg tgagtagtgt agttatgatg tttgttttgg tggtgttgat ggttggctct    9840
tctgtgggct tggtggtggg tacttccttt gatttagtgg tttgaggttt gggatctttt    9900
ttggttgtct tgagggttgg ttttttttgtg ggcttggtag tggttttctt tcctggtttt   9960
ttgtttggta ttcttttgca gatagcccag caggttggat tgttgctgca tatgctgcag   10020
ggtacaaagt tgaacacttc aaagtgaaaa tcattattgg gtttgcttgg tggtttgttt   10080
tggcgttgtt ttgtggtggg cttgctgggt tgtgtttgag ttgttgttgt gttttttggtc  10140 ttgactgttg tggattgcag ggttgacttg actcctggtg ttgttgaagc tagtatggtg   10200
gtgatttgtg atgtaatttc agacggatta gagggactga ttccaagctg aggattctgg   10260
gtgaggtatg ttggggttgt gttcttgatc tggcttgttg catcttgtat gattgcagtt   10320
gttggtgtga ctttgtggtt tgccgaggct atgaatatga tggctgcaat tataagtgaa   10380
gttgagatta tcattgccag aatggataat gtgatttgtg ctacagattt aagatttaac   10440
ttatataagc acgatgatat gaataataaa tgattgagag tgtcccaggt cctttctaat   10500
gtcttagcgg tgcgttggtc cttgtttttg gacatgtttg catttgcccc aatgttattg   10560
ttagtcttga tatcctagtt cattgttatg actattttta attaactact ttatagtatg   10620
gatagtggtt tgcatggtgg gatgttaatg aggtgttgta aagaggtagg ggttgttcat   10680
ttttaaatgc aaggttactg ttttgggctg ttggattgat gaatgctatg tgttgactcg   10740
agctcttggt aactcaaagg ttttgttatg gaatacgtta tattcacaaa gtttgtttag   10800
tattgcaatc atgatggaga ttatgattag caaagagatt attgttgtga tcatgtgtat   10860
tagtgtaaag taaggccaga atttgcttga gaattctatt gttatggatg tattttccat   10920
tggttgattc tgtatggtgt gtggacttgt ctatgttaac agatattgtg attagttgga   10980
tttcctccaa tgattatttg ccccatgtgt atatttttta ttaacttatt tgagtactag   11040
atctgataaa caatgacttg ggatgatctg ggacttcaga taagttttgt ttgattggtt   11100
gaaccacaga gtgtttgtga ttgtgatggt gaagtgaaga atgtaggtag aaagtttgta   11160
tgaattaaca cactgatgta gaggaaaaag gttaatcttc catgggtttg attgcaaatc   11220
gtgtagctgt gtgcttccaa tttgtggtaa cataatatat actttctttt tctaggtaag   11280
ctccaagatc tactatgaat tgactttgtg gctttatgta tttgaatgct cctttgttgt   11340
cagtcactgt gatgactaat agtaatcctg agtaagggat gatttttgca tttgtgatag   11400 cattttgaa ttcagtggtt gttatatttt caagtgtgtt cagatcttta tttctgacac   11460
tgatggatct taggtatgtt ggtattatga cttttttga tgttactatg ttttcaaatt   11520
cacataaagc aataatatca tgtgtagggt tgagtgtctt catagtgaga tctttaactg   11580
tagtcaacat attttttgat tttaggcatg ttagactaca tgccttgatt tcacagggtg   11640
tggttacatc atatgctagt ttgcttcttt catccaagga cacattagcg catatggtaa   11700
atttgctggg catttgtgct agcactgcac ttcttgagtt tatcatgact cttagtgaag   11760
gtcccttggg tgtggatatt tgtttcacta gtatgttgac attagctagt tcttttataa   11820
gtaaatctgc tggcatagat gattggaaca tgggcaccca tattgtaagt gatgcagggt   11880
catcgtcttt ttctaagaca ttgtattgaa cagcagctgt gtatgtggag ccttcgtgaa   11940
gcttgttcac gtatgtttcc atatttgccc caccctttcc tttttttgta actatattat   12000
agattttttc cggtggtta gttttggatt ggctggttgt tttgttggct gtttggctga   12060
ttggcggatg gatgtttggt tggatgattg ggttggttag tttgttggtc ttctgttggt   12120
```

-continued

```
attgtgtgtt gatgtgaaga ttggtaacta atcagaaatc ttcaagtgat agatcattgt      12180
cactatcatt cccttccaat aggttgttca atttctctga tgttggattg agagacactt      12240
catctgatgt gtcttttgcc atcttttcac tttcctcatt cctgagtctt gccatagctt      12300
ctaatctgtc attggtcatt aatgcttcag ttctgatttt ttctatcatt tcttctctta      12360
aaccaaccat ggcatctctt ataccatccc gagcagatgt aggtcctgca cttgccacta      12420
ctaatgtgtg aagcattcct agtatttcac ttaattttc atcaatccta tctaatcttg       12480
ctgttatatt atcgtttgtc tgatcattta tttcttcgta tgaatagctg gattcttctt      12540
cattgttatc aaatgtttct atggtttctt tgtatagttt agaaagggga ttatcacttg      12600
gtgtagggtc ttcttttgaaa cttactagag gttttctttg ataattgggc ttgttccctg     12660
cagtatcatc tgtctcattt gttgggttga taatagttga atttgatgtt atagggcttt      12720
cttttggttac ttctatatct attgagttga cagatatgat actatctttt ttcttgggat     12780
ctttgggtga tgtgaatttg ccctttattg attctaggaa tttagtagcc ctgttgtttg      12840
catcttctcc atggaattca ggagcaaact tttccatgat gatttatttg ccccattttt      12900
tattaactca aagctctaca tcattatctt ttggattaag ctgatgtttg atagcctcta      12960
gttcttctgc tgtcaagtct agtacactgt agttaatcac accatttttct ttgagttgtt    13020
cagcatatgc ctttgctgca tcatatagat cttgattcct cggtgtacct ctgtactctc      13080
ccattatgcc taggccagca gcattgccta atactacact ggagaagtga ggaaattgag      13140
tcaaagataa taatgatgct tttgggttgt tcaatatatg gtagaatcct gcttcaccac      13200
ccaatttttg ggcatattca taaacctcaa caacttgttc catttctgct tgcacactag      13260
catgtcctaa cataatatt ttaattgatt ttgctaagac tccccaccgt aacatcactt        13320
gccctgcacc ataggcattc ataaacaatc ctgcaaaaat cccttcaact ctactgccac      13380
ctctggtaga agattgtgct ataccaaaat gaacaaaaac atctataaag tggggatgtt      13440
tttcaaacac ttcatagaag ctgttggcta tgtccttggg tagtaagcct ttgtaacgtt      13500
tcatttcatt ttttaggaca ttattagctc tcctaatcac ggctgtaaga ccagatctgt      13560
cccctgctgc taatttagtt attactaatg ctgctataca taatattatc atcccacaat      13620
caggagagtc atgcctgtat tctggagcta cctctcccat ttcttttagc attttttttgt    13680
aggattttct agattctatc tcaatgttga tttgaatttc agttgttaag cttgccaatg      13740
ttaacacttc aaatttcatt tcttttccat taatgtcttg acgatgtgtt gttacatcta      13800
ctccatttgc ttttacatga tatcccgcat ctctgagtat ttttatggtg tcttctcttc      13860
ctaacctaga catcgcatat aacataccta ttaacccagt gaatttatga ttagcatctt      13920
ctgtgattaa taacatgcca cataacttat tgatgtgttt ctgcacatca taattaggag      13980
tatcaatact atctccctgtg ctccgttgga tggtgtattt gctggatgac agaagttgat    14040
ctttgttgag tgtatcattc aacttgactt tgctaagagc catctttgta tttgccccat      14100
cttctatctt atatctctcc ttaattttaa attactataa ttttcaggct ccatctggac      14160
tatggagtat agttatgcat agagttgttg ttttagattg tgtgaatatt gtgttgaaat      14220
ttatggattg agatcatact tgtatattat gggagtatgc tttgtaggct taatgccaat      14280
gcattctaag aacccatcat gattgatgaa tattggcata gggaaagtgc catattttgt      14340
gttgtattca gtatattttt tatatttagt gcttcctact ttgtgtaata gtttcatttc      14400
atagttgacc aggaatgtaa atgtggcctg tcttttcatca agttttctca ctatgcattc    14460
atgatttatc aagtatataa atttgtgtgt tatgatgtct ctggttagtg atgttattat      14520
```

```
ggtctcaagt gacaacggtc tcatgtctgt gatcatcagt ctttgtggtg tattatcatt      14580
gtgggttgtg tccatggttg ggttggctga attgatttat ttgccccatt tttgtcttct      14640
gttaagtttt atattaacta atggtgttag tgacattgat ttgctagttg atattaatta      14700
taatttatgg attaagatca aatccaagta attcagataa ttgattcata taattggtca      14760
ttgttgaatc acttagtttt ttggagaatt taatttcaca attgtcatct agtagaccat      14820
taggttgaga gcaatgtgtt aattccatca tttcccatat ataacctcca ttttgtagta      14880
ctggcattgt tgtgaaattg gattttacta caatattatt attagggcaa atatcactac      14940
ttgtaataac atgcacaaac acaatgccat tcaatttgat tgtatgtatc actgccttag      15000
ccaaagcatt agtaaatgt attaatttat cagtatagca tgttattttt aacaatgcta      15060
cttcatcatt gtcaaacaaa ttttgtaatc aactttat catactcaat gaattgctgc      15120
ccatctctaa ccaagggagt taaatttaag tggtacttat caaattctta tttgccccat      15180
ttttttggtt tatgcaagtt tgttgtacgc attttttcgc gt                        15222
```

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 13
aaaaatgggg caaataa                                                        17

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 14
gaagatgggg caaatac                                                        17

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 15
aagggagggg caaatat                                                        17

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 16
acacatgggg caaataa                                                        17

<210> SEQ ID NO 17

-continued

```
<211> LENGTH: 17
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 17
aacacagggg caaatat                                                    17

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 18
aaaactgggg caaatat                                                    17

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 19
agttgtggga caaaatg                                                    17

<210> SEQ ID NO 20
<211> LENGTH: 10
<212> TYPE: RNA
<213> ORGANISM: respiratory syncytial virus

<400> SEQUENCE: 20
auuuuguccc                                                            10

<210> SEQ ID NO 21
<211> LENGTH: 16
<212> TYPE: RNA
<213> ORGANISM: respiratory syncytial virus
<220> FEATURE:
<221> NAME/KEY: modified_base
<222> LOCATION: (10)
<223> OTHER INFORMATION: n=a,c,g, or u

<400> SEQUENCE: 21
uuuuauauan uuaacu                                                     16

<210> SEQ ID NO 22
<211> LENGTH: 17
<212> TYPE: RNA
<213> ORGANISM: Artificial Sequence
<220> FEATURE:
<223> OTHER INFORMATION: Description of Artificial Sequence:
      oligonucleotide

<400> SEQUENCE: 22
uuauuugccc cauuuuu                                                    17

<210> SEQ ID NO 23
<211> LENGTH: 17
<212> TYPE: RNA
<213> ORGANISM: Artificial Sequence
```

```
<220> FEATURE:
<223> OTHER INFORMATION: Description of Artificial Sequence:
      oligonucleotide

<400> SEQUENCE: 23
guauuugccc caucuuc                                                    17

<210> SEQ ID NO 24
<211> LENGTH: 17
<212> TYPE: RNA
<213> ORGANISM: Artificial Sequence
<220> FEATURE:
<223> OTHER INFORMATION: Description of Artificial Sequence:
      oligonucleotide

<400> SEQUENCE: 24
uuauuugccc cauuuuu                                                    17

<210> SEQ ID NO 25
<211> LENGTH: 17
<212> TYPE: RNA
<213> ORGANISM: Artificial Sequence
<220> FEATURE:
<223> OTHER INFORMATION: Description of Artificial Sequence:
      oligonucleotide

<400> SEQUENCE: 25
auauuugccc cacccuu                                                    17

<210> SEQ ID NO 26
<211> LENGTH: 17
<212> TYPE: RNA
<213> ORGANISM: Artificial Sequence
<220> FEATURE:
<223> OTHER INFORMATION: Description of Artificial Sequence:
      oligonucleotide

<400> SEQUENCE: 26
uuauuugccc caugugu                                                    17

<210> SEQ ID NO 27
<211> LENGTH: 17
<212> TYPE: RNA
<213> ORGANISM: Artificial Sequence
<220> FEATURE:
<223> OTHER INFORMATION: Description of Artificial Sequence:
      oligonucleotide

<400> SEQUENCE: 27
auauuugccc caguguu                                                    17

<210> SEQ ID NO 28
<211> LENGTH: 17
<212> TYPE: RNA
<213> ORGANISM: Artificial Sequence
<220> FEATURE:
<223> OTHER INFORMATION: Description of Artificial Sequence:
      oligonucleotide

<400> SEQUENCE: 28
auauuugccc caguuuu                                                    17

<210> SEQ ID NO 29
<211> LENGTH: 17
<212> TYPE: RNA
<213> ORGANISM: Artificial Sequence
<220> FEATURE:
```

```
<223> OTHER INFORMATION: Description of Artificial Sequence:
      oligonucleotide

<400> SEQUENCE: 29
cauuuugucc cacaacu                                                    17

<210> SEQ ID NO 30
<211> LENGTH: 17
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 30
ataaggggaa cataaaa                                                    17

<210> SEQ ID NO 31
<211> LENGTH: 17
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 31
gaagacagaa taagata                                                    17

<210> SEQ ID NO 32
<211> LENGTH: 17
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 32
gatagaaata gaaagca                                                    17

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 33
aatgggatcc attttgtccc                                                 20

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 34
ctatcggtta gataaaca                                                   18

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence:
```

```
            oligonucleotide

<400> SEQUENCE: 35
gataaggacc attgaatatg                                                20

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 36
ctctgagaaa gagataac                                                  18

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 37
gattgaaata tagtgtgtt                                                 19

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 38
atagtgtgtt cttttcatta                                                20

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 39
atggttattt gggttgttt                                                 19

<210> SEQ ID NO 40
<211> LENGTH: 19
<212> TYPE: DNA
<213> ORGANISM: respiratory syncytial virus

<400> SEQUENCE: 40
ttttattgga tgctgtaca                                                 19
```